(12) United States Patent
Honda et al.

(10) Patent No.: US 9,334,069 B1
(45) Date of Patent: May 10, 2016

(54) PROPELLANT GAUGING AT MICROGRAVITY WITHIN THE PRESSURE—TEMPERATURE—DENSITY INFLECTION ZONE OF XENON

(71) Applicant: The Boeing Company, Chicago, IL (US)

(72) Inventors: Linton Kankeki Honda, Rancho Palos Verdes, CA (US); Steven Edward Core, Redondo Beach, CA (US); Gregory Cardon McDonald, Torrance, CA (US)

(73) Assignee: The Boeing Company, Chicago, IL (US)

( * ) Notice: Subject to any disclaimer, the term of this patent is extended or adjusted under 35 U.S.C. 154(b) by 727 days.

(21) Appl. No.: 13/658,758

(22) Filed: Oct. 23, 2012

(51) Int. Cl.
*B64G 1/22* (2006.01)
*B67D 1/00* (2006.01)
*B64G 1/40* (2006.01)
*F02K 9/44* (2006.01)

(52) U.S. Cl.
CPC . *B64G 1/402* (2013.01); *B64G 1/22* (2013.01); *F02K 9/44* (2013.01)

(58) Field of Classification Search
CPC .......... B64G 1/402; B64G 1/401; B64G 1/26; F02K 9/42; F02K 9/44; F02K 9/50; F02K 9/605; F17C 2223/0161; F17C 2223/0194; F17C 2223/0439; G01F 22/02; G01F 22/14; G01F 22/246
USPC .......... 73/49.2, 149, 167, 295; 702/1, 85, 108
See application file for complete search history.

(56) References Cited

U.S. PATENT DOCUMENTS

| | | | | |
|---|---|---|---|---|
| 4,827,762 | A * | 5/1989 | Hasselmann | G01F 1/007 702/41 |
| 5,700,088 | A * | 12/1997 | Piacente | G01K 1/20 102/481 |
| 6,609,363 | B1 * | 8/2003 | Dressler et al. | 60/202 |
| 8,781,652 | B2 * | 7/2014 | Vu | 701/13 |
| 2002/0011094 | A1 * | 1/2002 | Cook | F02M 25/0809 73/49.2 |
| 2004/0035982 | A1 * | 2/2004 | Capozzi et al. | 244/172 |
| 2008/0140336 | A1 * | 6/2008 | Home | G01F 23/14 702/130 |
| 2009/0031700 | A1 * | 2/2009 | Karabeyoglu | 60/205 |
| 2009/0133788 | A1 * | 5/2009 | Mungas et al. | 149/74 |
| 2010/0000232 | A1 * | 1/2010 | Valentian | 62/6 |
| 2010/0212404 | A1 * | 8/2010 | Wolford et al. | 73/45.5 |
| 2014/0032092 | A1 * | 1/2014 | Vu | 701/123 |

* cited by examiner

*Primary Examiner* — John Breene
*Assistant Examiner* — Jeffrey Aiello
(74) *Attorney, Agent, or Firm* — Felix L. Fischer

(57) ABSTRACT

A method that is stored in tangible form and accessible by a data processing system for determination of xenon propellant remaining in a tank for a defined life condition. A heater controller establishes a first stable temperature of a propellant tank. A measurement is performed of a temperature and a pressure at the first stable temperature of the propellant tank. A second higher stable temperature is provided in the propellant tank. A measurement is performed of a temperature and a pressure at a second stable temperature. A computer processor computes a mass based on density and volume in accordance with measurements of temperature and pressure at the first stable temperature and the second stable temperature.

20 Claims, 7 Drawing Sheets

PROPELLANT GAUGING AT MICROGRAVITY WITHIN THE PRESSURE—TEMPERATURE—DENSITY INFLECTION ZONE OF XENON

BACKGROUND INFORMATION

1. Field

Embodiments of the disclosure relate generally to the field of propellant mass remaining calculation for propellant (such as xenon) tanks and more particularly to a method for calculating mass of xenon as a non-ideal gas using controlled temperature differential to induce associated pressure differential allowing an iterative differential pressure and temperature calculation with known tank volume to back calculate xenon mass remaining.

2. Background

Xenon thrusters are employed in many spacecraft applications for station keeping and on-orbit maneuvering. Xenon used as a propellant is a non-ideal gas. Propellant quantity gauging for xenon in microgravity is therefore very difficult along the pressure-temperature-density inflection zone because small changes in pressure or temperature can change the calculated density by over 100%. Diurnal effects impact gauging measurements due to changing environmental conditions of the spacecraft. Additionally, small biases or inaccuracies in the telemetry can also cause significant uncertainty in mass remaining. Current quantity gauging is accomplished by book-keeping methods subtracting estimated amounts of propellant processed during each thruster operation for defining remaining quantity of propellant until quantity and associated pressure in the tank drops below approximately 1 MPa at which point ideal gas calculations for mass based on pressure, volume, density, and temperature can be assumed with reasonable accuracy.

It is therefore desirable to provide a method for calculation of xenon mass in a propellant tank which corrects for non-ideal gas properties and sensor biases for a range of propellant quantities in which ideal gas calculations cannot be accurately used.

SUMMARY

Embodiments disclosed herein provide a method for determination of xenon propellant remaining in a tank for a defined spacecraft on-orbit service life condition by establishing a first stable temperature of a propellant tank. Measurement of temperature and pressure at the first fixed temperature is accomplished. A second higher stable temperature is then established in the propellant tank. Measurement of temperature and pressure is then accomplished at the higher temperature. The two measurements of temperature and pressure are then used to calculate the mass of remaining propellant based on known xenon density properties and tank volume.

The features, functions, and advantages that have been discussed can be achieved independently in various embodiments of the present disclosure or may be combined in yet other embodiments further details of which can be seen with reference to the following description and drawings.

DETAILED DESCRIPTION

Figure 1:
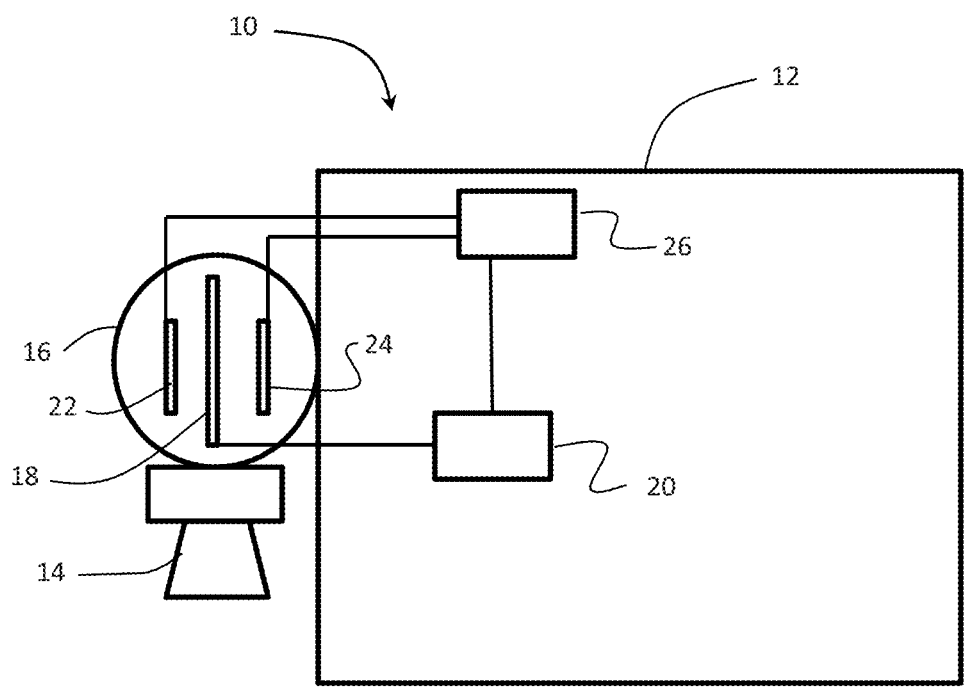
FIG. 1 is a block diagram schematic of a spacecraft xenon propellant feed system.

Embodiments disclosed herein provide a method for calculating the remaining mass in a xenon propellant tank in a quantity range in which ideal gas behavior is not present. As shown in FIG. 1, an example satellite system 10 employs a spacecraft platform 12 containing scientific experiments, communication system or other satellite payload. Included on the platform are xenon thrusters 14 (one is shown as an example but numerous thrusters at various locations on the platform and with varying thrust axes are employed). A propellant tank 16 holds xenon propellant for the thrusters. Within the tank a heater element 18 is present to allow tank temperature control and resulting pressure control. Tank temperature control may be augmented with thermal blankets. A heater controller 20 provides controlled power to the heater. A temperature sensor 22 and a pressure sensor 24 in the tank measure temperature and pressure and provide data to a control computer 26. The control computer is connected to the heater controller for control of the heater to achieve desired temperatures within the tank.

Figure 2:
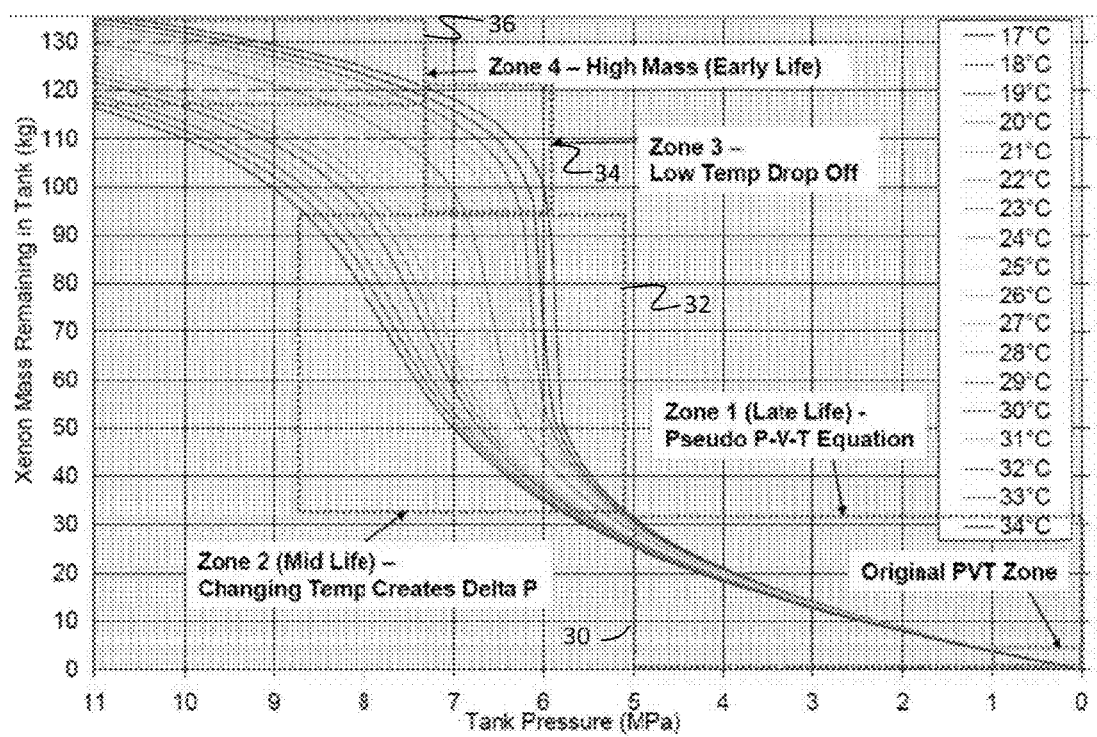
FIG. 2 is a graphical representation of the relationship between temperature, pressure and mass for xenon in an example tank of known volume using pure xenon density properties.

The amount of xenon propellant remaining in the tank 16 needs to be known to properly plan satellite control using the thrusters 14. However, xenon is not an ideal gas. Consequently, usual gaseous propellant gauging techniques using temperature, pressure and the known volume of the propellant tank are not effective for the majority of the usable range of propellant quantity. FIG. 2 shows the non-ideal nature of xenon for an example propellant tank having an initial quantity of approximately 135 kg of xenon with curves for parametric temperatures plotted against pressure and corresponding mass remaining in the tank. Since knowledge of remaining quantity of propellant becomes more critical as the total available propellant approaches exhaustion, zones of propellant quantity (or depletion zones) have been established based on criticality of the measurement and availability of measurement techniques. As shown in FIG. 2, Zone 1, within block 30, where the tank nears exhaustion of propellant, is established in a pressure regime in which ideal gas behavior may be approximated and used for measurement of the remaining propellant quantity. Zone 2, within block 32, is the zone where husbanding of propellant and knowledge of quantity remaining is most difficult to ascertain to assure desired mission service life longevity, constitutes the zone for which the present embodiments are most useful. Zone 3, within block 34, referred to as the low temperature drop off point, is a limited range and near the full condition in which accurate gauging is not as critical. Zone 4, within block 36, is the early life condition where the tank is nearly full and book-keeping methods, tabular look up or pseudo polynomial calculations based on pressure and temperature may be used to estimate propellant quantity.

Figure 3:
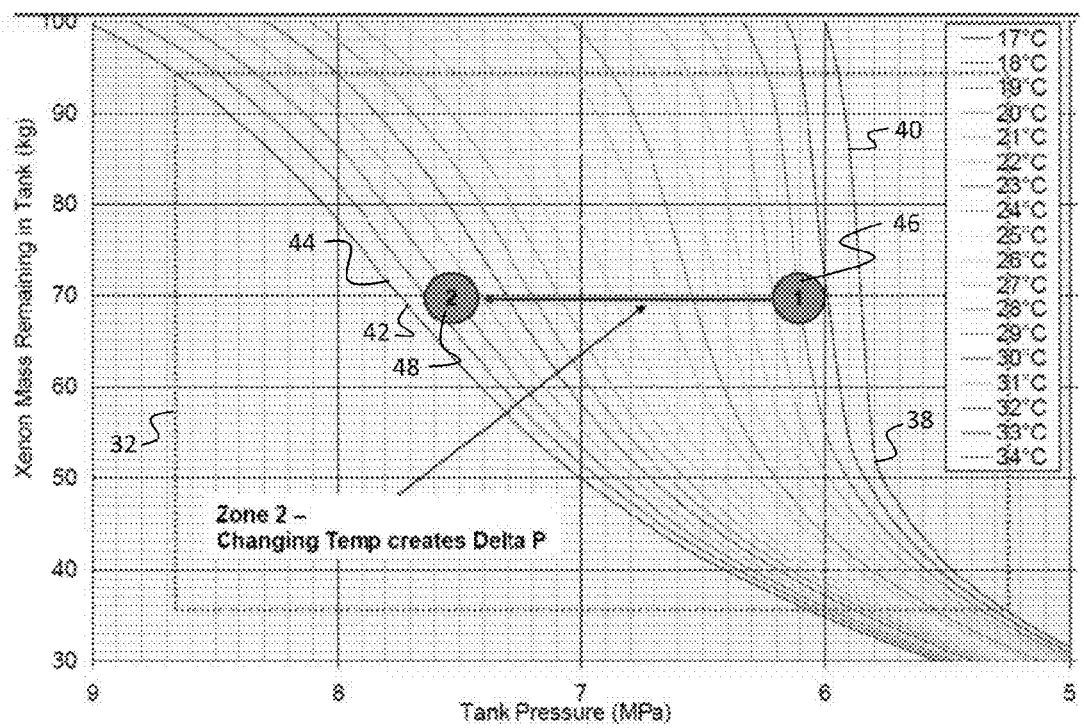
FIG. 3 is a detail section graphical representation of the Zone 2 Midlife portion of FIG. 2.

Examining zone 2 in detail in FIG. 3 it can be seen that at lower temperatures and a given pressure, the mass remaining varies extensively (near vertical slope). For example with a temperature of 17° C. a pressure differential of 0.1 MPa between 5.8 and 5.9 MPa can have a mass range of approximately 52 kg, point 38, to 86 kg, point 40 in mass remaining. However, at 34° C. that same pressure differential of 0.1 MPa between 7.7 and 7.8 MPa only has a mass range of approximately 69 kg, point 42, to 71 kg, point 44. By determining the pressure differential created by an induced temperature differential it is then possible to determine an associated mass remaining with a significantly higher degree of accuracy. Demonstrated graphically in FIG. 3, by establishing and maintaining a tank temperature of 19° C. using the heater element 18 under control of the heater controller 20 if 70 kg xenon is in the tank, a pressure of 6.1 MPa, point 46, will be measured. Increasing the temperature to a new stabilized point of 32° C. and measuring the resulting pressure as 7.55 MPa, point 48, allows a determination that the mass is, in fact, 70 kg of xenon. Since there is no change in mass (or negligible change since actual usage of xenon over a couple of days of station-keeping maneuvering for thruster burns is very small), the determined change in pressure (delta P) for a given change in temperature (delta T) can only occur at a specific mass remaining. While described herein for xenon as the propellant, the structure and method disclosed in the embodiments is applicable for gauging of mass remaining for alternative gases having non-ideal characteristics with a significant S-curve or inflection and spread in the temperature, pressure and density as demonstrated in FIG. 3.

Figure 4:
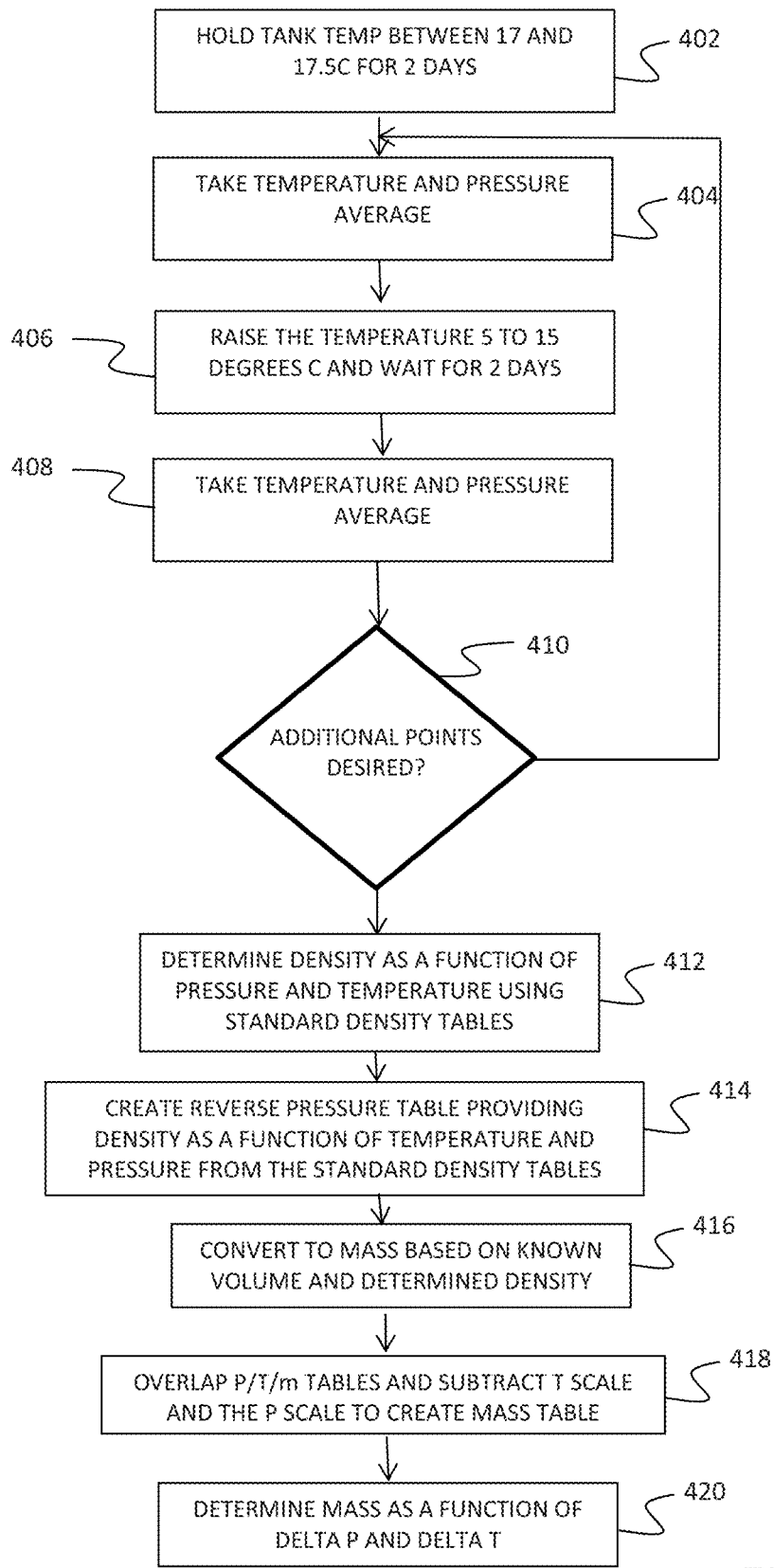
FIG. 4 is a flow chart showing the determination of mass remaining in a tank based on measured temperature and pressure change.

Employing this relationship, calculation of remaining xenon propellant in the tank can be accomplished as defined in FIG. 4. Using the heater controller 20 to control the heater element 18, establish and hold tank temperature as measured by the temperature sensor 22 at an initial temperature (for the example case, between 17 and 17.5° C.), step 402. Measure temperature and pressure average over a approximately a two day period, step 404. Raise the temperature by a delta T of 5 to 15 degree C. and hold for approximately 2 days, step 406. Measure temperature and pressure average, step 408. Steps 404 through 408 may be repeated to obtain additional measurement points, step 410. For each stabilized temperature a density is then determined as a function of pressure and temperature using standard density tables, step 412. A reverse pressure table providing density as a function of temperature and pressure is created from the standard density tables, step 414. The known volume of the propellant tank as a function of pressure and temperature allows xenon propellant mass to be determined from corresponding density in the pressure/temperature/density tables and substituted in either or both tables, step 416. Pressure/temperature/mass tables are then overlapped and the temperature scale and pressure scale are subtracted to create a mass table, step 418 (a detailed example will provided subsequently). The mass remaining is then determined as a function of delta P and delta T, step 420.

Figure 5:
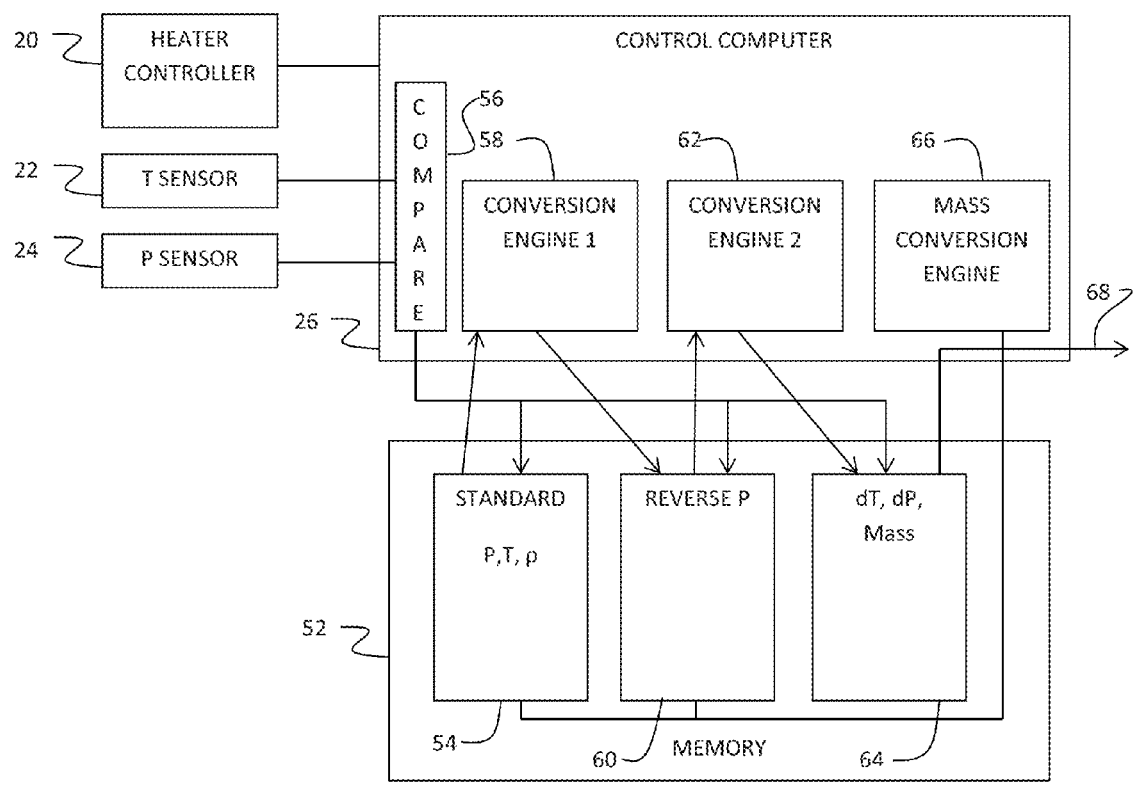
FIG. 5 is a block diagram of elements of the propellant mass gauging system.

As shown in FIG. 5, implementation of an embodiment of the xenon propellant zone 2 gauging system is accomplished with the heater controller 20 under direction of a control computer 26 which receives input from the temperature sensor 22 and pressure sensor 24. The spacecraft or ground-based control computer 26 employs a memory 52 storing a standardized pressure/temperature/density table 54 for xenon in zone 2. The control computer 26 commands the heater controller 20 to maintain desired temperatures at a selected series of hold points as defined previously with respect to FIG. 4. Pressure and temperature data from each hold point is operated on by a compare routine 56 using table 54 to obtain a density value for each hold point. A first conversion engine 58 creates and stores a reverse pressure calculation table 60 in memory 52. A mass calculation engine 66 employing measured or calculated volume of the xenon propellant storage tank 16 converts density to mass based on pressure and temperature of the tank in either or both tables 54 and 60. A second conversion engine 62 operates on the data of the reverse pressure calculation table 60 selecting pressure differentials based on temperature differentials to provide a table 64 of mass for each temperature differential, dT, in the hold points as a function of measured pressure differential, dP. The control computer 26 provides an output 68 reflecting remaining mass of xenon in the propellant tank as determined from dP and dT. Examples for tables 54, 60 and 64 with mass conversion as determined by mass calculation engine 66 are provided in appendix 1, appendix 2 and appendix 3, respectively, of this application. As previously described with respect to FIG. 4, appendix 2 is determined from appendix 1 by reversing the pressure and density in the table such that density/mass is shown in the left column as a function of temperature in the first row and associated pressures in the table body. Conversion of density to mass using known volume of the example tank at the corresponding pressures and temperatures is accomplished at the table of appendix 1 for this example. Appendix 3 is determined from appendix 2 by subtracting the temperature columns of appendix 2 as a function of mass (or density) from the initial column (i.e. 35.1 C column minus the 17.2 C column). The pressure within each row of a temperature column is also subtracted giving a delta pressure row in the table body of appendix 3. The resulting array in appendix 3 is expressed as a function of delta T and delta P. For appendix 3, the arrays are then rearranged so that for given delta T and P, a mass is then found in the left most column of the table. For example in Appendix 3, for 18 C delta (the furthest right column and 1.675 MPa delta pressure highlighted, the mass is found to the left to be 61.4 kg.

EXAMPLE 1

An exemplary determination of remaining mass of xenon propellant using the xenon propellant zone 2 gauging system as described was made. Temperature of the exemplary tank was set by the heater controller at 17.25° C. +/−0.25° C. Data was recorded every minute for approximately 2 days to establish steady state conditions of the tank. Data was recorded for approximately 2 days and an average pressure and temperature of approximately 5.7 MPa at 17.2° C. was obtained. As a reference a standard mass calculation using available NIST 12 pure xenon density property tables and tank volume for the stabilized pressure and temperature indicates a mass remaining of 50.6 kg+/−20 kg. A second temperature of 35.25° C. +/−0.25° C. was commanded and data recorded for approximately 2 days to demonstrate steady state conditions of the tank. Data was recorded for 2 days at the steady state conditions and an average pressure of approximately 7.4 MPa and average temperature of 35.1° C. was obtained. Again as a reference a calculation using NIST 12 xenon density property tables was made indicating a mass of 58.6 kg+/−10 kg. Using the differential pressure between the two stabilized conditions of 1.7 MPa and differential temperature of 17.9° C. and operating on that differential data with table 64 (appendix 3) as defined herein provided a mass calculation of 61.4 kg+/−3 kg demonstrating significantly greater mass remaining accuracy than individual NIST 12 density and tank volume calculations.

Figure 6:
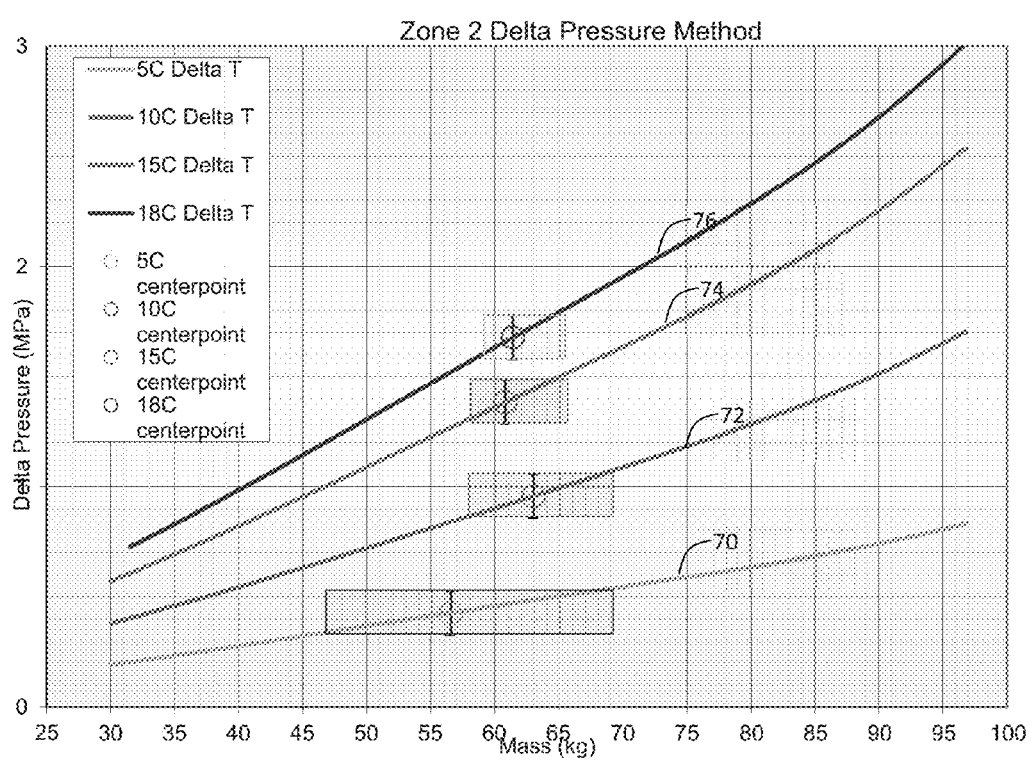
FIG. 6 is a graph of mass remaining at differential pressures based on differential temperatures; and, FIG. 7 is a block diagram of a computer architecture which may be employed for the propellant mass gauging system.

FIG. 6 is a graphical representation of the data provided by table 64. The available uncertainty of the mass remaining data extraction demonstrated by the increasing slope of the curves 70, 72, 74 and 76 for differential temperatures of 5° C., 10° C., 15° C. and 18° C. respectively with greatest mass remaining accuracy (i.e. minimum uncertainty) provided by the largest shown differential temperature at 18° C.

Figure 7:
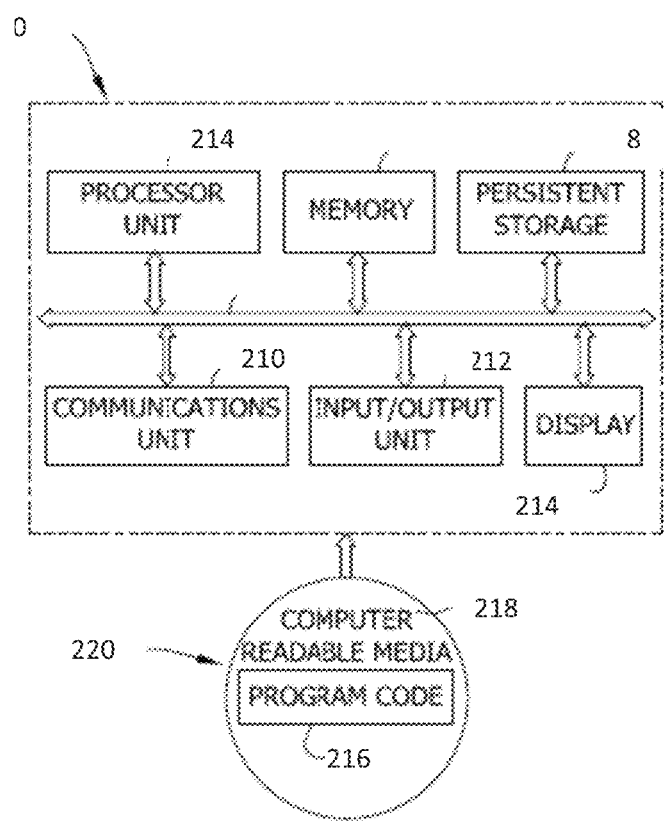

FIG. 7 is a diagram of an exemplary data processing system 200 that may be used in implementing one or more of the embodiments described herein. For example, control of xenon thrusters 14, and heater controller 20, data acquisition from temperature sensor 22, pressure sensor 24, the functions of control computer 26 and memory 52, software modules such as first conversion engine 58, second conversion engine 62, mass calculation table 66, table 54 to obtain density value for each hold point, table 64 of density for each pressure differential, reverse pressure calculation table 60 in memory 52, and/or one or more components integrated in satellite system 10 or xenon propellant Zone 1, 2, 3, 4 gauging system(s) discussed above may be implemented using data processing system 200. In the exemplary embodiment, data processing system 200 includes communications fabric 202 providing communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. In one example, processor unit 204 is implemented using one or more heterogeneous processor systems including a main processor and one or more secondary processors on a single chip.

Processor unit 204 may be a multi-processor system containing multiple, same type processors. Processor unit 204 may be implemented using one or more programmable circuits including one or more systems and microcontrollers, programmable logic circuits, field programmable gate arrays (FPGA), microprocessors, application specific integrated circuits (ASIC), and other like circuits capable of executing the functions described herein.

Memory 206 and persistent storage 208 are examples of storage devices capable of storing information including the software modules either on a temporary basis and/or a permanent basis. In another example, memory 206, may be a random access memory or any other volatile or non-volatile storage device or the like. Persistent storage 208 may take various forms depending on the particular implementation. In one instance, persistent storage 208 may be a fixed or removable hard drive, a flash memory, a rewritable optical disk, a rewritable magnetic tape, or some combination of the above. In one example, a removable hard drive may be used for persistent storage 208.

Input/output unit 212 provides input and output of data with one or more other devices that may be connected to data processing system 200.

Input/output unit 212 may provide, for example, without limitation, a connection for user input through a keyboard and mouse. Input and/or output unit 212 may send output to a printer. Display 214 provides a mechanism to display information to a user.

Communications unit 210, in these examples, provides for communications with other data processing systems or devices. In these examples, communications unit 210 is a network interface card. Communications unit 210 may provide communications through the use of either or both physical and wireless communication links. Instructions for the operating system and applications or programs are located on persistent storage 208. Instructions may be loaded into memory 206 for execution by processor unit 204. Processes of various embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 to operate, for example, first conversion engine 58, second conversion engine 62, mass calculation engine 66, or control computer 26 or other components of satellite system 10 is located in a functional form on computer readable media 218 that is selectively removable and may be loaded onto or transferred to data processing system 200 for execution by processor unit 204. Program code 216 and computer readable media 218 form computer program product 220 in these examples. Computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. Computer readable media 218 may take the form of a tangible form including persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 1000 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

In some illustrative embodiments, program code 216 may be downloaded over a network to persistent storage 208 from another device or data processing system for use within data processing system 200. For instance, program code stored in a computer readable storage medium in a server data processing system may be downloaded over a network from the server to data processing system 200. The data processing system providing program code 216 may be a server computer, a client computer, or some other device capable of storing and transmitting program code 216.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 7 can be varied from the illustrative examples shown.

In one variant, a storage device in data processing system 200 may be any hardware apparatus that may store data. Memory 206, persistent storage 208 and computer readable media 218 are examples of storage devices in a tangible form. In another example, a bus system may be used to implement communications fabric 202 and may be comprised of one or more buses, such as a system bus or an input/output bus. In another variant, the bus system may be implemented using any type of architecture that provides for a transfer of data between components or devices attached to the bus system. Additionally, a communications unit may include one or more devices used to transmit and receive data, such as a modem or a network adapter. For example and without limitation, memory 206 or a cache such as that found in an interface and memory controller hub that may be present in communications fabric 202.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

APPENDIX 1

Standard Mass Calculation

| Pressure | Temps | | | | |
|---|---|---|---|---|---|
| | 15.1 | 17.2 | 20.1 C. | 25.1 C. | 35.1 C. |
| 5 | 32.73903 | 31.41732 | 29.92593 | 27.91992 | 25.06581 |
| 5.0025 | 32.77913 | 31.45191 | 29.95636 | 27.94483 | 25.0862 |
| 5.005 | 32.81855 | 31.48649 | 29.98611 | 27.96975 | 25.10558 |
| 5.0075 | 32.85865 | 31.52176 | 30.01655 | 27.99466 | 25.12497 |
| 5.01 | 32.89876 | 31.55635 | 30.01699 | 28.02027 | 25.14505 |
| 5.0125 | 32.93886 | 31.59162 | 30.07674 | 28.04518 | 25.16444 |
| 5.015 | 32.97897 | 31.62689 | 30.10718 | 28.07079 | 25.18383 |
| 5.0175 | 33.01908 | 31.66148 | 30.13762 | 28.09571 | 25.20391 |
| 5.02 | 33.05918 | 31.69675 | 30.16807 | 28.12062 | 25.2233 |
| 5.0225 | 33.09998 | 31.73202 | 30.19851 | 28.14623 | 25.24337 |
| 5.025 | 33.14078 | 31.76799 | 30.22895 | 28.17183 | 25.26276 |
| 5.0275 | 33.18157 | 31.80326 | 30.26008 | 28.19675 | 25.28284 |
| 5.03 | 33.22237 | 31.83854 | 30.29052 | 28.22236 | 25.30223 |
| 5.0325 | 33.26317 | 31.87450 | 30.32096 | 28.24796 | 25.32231 |
| 5.035 | 33.30397 | 31.90978 | 30.35209 | 28.27288 | 25.3417 |
| 5.0375 | 33.34476 | 31.94574 | 30.38253 | 28.29849 | 25.36178 |
| 5.04 | 33.38825 | 31.98171 | 30.41367 | 28.32409 | 25.38117 |
| 5.0425 | 33.42774 | 32.01698 | 30.44411 | 28.3497 | 25.40125 |
| 5.045 | 33.46923 | 32.05295 | 30.47524 | 28.37531 | 25.42064 |
| 5.0475 | 33.51072 | 32.08960 | 30.50637 | 28.40091 | 25.44072 |
| 5.05 | 33.55221 | 32.12557 | 30.5375 | 28.42652 | 25.4608 |
| 5.0252 | 33.59439 | 32.16154 | 30.56795 | 28.45213 | 25.48019 |
| 5.055 | 33.63588 | 32.19819 | 30.59908 | 28.47774 | 25.50027 |
| 5.0575 | 33.67806 | 32.23418 | 30.63021 | 28.50334 | 25.52035 |
| 5.06 | 33.72024 | 32.27082 | 30.66203 | 28.52895 | 25.53974 |
| 5.0625 | 33.76242 | 32.30678 | 30.69317 | 28.55456 | 25.55982 |
| 5.065 | 33.8046 | 32.34344 | 30.7243 | 28.58086 | 25.5799 |
| 5.0675 | 33.8474 | 32.38010 | 30.75543 | 28.60647 | 25.59998 |
| 5.07 | 33.88965 | 32.41675 | 30.78726 | 28.63207 | 25.62006 |
| 5.0725 | 33.93252 | 32.45410 | 30.81839 | 28.65837 | 25.63945 |
| 5.075 | 33.97539 | 32.49076 | 30.85022 | 28.68398 | 25.65953 |
| 5.0775 | 34.01826 | 32.52742 | 30.88204 | 28.71028 | 25.67961 |
| 5.08 | 34.06113 | 32.56476 | 30.91317 | 28.73589 | 25.69969 |
| 5.0825 | 34.10469 | 32.60211 | 30.945 | 28.76219 | 25.71977 |
| 5.085 | 34.14825 | 32.63877 | 30.97682 | 28.7878 | 25.73986 |
| 5.0875 | 34.19113 | 32.67612 | 31.00865 | 28.8141 | 25.75994 |
| 5.09 | 34.23469 | 32.71347 | 31.04047 | 28.8404 | 25.78002 |
| 5.0925 | 34.27894 | 32.75151 | 31.0723 | 28.866 | 25.8001 |
| 5.095 | 34.3225 | 32.78886 | 31.10412 | 28.8923 | 25.82018 |
| 5.0975 | 34.36676 | 32.82621 | 31.13595 | 28.9186 | 25.84026 |
| 5.1 | 34.41032 | 32.86425 | 31.16846 | 28.9449 | 25.86035 |
| 5.1025 | 34.45457 | 32.90160 | 31.20029 | 28.9712 | 25.88043 |
| 5.105 | 34.49883 | 32.93964 | 31.2328 | 28.9975 | 25.90051 |
| 5.1075 | 34.54377 | 32.9768 | 31.26463 | 29.02638 | 25.92059 |
| 5.11 | 34.58802 | 33.01572 | 31.29715 | 29.0501 | 25.94067 |
| 5.1125 | 34.63297 | 33.05376 | 31.32966 | 29.07641 | 25.96145 |
| 5.115 | 34.67791 | 33.09180 | 31.36218 | 29.10271 | 25.98153 |
| 5.1175 | 34.72286 | 33.13053 | 31.39401 | 29.12901 | 26.00161 |
| 5.12 | 34.7678 | 33.6857 | 31.42652 | 29.15531 | 26.02169 |
| 5.1225 | 34.81344 | 33.20730 | 31.45904 | 29.1823 | 26.04178 |
| 5.125 | 34.85838 | 33.24603 | 31.49225 | 29.2085 | 26.06255 |
| 5.1275 | 34.90402 | 33.28476 | 31.52476 | 29.2349 | 26.08263 |
| 5.13 | 34.94965 | 33.32350 | 31.55728 | 29.26189 | 26.10272 |
| 5.1325 | 34.99598 | 33.36223 | 31.5898 | 29.28819 | 26.12349 |
| 5.135 | 35.04162 | 33.40096 | 31.62301 | 29.31519 | 26.14357 |
| 5.1375 | 35.08794 | 33.44038 | 31.65552 | 29.34149 | 26.16365 |
| 5.14 | 35.13427 | 33.47912 | 31.68873 | 29.36848 | 26.18443 |
| 5.1425 | 35.1806 | 33.51854 | 31.72194 | 29.39478 | 26.20451 |
| 5.145 | 35.22692 | 33.55796 | 31.75515 | 29.42177 | 26.22529 |
| 5.1475 | 35.27394 | 33.59738 | 31.78767 | 29.44877 | 26.24537 |
| 5.15 | 35.32027 | 33.63681 | 31.82088 | 29.47576 | 26.26614 |

APPENDIX 1-continued

Standard Mass Calculation

| Pressure | Temps | | | | |
|---|---|---|---|---|---|
| | 15.1 | 17.2 | 20.1 C. | 25.1 C. | 35.1 C. |
| 5.1525 | 35.36729 | 33.67623 | 31.85409 | 29.50206 | 26.28623 |
| 5.155 | 35.415 | 33.71566 | 31.88798 | 29.52905 | 26.307 |
| 5.1575 | 35.46201 | 33.75577 | 31.92119 | 29.55605 | 26.32709 |
| 5.16 | 35.50972 | 33.79519 | 31.9544 | 29.58304 | 26.34786 |
| 5.1625 | 35.55743 | 33.83531 | 31.9883 | 29.61003 | 26.36863 |
| 5.165 | 35.60514 | 33.87542 | 32.02151 | 29.63703 | 26.38872 |
| 5.1675 | 35.65285 | 33.91554 | 32.5541 | 29.66402 | 26.40949 |
| 5.17 | 35.70125 | 33.95565 | 32.08862 | 29.6917 | 26.42958 |
| 5.1725 | 35.74896 | 33.99646 | 32.12252 | 29.7189 | 26.45035 |
| 5.175 | 35.79736 | 34.03657 | 32.15642 | 29.74569 | 26.47113 |
| 5.1775 | 35.84645 | 34.07738 | 32.19032 | 29.77269 | 26.4919 |
| 5.18 | 35.89485 | 34.11818 | 32.22422 | 29.80037 | 26.51199 |
| 5.1825 | 35.94394 | 34.15899 | 32.25813 | 29.82736 | 26.53278 |
| 5.185 | 35.99303 | 34.19980 | 32.29203 | 29.35505 | 26.55354 |
| 5.1875 | 36.04212 | 34.24060 | 32.32593 | 29.88204 | 26.57431 |
| 5.19 | 36.0919 | 34.28141 | 32.36052 | 29.90973 | 26.59509 |
| 5.1925 | 36.141 | 34.32291 | 32.39442 | 29.93672 | 26.61517 |
| 5.195 | 36.19078 | 34.36371 | 32.42901 | 29.96441 | 26.63595 |
| 5.1975 | 36.24056 | 34.40521 | 32.46292 | 29.99209 | 26.65673 |
| 5.2 | 36.29103 | 34.44671 | 32.49751 | 30.01909 | 26.6775 |
| 5.2025 | 36.34151 | 34.48821 | 32.5321 | 30.04677 | 26.69828 |
| 5.205 | 36.39198 | 34.53039 | 32.56569 | 30.07445 | 26.71905 |
| 5.2075 | 36.44245 | 34.57189 | 32.60128 | 30.10215 | 26.73983 |
| 5.21 | 36.49293 | 34.61408 | 32.63588 | 30.12983 | 26.76061 |
| 5.2125 | 36.54409 | 34.65627 | 32.67047 | 30.15752 | 26.78138 |
| 5.215 | 36.59525 | 34.69777 | 32.70506 | 30.1852 | 26.80216 |
| 5.2175 | 36.64711 | 34.74065 | 32.74035 | 30.21289 | 26.82294 |
| 5.22 | 36.69827 | 34.78284 | 32.77494 | 30.24058 | 26.8444 |
| 5.2225 | 36.75013 | 34.82503 | 32.81022 | 30.26895 | 26.86518 |
| 5.225 | 36.30198 | 34.86791 | 32.34482 | 30.29664 | 26.83596 |
| 5.2275 | 36.85453 | 34.91010 | 32.8801 | 30.32433 | 26.903673 |
| 5.23 | 36.90639 | 34.95298 | 32.91539 | 30.3527 | 26.92751 |
| 5.2325 | 36.95893 | 34.99586 | 32.95067 | 30.38039 | 26.94898 |
| 5.235 | 37.01148 | 35.03943 | 32.98596 | 30.40808 | 26.96975 |
| 5.2375 | 37.06472 | 35.08231 | 33.02124 | 30.43645 | 26.99053 |
| 5.24 | 37.11795 | 35.12588 | 33.05722 | 30.46414 | 27.01131 |
| 5.2425 | 37.17119 | 35.16876 | 33.0925 | 30.49252 | 27.03278 |
| 5.245 | 37.22512 | 35.21233 | 33.12779 | 30.5209 | 27.05355 |
| 5.2475 | 37.27835 | 35.25591 | 33.16376 | 30.54928 | 27.07433 |
| 5.25 | 37.33228 | 35.30017 | 33.19974 | 30.57696 | 27.0958 |
| 5.2525 | 37.3869 | 35.34374 | 33.23502 | 30.60534 | 27.11658 |
| 5.255 | 37.44083 | 35.38800 | 33.271 | 30.63372 | 27.13805 |
| 5.2575 | 37.49545 | 35.43157 | 33.30698 | 30.6621 | 27.15883 |
| 5.26 | 37.55076 | 35.47584 | 33.34295 | 30.69048 | 27.18029 |
| 5.2625 | 37.60538 | 35.52079 | 33.37893 | 30.71886 | 27.20107 |
| 5.265 | 37.66069 | 35.56505 | 33.4156 | 30.74724 | 27.22254 |
| 5.2675 | 37.71669 | 35.60932 | 33.45157 | 30.77561 | 27.24332 |
| 5.27 | 37.772 | 35.65427 | 33.48824 | 30.80458 | 27.26479 |
| 5.2725 | 37.828 | 35.69923 | 33.52422 | 30.83306 | 27.28557 |
| 5.275 | 37.884 | 35.74418 | 33.56089 | 30.86144 | 27.30704 |
| 5.2775 | 37.94069 | 35.78914 | 33.59756 | 30.89051 | 27.32851 |
| 5.28 | 37.99738 | 35.83478 | 33.63422 | 30.91889 | 27.34928 |
| 5.2825 | 38.05408 | 35.87974 | 33.67089 | 30.94727 | 27.37075 |
| 5.285 | 38.11146 | 35.92538 | 33.70756 | 30.97634 | 27.39222 |
| 5.2875 | 38.16884 | 35.97103 | 33.74423 | 31.00541 | 27.41369 |
| 5.29 | 38.22622 | 36.01667 | 33.7809 | 31.03379 | 27.43447 |
| 5.2925 | 38.2843 | 36.06301 | 33.81826 | 31.06286 | 27.45594 |
| 5.295 | 38.34237 | 36.10866 | 33.85493 | 31.09193 | 27.47741 |
| 5.2975 | 38.40114 | 36.15499 | 33.89229 | 31.12101 | 27.49888 |
| 5.3 | 38.4599 | 36.20133 | 33.92965 | 31.14939 | 27.52035 |
| 5.3025 | 38.51867 | 36.24767 | 33.96701 | 31.17846 | 27.54182 |
| 5.305 | 38.57812 | 36.29469 | 34.00437 | 31.20753 | 27.56329 |
| 5.3075 | 38.63758 | 36.34103 | 34.04173 | 31.2366 | 27.58476 |
| 5.31 | 38.69703 | 36.38806 | 34.07909 | 31.26567 | 27.60623 |
| 5.3125 | 38.75718 | 36.43509 | 34.11645 | 31.29543 | 27.6277 |
| 5.315 | 38.81732 | 36.48281 | 34.1545 | 31.32451 | 27.64917 |
| 5.3175 | 38.87816 | 36.52983 | 34.19255 | 31.35358 | 27.87065 |
| 5.32 | 38.939 | 36.57755 | 34.22991 | 31.38255 | 27.69212 |
| 5.3225 | 38.99984 | 36.62527 | 34.26796 | 31.41241 | 27.71359 |
| 5.325 | 39.06136 | 36.67299 | 34.30601 | 31.44149 | 27.73506 |
| 5.3275 | 39.12289 | 36.72071 | 34.34407 | 31.47125 | 27.75653 |
| 5.33 | 39.18511 | 36.76843 | 34.38212 | 31.50032 | 27.778 |
| 5.3325 | 39.24733 | 36.81684 | 34.42017 | 31.53008 | 27.79947 |
| 5.335 | 39.30955 | 36.86525 | 34.45891 | 31.55985 | 27.82163 |

APPENDIX 1-continued

Standard Mass Calculation

| Pressure | Temps | | | | |
|---|---|---|---|---|---|
| | 15.1 | 17.2 | 20.1 C. | 25.1 C. | 35.1 C. |
| 5.3375 | 39.37246 | 36.91366 | 34.49696 | 31.58892 | 27.84311 |
| 5.34 | 39.43606 | 36.96277 | 34.53571 | 31.61868 | 27.86458 |
| 5.3425 | 39.49966 | 37.01118 | 34.57445 | 31.64845 | 27.88605 |
| 5.345 | 39.56326 | 37.06028 | 34.61319 | 31.67821 | 27.90821 |
| 5.3475 | 39.62755 | 37.10938 | 34.65194 | 31.70798 | 27.92968 |
| 5.35 | 39.69184 | 37.15917 | 34.69068 | 31.73774. | 27.95116 |
| 5.3525 | 39.75683 | 37.20828 | 34.72943 | 31.7675 | 27.97332 |
| 5.355 | 39.82181 | 37.25807 | 34.76817 | 31.79727 | 27.99479 |
| 5.3575 | 39.88748 | 37.30786 | 34.8076 | 31.82772 | 28.01695 |
| 5.36 | 39.95315 | 37.35765 | 34.84635 | 31.85749 | 28.03843 |
| 5.3625 | 40.01952 | 37.40814 | 34.88578 | 31.88725 | 28.06059 |
| 5.365 | 40.08588 | 37.45862 | 34.92522 | 31.91771 | 28.08206 |
| 5.3675 | 40.15294 | 37.50911 | 34.96465 | 31.94747 | 28.10423 |
| 5.37 | 40.21999 | 37.55959 | 35.00409 | 31.97793 | 28.1257 |
| 5.3725 | 40.28774 | 37.61008 | 35.04353 | 32.00769 | 28.14786 |
| 5.375 | 40.35617 | 37.66125 | 35.08365 | 32.03815 | 28.16934 |
| 5.3775 | 40.42461 | 37.71243 | 35.12309 | 32.06861 | 28.1915 |
| 5.38 | 40.49304 | 37.76360 | 35.16321 | 32.09837 | 28.21366 |
| 5.3825 | 40.56217 | 37.81547 | 35.20334 | 32.12883 | 28.23514 |
| 5.385 | 40.63199 | 37.86734 | 35.24347 | 32.15928 | 28.2573 |
| 5.3875 | 40.70181 | 37.91920 | 35.28359 | 32.18974 | 28.27946 |
| 5.39 | 40.77232 | 37.97107 | 35.32372 | 32.2202 | 28.30163 |
| 5.3925 | 40.84282 | 38.02363 | 35.36385 | 32.25065 | 28.3231 |
| 5.395 | 40.91402 | 38.07549 | 35.40467 | 32.28111 | 28.34527 |
| 5.3975 | 40.98522 | 38.12874 | 35.4448 | 32.31157 | 28.36743 |
| 5.4 | 41.0578 | 38.18130 | 35.48561 | 32.34272 | 28.3896 |
| 5.4025 | 41.12969 | 38.23455 | 35.52643 | 32.37317 | 28.41176 |
| 5.405 | 41.20296 | 38.28780 | 35.56725 | 32.40432 | 28.43392 |
| 5.4075 | 41.27624 | 38.34105 | 35.60807 | 32.43478 | 28.45609 |
| 5.41 | 41.3502 | 38.39430 | 35.64889 | 32.46593 | 28.47825 |
| 5.4125 | 41.42476 | 38.44824 | 35.6904 | 32.49639 | 28.50042 |
| 5.415 | 41.49881 | 38.50218 | 35.73122 | 32.52753 | 28.52258 |
| 5.4175 | 41.57416 | 38.55681 | 35.77273 | 32.55868 | 28.54475 |
| 5.42 | 41.6495 | 38.61075 | 35.81424 | 32.58914 | 28.56691 |
| 5.4225 | 41.72623 | 38.66538 | 35.85575 | 32.62029 | 28.58908 |
| 5.425 | 41.80226 | 38.72070 | 35.89726 | 32.85144 | 28.61125 |
| 5.4275 | 41.87968 | 38.77533 | 35.93877 | 32.68259 | 28.63341 |
| 5.43 | 41.95709 | 38.83065 | 35.98097 | 32.71374 | 28.65627 |
| 5.4325 | 42.03589 | 38.88598 | 36.02248 | 32.74489 | 28.67843 |
| 5.435 | 42.114 | 38.94199 | 36.06468 | 32.77673 | 28.7006 |
| 5.4375 | 42.19349 | 38.99800 | 36.10688 | 32.80788 | 28.72277 |
| 5.44 | 42.27366 | 39.05402 | 36.14909 | 32.83903 | 28.74562 |
| 5.4425 | 42.35384 | 39.11003 | 36.19129 | 32.87087 | 28.76779 |
| 5.445 | 42.43471 | 39.16673 | 36.23349 | 32.90202 | 28.78995 |
| 5.4475 | 42.51627 | 39.22344 | 36.27638 | 32.93386 | 28.81281 |
| 5.45 | 42.59852 | 39.28014 | 36.31859 | 32.96501 | 28.83498 |
| 5.4525 | 42.68077 | 39.33754 | 36.36148 | 32.99685 | 28.85715 |
| 5.455 | 42.76441 | 39.39493 | 36.40437 | 33.02869 | 28.88 |
| 5.4575 | 42.84804 | 39.45302 | 36.44727 | 33.05984 | 28.90217 |
| 5.46 | 42.93236 | 39.51111 | 36.49016 | 33.09168 | 28.92503 |
| 5.4625 | 43.01807 | 39.56919 | 36.53375 | 33.12352 | 28.94719 |
| 5.465 | 43.10377 | 39.62728 | 36.57664 | 33.15537 | 28.97005 |
| 5.4675 | 43.19017 | 39.68606 | 36.62022 | 33.18721 | 28.99291 |
| 5.47 | 43.27725 | 39.74484 | 36.66381 | 33.21974 | 29.01508 |
| 5.4725 | 43.36503 | 39.80430 | 36.70739 | 33.25158 | 29.03793 |
| 5.475 | 43.45418 | 39.86377 | 36.75098 | 33.28342 | 29.06079 |
| 5.4775 | 43.54334 | 39.92324 | 36.79457 | 33.31527 | 29.08296 |
| 5.48 | 43.63319 | 39.98271 | 36.83884 | 33.3478 | 29.10582 |
| 5.4825 | 43.72373 | 40.04287 | 36.88312 | 33.37964 | 29.12868 |
| 5.485 | 43.81565 | 40.10372 | 36.9267 | 33.41218 | 29.15154 |
| 5.4875 | 43.90826 | 40.16457 | 36.97098 | 33.44471 | 29.1737 |
| 5.49 | 44.00087 | 40.22542 | 37.01595 | 33.47655 | 29.19656 |
| 5.4925 | 44.09486 | 40.28627 | 37.06023 | 33.50909 | 29.21942 |
| 5.495 | 44.18955 | 40.34782 | 37.10519 | 33.54162 | 29.24228 |
| 5.4975 | 44.28561 | 40.41005 | 37.14947 | 33.57415 | 29.26514 |
| 5.5 | 44.38167 | 40.47159 | 37.19444 | 33.60669 | 29.288 |
| 5.5025 | 44.47912 | 40.53451 | 37.23941 | 33.63922 | 29.31086 |
| 5.505 | 44.57794 | 40.59675 | 37.28438 | 33.67176 | 29.33372 |
| 5.5075 | 44.67677 | 40.65967 | 37.33003 | 33.70498 | 29.35658 |
| 5.51 | 44.77698 | 40.72260 | 37.375 | 33.73752 | 29.37944 |
| 5.5125 | 44.87857 | 40.78621 | 37.42066 | 33.77005 | 29.40229 |
| 5.515 | 44.98016 | 40.85052 | 37.46632 | 33.80328 | 29.42515 |
| 5.5175 | 45.08382 | 40.91413 | 37.51198 | 33.83581 | 29.44801 |
| 5.52 | 45.18817 | 40.97844 | 37.55833 | 33.86904 | 28.47087 |
| 5.5225 | 45.29321 | 41.04343 | 37.60399 | 33.90226 | 29.49442 |
| 5.525 | 45.39963 | 41.10843 | 37.65034 | 33.9348 | 29.51729 |
| 5.5275 | 45.50744 | 41.17343 | 37.69601 | 33.96803 | 29.54015 |
| 5.53 | 45.61593 | 41.23912 | 37.74305 | 34.00125 | 29.56301 |
| 5.5325 | 45.72581 | 41.30549 | 37.7894 | 34.03448 | 29.58656 |
| 5.535 | 45.83706 | 41.37187 | 37.83575 | 34.06771 | 29.60942 |
| 5.5375 | 45.9497 | 41.43825 | 37.88279 | 34.10093 | 29.63297 |
| 5.54 | 46.06303 | 41.50532 | 37.92984 | 34.13485 | 29.65583 |
| 5.5425 | 46.17843 | 41.57239 | 37.97688 | 34.16808 | 29.67869 |
| 5.545 | 46.29452 | 41.64015 | 38.02392 | 34.20131 | 29.70224 |
| 5.5475 | 46.412 | 41.70791 | 38.07096 | 34.23522 | 29.7251 |
| 5.55 | 46.53154 | 41.77637 | 38.1187 | 34.26845 | 29.74865 |
| 5.5525 | 46.65246 | 41.84551 | 38.16574 | 34.30237 | 29.77152 |
| 5.555 | 46.77477 | 41.91465 | 38.21348 | 34.33629 | 29.79507 |
| 5.5575 | 46.89846 | 41.98379 | 38.2619 | 34.36952 | 29.31862 |
| 5.56 | 47.02422 | 42.05363 | 38.30964 | 34.40343 | 29.84148 |
| 5.5625 | 47.15136 | 42.12346 | 38.35806 | 34.43735 | 29.86503 |
| 5.565 | 47.28057 | 42.19399 | 38.4058 | 34.47127 | 29.88859 |
| 5.5675 | 47.41116 | 42.26520 | 38.45422 | 34.50519 | 29.91145 |
| 5.57 | 47.51382 | 42.33642 | 38.50265 | 34.5398 | 29.935 |
| 5.5725 | 47.67856 | 42.40832 | 38.55177 | 34.57372 | 29.95855 |
| 5.575 | 47.81537 | 42.48023 | 38.60019 | 34.60764 | 29.98211 |
| 5.5775 | 47.95425 | 42.55283 | 38.64931 | 34.64225 | 30.00497 |
| 5.58 | 48.0952 | 42.62542 | 38.69843 | 34.67617 | 30.02852 |
| 5.5825 | 48.23822 | 42.69940 | 38.74823 | 34.71078 | 30.05207 |
| 5.585 | 48.384 | 42.77269 | 38.79735 | 34.74539 | 30.07563 |
| 5.5875 | 48.53186 | 42.84667 | 38.84716 | 34.77931 | 30.09918 |
| 5.59 | 48.68247 | 42.92134 | 38.89697 | 34.81392 | 30.12273 |
| 5.5925 | 48.83585 | 42.99670 | 38.94678 | 34.84853 | 30.14629 |
| 5.595 | 48.99199 | 43.07206 | 38.99659 | 34.88315 | 30.16984 |
| 5.5975 | 49.1509 | 43.14811 | 39.04709 | 34.91776 | 30.19339 |
| 5.6 | 49.31325 | 43.22417 | 39.09758 | 34.95237 | 30.21695 |
| 5.6025 | 49.47837 | 43.30160 | 39.14809 | 34.98767 | 30.2405 |
| 5.605 | 49.64694 | 43.37903 | 39.19859 | 35.02228 | 30.26475 |
| 5.6075 | 49.31985 | 43.45647 | 39.24909 | 35.05639 | 30.2883 |
| 5.61 | 49.99513 | 43.534159 | 39.30028 | 35.0922 | 30.31186 |
| 5.6125 | 50.17544 | 43.61341 | 39.35147 | 35.1275 | 30.33541 |
| 5.615 | 50.3592 | 43.69291 | 39.40266 | 35.16211 | 30.35965 |
| 5.6175 | 50.54779 | 43.77242 | 39.45454 | 35.19742 | 30.38321 |
| 5.62 | 50.74053 | 43.85331 | 39.50574 | 35.23272 | 30.40676 |
| 5.6225 | 50.93879 | 43.93351 | 39.55762 | 35.26802 | 30.43101 |
| 5.625 | 51.14188 | 44.01508 | 39.6095 | 35.30333 | 30.45456 |
| 5.6275 | 51.35119 | 44.09735 | 39.66208 | 35.33863 | 30.47881 |
| 5.63 | 51.56602 | 44.17982 | 39.71396 | 35.37394 | 30.50237 |
| 5.6325 | 51.78776 | 44.26258 | 39.76653 | 35.40993 | 30.52661 |
| 5.635 | 52.01571 | 44.34624 | 39.81911 | 35.44523 | 30.55017 |
| 5.6375 | 52.25194 | 44.43058 | 39.87237 | 35.48123 | 30.57441 |
| 5.64 | 52.49646 | 44.51492 | 39.92495 | 35.51653 | 30.59797 |
| 5.6425 | 52.74995 | 44.60064 | 39.97822 | 35.55253 | 30.62221 |
| 5.645 | 53.01312 | 44.68637 | 40.03217 | 35.58852 | 30.64577 |
| 5.6475 | 53.28653 | 44.77278 | 40.08544 | 35.62452 | 30.67002 |
| 5.65 | 53.57258 | 44.85989 | 40.13939 | 35.66052 | 30.69426 |
| 5.6525 | 53.87233 | 44.94769 | 40.19335 | 35.69651 | 30.71851 |
| 5.655 | 54.18658 | 45.03617 | 40.24731 | 35.73251 | 30.74207 |
| 5.6575 | 54.5181 | 45.12535 | 40.30127 | 35.7685 | 30.76631 |
| 5.66 | 54.86963 | 45.21522 | 40.35592 | 35.8045 | 30.79056 |
| 5.6625 | 55.24395 | 45.30578 | 40.41056 | 35.84119 | 30.81481 |
| 5.665 | 55.64519 | 45.39634 | 40.4659 | 35.87719 | 30.83905 |
| 5.6675 | 98.754 | 45.48828 | 40.52055 | 35.91387 | 30.8633 |
| 5.67 | 99.03042 | 45.58091 | 40.57589 | 35.95056 | 30.88755 |
| 5.6725 | 99.29992 | 45.67424 | 40.63123 | 35.98725 | 30.9118 |
| 5.675 | 99.54873 | 45.76825 | 40.68726 | 36.02325 | 30.93604 |
| 5.6775 | 99.79062 | 45.86296 | 40.7426 | 36.05993 | 30.96029 |
| 5.68 | 100.0256 | 45.95904 | 40.79863 | 36.09731 | 30.98454 |
| 5.6825 | 100.2468 | 46.05513 | 40.85536 | 36.134 | 31.00879 |
| 5.685 | 100.4542 | 46.15260 | 40.91139 | 36.17069 | 31.03304 |
| 5.6875 | 100.6616 | 46.25076 | 40.96811 | 36.20738 | 31.05728 |
| 5.69 | 100.8552 | 46.34960 | 41.02483 | 36.24476 | 31.08222 |
| 5.6925 | 101.0487 | 46.44914 | 41.08225 | 36.28145 | 31.10647 |
| 5.695 | 101.2285 | 46.54938 | 41.13966 | 36.31883 | 31.13072 |
| 5.6975 | 101.4083 | 46.65099 | 41.19707 | 36.35621 | 31.15565 |
| 5.7 | 101.5812 | 46.75329 | 41.25449 | 36.39359 | 31.17991 |
| 5.7025 | 101.7471 | 46.85698 | 41.31259 | 36.43097 | 31.20416 |
| 5.705 | 101.9131 | 46.96135 | 41.3707 | 36.46835 | 31.2291 |

APPENDIX 1-continued

Standard Mass Calculation

| Pressure | 15.1 | 17.2 | 20.1 C. | 25.1 C. | 35.1 C. |
|---|---|---|---|---|---|
| 5.7075 | 102.0722 | 47.06642 | 41.4288 | 36.50573 | 31.25334 |
| 5.71 | 102.2243 | 47.17287 | 41.4876 | 36.54311 | 31.27828 |
| 5.7125 | 102.3765 | 47.28001 | 41.5464 | 36.58118 | 31.30253 |
| 5.715 | 102.5287 | 47.38784 | 41.60519 | 36.61856 | 31.32747 |
| 5.7175 | 102.667 | 47.49774 | 41.66468 | 36.65664 | 31.35172 |
| 5.72 | 102.8123 | 47.60764 | 41.72417 | 36.69471 | 31.37666 |
| 5.7225 | 102.9506 | 47.71961 | 41.78366 | 36.73209 | 31.4016 |
| 5.725 | 103.0821 | 47.83228 | 41.84384 | 36.77016 | 31.42585 |
| 5.7275 | 103.2136 | 47.94632 | 41.90402 | 36.80323 | 31.45079 |
| 5.73 | 103.345 | 48.06106 | 41.96489 | 36.84631 | 31.47574 |
| 5.7325 | 103.4696 | 48.17718 | 42.02507 | 36.88507 | 31.50068 |
| 5.735 | 103.5941 | 48.29537 | 42.08594 | 36.92314 | 31.52493 |
| 5.7375 | 103.7187 | 48.41425 | 42.1475 | 36.96122 | 31.54987 |
| 5.74 | 103.8363 | 48.53382 | 42.20906 | 36.99998 | 31.57481 |
| 5.7425 | 103.954 | 48.65547 | 42.27062 | 37.03875 | 31.59975 |
| 5.745 | 104.0716 | 48.77849 | 42.33218 | 37.07682 | 31.62469 |
| 5.7475 | 104.1824 | 48.90290 | 42.39443 | 37.11558 | 31.64963 |
| 5.75 | 104.3001 | 49.02869 | 42.45669 | 37.15435 | 31.67457 |
| 5.7525 | 104.4039 | 49.15555 | 42.51963 | 37.19311 | 31.69952 |
| 5.755 | 104.5147 | 49.28510 | 42.58258 | 37.23257 | 31.72446 |
| 5.7575 | 104.6185 | 49.41572 | 42.64552 | 37.27133 | 31.7494 |
| 5.76 | 104.7293 | 49.54773 | 42.70916 | 37.3101 | 31.77434 |
| 5.7625 | 104.8331 | 49.68181 | 42.77279 | 37.34956 | 31.79997 |
| 5.765 | 104.9301 | 49.81727 | 42.83712 | 37.38832 | 31.82492 |
| 5.7675 | 105.0339 | 49.95480 | 42.90144 | 37.42778 | 31.84986 |
| 5.77 | 105.1309 | 50.09440 | 42.96577 | 37.46724 | 31.8748 |
| 5.7725 | 105.2278 | 50.23538 | 43.03079 | 37.50669 | 31.90043 |
| 5.775 | 105.3247 | 50.37913 | 43.09581 | 37.54615 | 31.92538 |
| 5.7775 | 105.4217 | 50.52426 | 43.16152 | 37.58561 | 31.95032 |
| 5.78 | 105.5117 | 50.67146 | 43.22723 | 37.62575 | 31.97595 |
| 5.7825 | 105.6087 | 50.82142 | 43.29293 | 37.66521 | 32.0009 |
| 5.785 | 105.6987 | 50.97348 | 43.35934 | 37.70536 | 32.02653 |
| 5.7875 | 105.7888 | 51.12756 | 43.42574 | 37.74482 | 32.05147 |
| 5.79 | 105.8788 | 51.28443 | 43.9283 | 37.78497 | 32.07711 |
| 5.7925 | 105.9689 | 51.44337 | 43.55992 | 37.82512 | 32.10274 |
| 5.795 | 106.052 | 51.60577 | 43.6277 | 37.86527 | 32.12769 |
| 5.7975 | 106.1421 | 51.77024 | 43.69548 | 37.90542 | 32.15332 |
| 5.8 | 106.2252 | 51.93816 | 43.76327 | 37.94556 | 32.17895 |
| 5.8025 | 106.3084 | 52.10815 | 43.83174 | 37.9864 | 32.2039 |
| 5.805 | 106.3915 | 52.28228 | 43.90091 | 38.02655 | 32.22953 |
| 5.8075 | 106.4746 | 52.45918 | 43.96938 | 38.0674 | 32.25517 |
| 5.81 | 106.5578 | 52.63953 | 44.03924 | 38.10824 | 32.2808 |
| 5.8125 | 106.634 | 52.82334 | 44.10909 | 38.14839 | 32.30644 |
| 5.815 | 106.7172 | 53.01060 | 44.17895 | 38.18923 | 32.33207 |
| 5.8175 | 106.7934 | 53.20200 | 44.2495 | 38.23076 | 32.35702 |
| 5.82 | 106.8766 | 53.39755 | 44.32005 | 38.2716 | 32.38265 |
| 5.8225 | 106.9528 | 53.59654 | 44.39128 | 38.31244 | 32.40898 |
| 5.825 | 107.0291 | 53.80107 | 44.46252 | 38.35398 | 32.43462 |
| 5.8275 | 107.1053 | 54.00974 | 44.53445 | 38.39482 | 32.46025 |
| 5.83 | 107.1815 | 54.22393 | 44.60638 | 38.43635 | 32.48589 |
| 5.8325 | 107.2509 | 54.44296 | 44.679 | 38.47788 | 32.51152 |
| 5.835 | 107.3271 | 54.66751 | 44.75232 | 38.51942 | 32.53716 |
| 5.8375 | 107.3965 | 54.89828 | 44.82563 | 38.56095 | 32.5628 |
| 5.84 | 107.4727 | 55.13457 | 44.89894 | 38.60248 | 32.58912 |
| 5.8425 | 107.542 | 55.37846 | 44.97295 | 38.64471 | 32.61476 |
| 5.845 | 107.6114 | 55.62856 | 45.04764 | 38.68624 | 32.6404 |
| 5.8475 | 107.6807 | 55.88696 | 45.12233 | 38.72847 | 32.66672 |
| 5.85 | 107.757 | 56.15363 | 45.19772 | 38.77 | 32.69236 |
| 5.8525 | 107.8263 | 56.42860 | 45.27311 | 38.81223 | 32.71869 |
| 5.855 | 107.8888 | 56.71255 | 45.34918 | 38.85445 | 32.74432 |
| 5.8575 | 107.9581 | 57.00754 | 45.42526 | 38.89668 | 32.77065 |
| 5.86 | 108.0274 | 57.31289 | 45.50203 | 38.93959 | 32.79629 |
| 5.8625 | 108.0968 | 57.63067 | 45.57949 | 38.98182 | 32.82262 |
| 5.865 | 108.1592 | 57.96158 | 45.65695 | 39.02474 | 32.84825 |
| 5.8675 | 108.2286 | 58.30698 | 45.7351 | 39.06696 | 32.87458 |
| 5.87 | 108.291 | 58.66827 | 45.81394 | 39.10988 | 32.90091 |
| 5.8725 | 108.3534 | 59.04683 | 45.89278 | 39.1528 | 32.92724 |
| 5.875 | 108.4228 | 59.44541 | 45.97231 | 39.19572 | 32.96288 |
| 5.8775 | 108.4852 | 59.88540 | 46.05185 | 39.23932 | 32.97921 |
| 5.88 | 108.5477 | 60.31094 | 46.13207 | 39.28224 | 33.00554 |
| 5.8825 | 108.6101 | 60.78479 | 46.21299 | 39.32516 | 33.03186 |
| 5.885 | 108.6726 | 61.29179 | 46.2939 | 39.36877 | 33.05819 |
| 5.8875 | 108.735 | 61.83608 | 46.37551 | 39.41238 | 33.08452 |
| 5.89 | 108.7974 | 62.42526 | 46.4578 | 39.45599 | 33.11085 |
| 5.8925 | 108.853 | 63.06830 | 46.54079 | 39.4996 | 33.13718 |
| 5.895 | 108.9154 | 63.77556 | 46.62378 | 39.54321 | 33.16351 |
| 5.8975 | 108.9779 | 64.56362 | 46.70746 | 39.58682 | 33.18984 |
| 5.9 | 109.0334 | 65.45180 | 46.79183 | 39.63112 | 33.21617 |
| 5.9025 | 109.0958 | 66.47188 | 46.8762 | 39.67542 | 33.24319 |
| 5.905 | 109.1514 | 67.66460 | 46.96126 | 39.71903 | 33.26952 |
| 5.9075 | 109.2138 | 69.09418 | 47.04702 | 39.76333 | 33.29585 |
| 5.91 | 109.2694 | 70.83450 | 47.13346 | 39.80763 | 33.32287 |
| 5.9125 | 109.3249 | 72.96152 | 47.2199 | 39.85263 | 33.3492 |
| 5.915 | 109.3804 | 75.43383 | 47.30773 | 39.89693 | 33.37653 |
| 5.9175 | 109.4429 | 77.95449 | 47.39556 | 39.94192 | 33.40256 |
| 5.92 | 109.4984 | 80.22657 | 47.48407 | 39.98622 | 33.42889 |
| 5.9225 | 109.554 | 82.13267 | 47.57259 | 40.03122 | 33.45591 |
| 5.925 | 109.6095 | 83.70042 | 47.66249 | 40.07621 | 33.48224 |
| 5.9275 | 109.665 | 85.01958 | 47.75239 | 40.1212 | 33.50926 |
| 5.93 | 109.7206 | 86.13159 | 47.84367 | 40.16689 | 33.53559 |
| 5.9325 | 109.7761 | 87.09859 | 47.93495 | 40.21188 | 33.56261 |
| 5.935 | 109.8248 | 87.94129 | 48.02692 | 40.25757 | 33.58964 |
| 5.9375 | 109.8803 | 88.69423 | 48.11959 | 40.30256 | 33.61666 |
| 5.94 | 109.9358 | 89.37121 | 48.21294 | 40.34825 | 33.64299 |
| 5.9425 | 109.9845 | 89.98604 | 48.30699 | 40.39393 | 33.67001 |
| 5.945 | 110.04 | 90.54563 | 48.40172 | 40.44031 | 33.69704 |
| 5.9475 | 110.0956 | 91.06380 | 48.49646 | 40.486 | 33.72406 |
| 5.95 | 110.1442 | 91.54744 | 48.59258 | 40.53237 | 33.75108 |
| 5.9525 | 110.1997 | 91.99655 | 48.68939 | 40.57806 | 33.7781 |
| 5.955 | 110.2484 | 92.41804 | 48.7862 | 40.62444 | 33.80513 |
| 5.9575 | 110.3039 | 92.81191 | 48.88439 | 40.67081 | 33.83215 |
| 5.96 | 110.3526 | 93.18507 | 48.98328 | 40.71719 | 33.85917 |
| 5.9625 | 110.4012 | 93.53751 | 49.08285 | 40.76426 | 33.8862 |
| 5.965 | 110.4498 | 93.87614 | 49.18311 | 40.81064 | 33.91391 |
| 5.9675 | 110.5054 | 94.19406 | 49.28407 | 40.85771 | 33.94094 |
| 5.97 | 110.564 | 94.50507 | 49.38572 | 40.90478 | 33.96796 |
| 5.9726 | 110.6027 | 94.79537 | 49.48806 | 40.95185 | 33.99498 |
| 5.975 | 110.6513 | 95.07876 | 49.59178 | 40.99892 | 34.0227 |
| 5.9775 | 110.6999 | 95.34834 | 49.6955 | 41.04599 | 34.04972 |
| 5.98 | 110.7486 | 95.60411 | 49.8006 | 41.09375 | 34.07744 |
| 5.9825 | 110.7972 | 95.85989 | 49.90639 | 41.14151 | 34.10446 |
| 5.985 | 110.8458 | 96.10185 | 50.01288 | 41.18927 | 34.13218 |
| 5.9875 | 110.8945 | 96.33000 | 50.12074 | 41.23703 | 34.1592 |
| 5.99 | 110.9431 | 96.55816 | 50.2293 | 41.28479 | 34.18692 |
| 5.9925 | 110.9918 | 96.77941 | 50.33855 | 41.33258 | 34.21394 |
| 5.995 | 111.0404 | 96.99375 | 50.44849 | 41.38101 | 34.24166 |
| 5.9975 | 111.0821 | 97.20119 | 50.55981 | 41.42946 | 34.26938 |
| 6 | 111.1308 | 97.40173 | 50.67183 | 41.47722 | 34.2964 |
| 6.0025 | 111.1794 | 97.59536 | 50.78453 | 41.52637 | 34.32412 |
| 6.005 | 111.2212 | 97.78899 | 50.89861 | 41.57482 | 34.35183 |
| 6.0075 | 111.2698 | 97.96881 | 51.01408 | 41.62323 | 34.37955 |
| 6.01 | 111.3184 | 98.15553 | 51.13024 | 41.67242 | 34.40727 |
| 6.0125 | 111.3602 | 98.32845 | 51.24709 | 41.72157 | 34.43498 |
| 6.015 | 111.4088 | 98.50136 | 51.36532 | 41.77071 | 34.4627 |
| 6.0175 | 111.4506 | 98.66738 | 51.48425 | 41.81986 | 34.49042 |
| 6.02 | 111.4992 | 98.83339 | 51.60455 | 41.869 | 34.51814 |
| 6.0225 | 111.5409 | 98.99940 | 51.72624 | 41.91884 | 34.54586 |
| 6.025 | 111.5827 | 99.15160 | 51.84931 | 41.96868 | 34.57357 |
| 6.0275 | 111.6313 | 99.31071 | 51.97307 | 42.01851 | 34.60198 |
| 6.03 | 111.6731 | 99.46291 | 52.09752 | 42.06835 | 34.6297 |
| 6.0325 | 111.7148 | 99.60821 | 52.22404 | 42.11819 | 34.65741 |
| 6.035 | 111.7634 | 99.75351 | 52.35125 | 42.16872 | 34.68582 |
| 6.0375 | 111.8052 | 99.89881 | 52.48054 | 42.21855 | 34.71354 |
| 6.04 | 111.8469 | 100.03720 | 52.61052 | 42.26908 | 34.74126 |
| 6.0425 | 111.8886 | 100.17559 | 52.74188 | 42.31961 | 34.76967 |
| 6.045 | 111.9373 | 100.31399 | 52.87462 | 42.37083 | 34.79739 |
| 6.0476 | 111.979 | 100.44548 | 53.00875 | 42.42136 | 34.82586 |
| 6.05 | 112.0208 | 100.57697 | 53.14425 | 42.47258 | 34.8542 |
| 6.0525 | 112.0625 | 100.70155 | 53.28114 | 42.5238 | 34.88192 |
| 6.055 | 112.1042 | 100.83304 | 53.41941 | 42.57503 | 34.91033 |
| 6.0575 | 112.146 | 100.95763 | 53.55976 | 42.62625 | 34.93874 |
| 6.06 | 112.1877 | 101.07531 | 53.70079 | 42.67816 | 34.96715 |
| 6.0625 | 112.2295 | 101.19989 | 53.8439 | 42.73007 | 34.99487 |
| 6.065 | 112.2712 | 101.31758 | 53.95908 | 42.78129 | 35.02323 |
| 6.0675 | 112.3129 | 101.43526 | 54.13564 | 42.8339 | 35.05169 |
| 6.07 | 112.3547 | 101.55294 | 54.28358 | 42.88581 | 35.0801 |
| 6.0725 | 112.3964 | 101.66371 | 54.4336 | 42.93842 | 35.10851 |
| 6.075 | 112.4313 | 101.77449 | 54.585 | 42.99033 | 35.13692 |

APPENDIX 1-continued

Standard Mass Calculation

| Pressure | Temps | | | | |
|---|---|---|---|---|---|
| | 15.1 | 17.2 | 20.1 C. | 25.1 C. | 35.1 C. |
| 6.0775 | 112.473 | 101.88527 | 54.73847 | 43.04293 | 35.16534 |
| 6.08 | 112.5147 | 101.99605 | 54.89401 | 43.09554 | 35.19375 |
| 6.0825 | 112.5565 | 102.09992 | 55.05094 | 43.14884 | 35.22285 |
| 6.085 | 112.5982 | 102.21070 | 55.21063 | 43.20144 | 35.25126 |
| 6.0875 | 112.633 | 102.31457 | 55.3717 | 43.25474 | 35.27967 |
| 6.09 | 112.6748 | 102.41844 | 55.53484 | 43.30803 | 35.30808 |
| 6.0925 | 112.7165 | 102.52231 | 55.70006 | 43.36202 | 35.33718 |
| 6.095 | 112.7514 | 102.61928 | 55.86804 | 43.41532 | 35.3656 |
| 6.0975 | 112.7931 | 102.72316 | 56.0381 | 43.46931 | 35.3947 |
| 6.1 | 112.8279 | 102.82012 | 56.21022 | 43.5233 | 36.42311 |
| 6.1025 | 112.8697 | 102.91709 | 56.38442 | 43.67728 | 35.45221 |
| 6.105 | 112.9114 | 103.01406 | 56.56139 | 43.63127 | 35.48063 |
| 6.1075 | 112.9463 | 103.11103 | 56.74111 | 43.68595 | 35.50973 |
| 6.11 | 112.988 | 103.20110 | 56.92291 | 43.74063 | 35.53883 |
| 6.1125 | 113.0228 | 103.29807 | 57.10748 | 43.79531 | 35.56725 |
| 6.115 | 113.0646 | 103.38813 | 57.2948 | 43.84999 | 35.59635 |
| 6.1175 | 113.0994 | 103.47820 | 57.48489 | 43.90537 | 35.62545 |
| 6.12 | 113.1343 | 103.56828 | 57.67775 | 43.96074 | 35.65456 |
| 6.1225 | 113.176 | 103.65833 | 57.87337 | 44.01611 | 35.68366 |
| 6.125 | 113.2108 | 103.74148 | 58.07244 | 44.07148 | 35.71276 |
| 6.1275 | 113.2528 | 103.83155 | 58.27428 | 44.12755 | 35.74187 |
| 6.13 | 113.2874 | 103.92162 | 58.47957 | 44.18292 | 35.77097 |
| 6.1325 | 113.3222 | 104.00478 | 58.68762 | 44.23898 | 35.80008 |
| 6.135 | 113.364 | 104.08794 | 58.89982 | 44.29574 | 35.82918 |
| 6.1375 | 113.3988 | 104.17110 | 59.11479 | 44.3518 | 35.85829 |
| 6.14 | 113.4337 | 104.25426 | 59.33389 | 44.40856 | 35.88739 |
| 6.1425 | 113.4685 | 104.33742 | 59.55646 | 44.46531 | 35.91719 |
| 6.145 | 113.5102 | 104.42059 | 59.78248 | 44.52207 | 35.94629 |
| 6.1475 | 113.5451 | 104.49684 | 60.01264 | 44.57952 | 35.9754 |
| 6.15 | 113.5799 | 104.58000 | 60.24695 | 44.63627 | 36.00519 |
| 6.1525 | 113.6148 | 104.65626 | 60.48541 | 44.69372 | 36.0343 |
| 6.155 | 113.6496 | 104.73942 | 60.72801 | 44.75186 | 36.0641 |
| 6.1575 | 113.6844 | 104.81568 | 60.97475 | 44.80931 | 36.0932 |
| 6.16 | 113.7262 | 104.89194 | 61.22633 | 44.86745 | 36.123 |
| 6.1625 | 113.761 | 104.96820 | 61.48275 | 44.92559 | 36.1528 |
| 6.165 | 113.7959 | 105.04445 | 61.74332 | 44.98373 | 36.1819 |
| 6.1675 | 113.8307 | 105.12071 | 62.00872 | 45.04256 | 36.2117 |
| 6.17 | 113.8655 | 105.19006 | 62.27965 | 45.10139 | 36.2415 |
| 6.1725 | 113.9004 | 105.26632 | 62.55541 | 45.16022 | 36.27129 |
| 6.175 | 113.9352 | 105.33568 | 62.83601 | 45.21905 | 36.30109 |
| 6.1775 | 113.97 | 105.41194 | 63.12214 | 45.27857 | 36.33089 |
| 6.18 | 114.0049 | 105.48129 | 63.41449 | 45.3381 | 36.36069 |
| 6.1825 | 114.0397 | 105.55755 | 63.71167 | 45.39762 | 36.39048 |
| 6.185 | 114.0746 | 105.62690 | 64.01507 | 45.45783 | 36.42028 |
| 6.1875 | 114.1094 | 105.69626 | 64.324 | 45.51805 | 36.45008 |
| 6.19 | 114.1373 | 105.76561 | 64.63914 | 45.57826 | 36.47988 |
| 6.1925 | 114.1722 | 105.83496 | 64.95982 | 45.63848 | 36.50968 |
| 6.195 | 114.207 | 105.90432 | 65.28671 | 45.69939 | 36.54017 |
| 6.1975 | 114.2419 | 105.97367 | 65.61982 | 45.76029 | 36.56997 |
| 6.2 | 114.2767 | 106.03612 | 65.95984 | 45.8212 | 36.60046 |
| 6.2025 | 114.3115 | 106.10548 | 66.30539 | 45.88211 | 36.63026 |
| 6.205 | 114.3464 | 106.17483 | 66.65716 | 45.9447 | 36.66005 |
| 6.2075 | 114.3743 | 106.23728 | 67.01583 | 46.0053 | 36.69054 |
| 6.21 | 114.4092 | 106.30664 | 67.38004 | 46.06759 | 36.72103 |
| 6.2125 | 114.444 | 106.36909 | 67.75115 | 46.12919 | 36.75083 |
| 6.215 | 114.4788 | 106.43154 | 68.12779 | 46.19148 | 36.78132 |
| 6.2175 | 114.5068 | 106.50089 | 68.51065 | 46.25446 | 36.81182 |
| 6.22 | 114.5416 | 106.56335 | 68.89904 | 46.31675 | 36.84231 |
| 6.2225 | 114.5764 | 106.62680 | 69.29019 | 46.37973 | 36.87211 |
| 6.225 | 114.6044 | 106.68825 | 69.69101 | 46.44341 | 36.9026 |
| 6.2275 | 114.6392 | 106.75070 | 70.09875 | 46.50639 | 36.93309 |
| 6.23 | 114.6741 | 106.81315 | 70.50649 | 46.57006 | 36.96358 |
| 6.2325 | 114.702 | 106.87560 | 70.92113 | 46.63374 | 36.99407 |
| 6.235 | 114.7368 | 106.93605 | 71.34269 | 46.6981 | 37.02456 |
| 6.2375 | 114.7717 | 106.99360 | 71.76425 | 46.76247 | 37.05575 |
| 6.24 | 114.7996 | 107.05605 | 72.18581 | 46.82683 | 37.08624 |
| 6.2425 | 114.8345 | 107.11850 | 72.62119 | 46.8912 | 37.11673 |
| 6.245 | 114.8624 | 107.17405 | 73.04966 | 46.95826 | 37.14722 |
| 6.2475 | 114.8972 | 107.23650 | 73.48505 | 47.022 | 37.17841 |
| 6.25 | 114.9252 | 107.29205 | 73.92043 | 47.08706 | 37.2089 |
| 6.2525 | 114.96 | 107.35450 | 74.35582 | 47.15281 | 37.24008 |
| 6.255 | 114.9879 | 107.41005 | 74.79121 | 47.21856 | 37.27057 |
| 6.2575 | 115.0228 | 107.46559 | 75.22661 | 47.285 | 37.30176 |
| 6.26 | 115.0507 | 107.52805 | 75.662 | 47.35075 | 37.33225 |
| 6.2625 | 115.0856 | 107.58359 | 76.0974 | 47.41788 | 37.36344 |
| 6.265 | 115.1135 | 107.63914 | 76.52589 | 47.48432 | 37.39462 |
| 6.2675 | 115.1483 | 107.69469 | 76.96129 | 47.55145 | 37.4258 |
| 6.27 | 115.1763 | 107.75024 | 77.38979 | 47.61928 | 37.4563 |
| 6.2725 | 115.2111 | 107.80576 | 77.81828 | 47.68641 | 37.48748 |
| 6.275 | 115.2391 | 107.86133 | 78.23988 | 47.75423 | 37.51867 |
| 6.2775 | 115.267 | 107.91688 | 78.65456 | 47.82275 | 37.54985 |
| 6.28 | 115.3018 | 107.97243 | 79.06925 | 47.89057 | 37.58104 |
| 6.2825 | 115.3298 | 108.02798 | 79.48394 | 47.95909 | 37.61222 |
| 6.285 | 115.3577 | 108.08353 | 79.39173 | 48.0283 | 37.6441 |
| 6.2875 | 115.3926 | 108.13217 | 80.29261 | 48.0975 | 37.67528 |
| 6.29 | 115.4205 | 108.18772 | 80.68658 | 48.16671 | 37.70647 |
| 6.2925 | 115.4484 | 108.24327 | 81.08056 | 48.23661 | 37.73766 |
| 6.295 | 115.4833 | 108.29191 | 81.46762 | 48.30651 | 37.76953 |
| 6.2975 | 115.5112 | 108.34746 | 81.84779 | 48.37641 | 37.80072 |
| 6.3 | 115.6391 | 108.39610 | 82.22104 | 48.447 | 37.8326 |
| 6.3025 | 115.5671 | 108.45165 | 82.58739 | 48.51759 | 37.86378 |
| 6.305 | 115.6019 | 108.50029 | 82.94684 | 48.58887 | 37.89566 |
| 6.3075 | 115.6299 | 108.55585 | 83.30628 | 48.66015 | 37.92685 |
| 6.31 | 115.6578 | 108.60449 | 83.65882 | 48.73144 | 37.95872 |
| 6.3125 | 115.6857 | 108.65313 | 84.00446 | 48.80341 | 37.9906 |
| 6.315 | 115.7206 | 108.70868 | 84.34318 | 48.87539 | 38.02248 |
| 6.3175 | 115.7485 | 108.75733 | 84.675 | 48.94736 | 38.05436 |
| 6.32 | 115.7765 | 108.80597 | 84.99992 | 49.02003 | 38.08624 |
| 6.3225 | 115.8044 | 108.85462 | 85.31792 | 49.09338 | 38.11811 |
| 6.325 | 115.8323 | 108.90326 | 85.63593 | 49.16674 | 38.14999 |
| 6.3275 | 115.8603 | 108.95881 | 85.94012 | 49.2401 | 38.18187 |
| 6.33 | 115.8951 | 109.00746 | 86.24432 | 49.31415 | 38.21375 |
| 6.3325 | 115.9231 | 109.05610 | 86.54161 | 49.3882 | 38.24563 |
| 6.335 | 115.951 | 109.10475 | 86.83199 | 49.46225 | 38.27751 |
| 6.3375 | 115.9789 | 109.15339 | 87.11546 | 49.53699 | 38.31008 |
| 6.34 | 116.0069 | 109.20204 | 87.39894 | 49.61242 | 38.34196 |
| 6.3425 | 116.0348 | 109.24378 | 87.6755 | 49.68786 | 38.37384 |
| 6.345 | 116.0627 | 109.29242 | 87.94517 | 49.76329 | 38.40641 |
| 6.3475 | 116.0907 | 109.34107 | 88.20792 | 49.83941 | 38.43829 |
| 6.35 | 116.1186 | 109.38971 | 88.47068 | 49.91553 | 38.47086 |
| 6.3525 | 116.1466 | 109.43836 | 88.72652 | 49.99235 | 38.50343 |
| 6.355 | 116.1745 | 109.48010 | 88.97547 | 50.06917 | 38.53531 |
| 6.3575 | 116.2024 | 109.52875 | 89.2176 | 50.14667 | 38.56788 |
| 6.36 | 116.2304 | 109.57739 | 89.45953 | 50.22418 | 38.60045 |
| 6.3625 | 116.2583 | 109.61913 | 89.69466 | 50.30169 | 38.63302 |
| 6.365 | 116.2863 | 109.66778 | 89.92979 | 50.37989 | 38.6656 |
| 6.3675 | 116.3142 | 109.71643 | 90.15801 | 50.45878 | 38.69817 |
| 6.37 | 116.3421 | 109.75817 | 90.37932 | 50.63767 | 38.73074 |
| 6.3725 | 116.3701 | 109.80681 | 90.60064 | 50.61656 | 38.76331 |
| 6.375 | 116.398 | 109.84855 | 90.81505 | 50.69614 | 38.79588 |
| 6.3775 | 116.426 | 109.89720 | 91.02945 | 50.77642 | 38.82915 |
| 6.38 | 116.4539 | 109.93894 | 91.23696 | 50.85669 | 38.86172 |
| 6.3825 | 116.4818 | 109.98068 | 91.43755 | 50.93697 | 38.89429 |
| 6.385 | 116.5098 | 110.02933 | 91.64505 | 51.01793 | 38.92756 |
| 6.3875 | 116.5377 | 110.07107 | 91.83874 | 51.09959 | 38.96013 |
| 6.39 | 116.5657 | 110.11281 | 92.03242 | 51.18125 | 38.99339 |
| 6.3925 | 116.5867 | 110.16146 | 92.22611 | 51.2636 | 39.02597 |
| 6.395 | 116.6146 | 110.20320 | 92.41289 | 51.34595 | 39.05923 |
| 6.3975 | 116.6426 | 110.24494 | 92.59967 | 51.4283 | 39.0925 |
| 6.4 | 116.6705 | 110.28668 | 92.77955 | 51.51134 | 39.12507 |
| 6.4025 | 116.6984 | 110.32843 | 92.95942 | 51.59507 | 39.15834 |
| 6.405 | 116.7264 | 110.37708 | 93.13929 | 51.6788 | 39.1916 |
| 6.4075 | 116.7474 | 110.41882 | 93.31226 | 51.76323 | 39.22487 |
| 6.41 | 116.7754 | 110.46056 | 93.47832 | 51.84834 | 39.25813 |
| 6.4125 | 116.8033 | 110.50230 | 93.65129 | 51.93277 | 39.2914 |
| 6.415 | 116.8312 | 110.54404 | 93.81735 | 52.01857 | 39.32466 |
| 6.4175 | 116.8592 | 110.58579 | 93.9765 | 52.10438 | 39.35862 |
| 6.42 | 116.8802 | 110.62753 | 94.14256 | 52.19088 | 39.39188 |
| 6.4225 | 116.9082 | 110.66927 | 94.29481 | 52.27738 | 39.42515 |
| 6.425 | 116.9361 | 110.71101 | 94.45396 | 52.36388 | 39.45911 |
| 6.4275 | 116.964. | 110.75276 | 94.60621 | 52.45176 | 39.49237 |
| 6.43 | 116.9851 | 110.79450 | 94.75845 | 52.53964 | 39.52633 |
| 6.4325 | 117.013 | 110.83624 | 94.9107 | 52.62753 | 39.5596 |
| 6.435 | 117.0409 | 110.87108 | 95.05604 | 52.7161 | 39.59356 |
| 6.4376 | 117.062 | 110.91282 | 95.20138 | 52.80536 | 39.62751 |
| 6.44 | 117.0899 | 110.95457 | 95.34672 | 52.89532 | 39.66078 |
| 6.4425 | 117.1179 | 110.99631 | 95.48515 | 52.98528 | 39.69474 |
| 6.445 | 117.1458 | 111.03805 | 95.6305 | 53.07524 | 39.7287 |

APPENDIX 1-continued

Standard Mass Calculation

| Pressure | 15.1 | 17.2 | 20.1 C. | 25.1 C. | 35.1 C. |
|---|---|---|---|---|---|
| 6.4475 | 117.1668 | 111.07289 | 95.76893 | 53.16589 | 39.76266 |
| 6.45 | 117.1948 | 111.11483 | 95.90046 | 53.25723 | 39.79662 |
| 6.4525 | 117.2227 | 111.15638 | 96.03889 | 53.34928 | 39.83058 |
| 6.455 | 117.2438 | 111.19121 | 96.17042 | 53.44129 | 39.86453 |
| 6.4575 | 117.2717 | 111.23296 | 96.30194 | 53.53401 | 39.89849 |
| 6.46 | 117.2927 | 111.27470 | 96.43347 | 53.62674 | 39.93314 |
| 6.4625 | 117.3207 | 111.30954 | 96.55809 | 53.72015 | 39.9671 |
| 6.465 | 117.3486 | 111.35129 | 96.68271 | 53.81426 | 40.00106 |
| 6.4675 | 117.3696 | 111.38612 | 96.80733 | 53.90837 | 40.03571 |
| 6.47 | 117.3976 | 111.42787 | 96.93195 | 54.00317 | 40.06967 |
| 6.4725 | 117.4186 | 111.46270 | 97.05657 | 54.09866 | 40.10433 |
| 6.475 | 117.4466 | 111.50445 | 97.17428 | 54.19484 | 40.13898 |
| 6.4776 | 117.4745 | 111.53929 | 97.292 | 54.29102 | 40.17294 |
| 6.48 | 117.4955 | 111.58103 | 97.40971 | 54.38789 | 40.20759 |
| 6.4825 | 117.5235 | 111.61587 | 97.52742 | 54.48477 | 40.24224 |
| 6.485 | 117.5445 | 111.65762 | 97.64514 | 54.58233 | 40.27689 |
| 6.4875 | 117.5725 | 111.69245 | 97.75594 | 54.68059 | 40.31154 |
| 6.49 | 117.6935 | 111.72729 | 97.87366 | 54.77954 | 40.3462 |
| 6.4925 | 117.6214 | 111.78904 | 97.98447 | 54.87918 | 40.38085 |
| 6.495 | 117.6425 | 111.80388 | 98.09527 | 54.97882 | 40.4155 |
| 6.4975 | 117.6704 | 111.83871 | 98.19917 | 55.07915 | 40.45085 |
| 6.5 | 117.6914 | 111.88046 | 98.30998 | 55.17948 | 40.4855 |
| 6.5025 | 117.7194 | 111.91530 | 98.41388 | 55.2812 | 40.52015 |
| 6.505 | 117.7404 | 111.95014 | 98.52469 | 55.38291 | 40.5555 |
| 6.5075 | 117.7684 | 111.99189 | 98.62859 | 55.48532 | 40.59015 |
| 6.51 | 117.7894 | 112.02672 | 98.73249 | 55.58773 | 40.62549 |
| 6.5125 | 117.8173 | 112.06156 | 98.83639 | 55.69151 | 40.66015 |
| 6.515 | 117.8384 | 112.09640 | 98.93338 | 55.7953 | 40.69549 |
| 6.5175 | 117.8663 | 112.13124 | 99.03728 | 55.89979 | 40.73084 |
| 6.52 | 117.8874 | 112.17299 | 99.13428 | 56.00496 | 40.76618 |
| 6.5225 | 117.9153 | 112.20783 | 99.23818 | 56.11082 | 40.80153 |
| 6.525 | 117.9363 | 112.24267 | 99.33517 | 56.21669 | 40.83687 |
| 6.5275 | 117.9574 | 112.27751 | 99.43217 | 56.32324 | 40.87222 |
| 6.53 | 117.9853 | 112.31235 | 99.52225 | 56.43049 | 40.90756 |
| 6.5325 | 118.0063 | 112.34718 | 99.61925 | 56.53843 | 40.94291 |
| 6.535 | 118.0343 | 112.38202 | 99.71624 | 56.64706 | 40.97826 |
| 6.5375 | 118.0553 | 112.41686 | 99.80633 | 56.75569 | 41.01429 |
| 6.54 | 118.0764 | 112.45170 | 99.90333 | 56.86571 | 41.04964 |
| 6.5426 | 118.1013 | 112.48654 | 99.99341 | 56.97572 | 41.08568 |
| 6.545 | 118.1253 | 112.52138 | 100.0835 | 57.08643 | 41.12102 |
| 6.5475 | 118.1533 | 112.55622 | 100.1736 | 57.19783 | 41.15706 |
| 6.55 | 118.1743 | 112.59107 | 100.2637 | 57.30992 | 41.19241 |
| 6.5525 | 118.1954 | 112.62591 | 100.3538 | 57.42201 | 41.22845 |
| 6.555 | 118.2233 | 112.66075 | 100.4369 | 57.53548 | 41.26449 |
| 6.5575 | 118.2443 | 112.69559 | 100.527 | 57.64895 | 41.30052 |
| 6.56 | 118.2654 | 112.73043 | 100.6102 | 57.76381 | 41.33656 |
| 6.5625 | 118.2933 | 112.76527 | 100.7003 | 57.87866 | 41.3726 |
| 6.565 | 118.3144 | 112.80011 | 100.7835 | 57.99421 | 41.40864 |
| 6.5675 | 118.3354 | 112.82804 | 100.8667 | 58.11045 | 41.44468 |
| 6.57 | 118.3633 | 112.86288 | 100.9498 | 58.22738 | 41.48072 |
| 6.5725 | 118.3844 | 112.89772 | 101.033 | 58.345 | 41.51745 |
| 6.575 | 118.4054 | 112.93257 | 101.1162 | 58.46332 | 41.55349 |
| 6.5775 | 118.4264 | 112.96741 | 101.1994 | 58.58163 | 41.59022 |
| 6.58 | 118.4544 | 112.99534 | 101.2757 | 58.70133 | 41.62626 |
| 6.5825 | 118.4754 | 113.03018 | 101.3588 | 58.82172 | 41.66299 |
| 6.585 | 118.4965 | 113.06502 | 101.4351 | 58.94211 | 41.69903 |
| 6.5875 | 118.5175 | 113.09987 | 101.5183 | 59.06388 | 41.73576 |
| 6.59 | 118.5454 | 113.12780 | 101.5946 | 59.18565 | 41.7725 |
| 6.5925 | 118.5665 | 113.16264 | 101.6709 | 59.30881 | 41.80923 |
| 6.595 | 118.5875 | 113.19748 | 101.754 | 59.43196 | 41.84596 |
| 6.5975 | 118.6085 | 113.22542 | 101.8303 | 59.55581 | 41.88269 |
| 6.6 | 118.6365 | 113.26026 | 101.9066 | 59.68104 | 41.91943 |
| 6.6025 | 118.6575 | 113.29510 | 101.9829 | 59.80627 | 41.95616 |
| 6.605 | 118.8786 | 113.32303 | 102.0522 | 59.93219 | 41.99289 |
| 6.6075 | 118.6996 | 113.35788 | 102.1285 | 60.0595 | 42.03031 |
| 6.61 | 118.7206 | 113.38581 | 102.2048 | 60.1868 | 42.06705 |
| 6.6125 | 118.7486 | 113.42065 | 102.2742 | 60.3148 | 42.10447 |
| 6.615 | 118.7696 | 113.45550 | 102.3504 | 60.44349 | 42.14121 |
| 6.6175 | 118.7907 | 113.48343 | 102.4198 | 60.57350 | 42.17863 |
| 6.62 | 118.8117 | 113.51827 | 102.4981 | 60.70363 | 42.21606 |
| 6.6225 | 118.8327 | 113.54621 | 102.5654 | 60.8344 | 42.25279 |
| 6.625 | 118.8607 | 113.58105 | 102.6348 | 60.96654 | 42.29021 |
| 6.6275 | 118.8317 | 113.60899 | 102.7042 | 61.09869 | 42.32764 |
| 6.63 | 118.9028 | 113.64383 | 102.7805 | 61.23222 | 42.36507 |
| 6.6325 | 118.9238 | 113.67176 | 102.8498 | 61.36575 | 42.40249 |
| 6.635 | 118.9448 | 113.70661 | 102.9192 | 61.49998 | 42.43992 |
| 6.6375 | 118.9659 | 113.73454 | 102.9817 | 61.63558 | 42.47803 |
| 6.64 | 118.9869 | 113.76939 | 103.051 | 61.77188 | 42.51546 |
| 6.6425 | 119.0148 | 113.79732 | 103.1204 | 61.90818 | 42.55289 |
| 6.645 | 119.0359 | 113.82528 | 103.1898 | 62.04586 | 42.591 |
| 6.6475 | 119.0569 | 113.86010 | 103.2522 | 62.18354 | 42.62843 |
| 6.65 | 119.078 | 113.88804 | 103.3216 | 62.3226 | 42.66655 |
| 6.6525 | 119.099 | 113.92288 | 103.3841 | 62.46236 | 42.70467 |
| 6.655 | 119.12 | 113.95081 | 103.4534 | 62.60211 | 42.74279 |
| 6.6575 | 119.1411 | 113.97875 | 103.5159 | 62.74325 | 42.78021 |
| 6.66 | 119.1621 | 114.01360 | 103.5853 | 62.88508 | 42.81833 |
| 6.6625 | 119.1831 | 114.04153 | 103.6477 | 63.02761 | 42.85645 |
| 6.665 | 119.2042 | 114.06947 | 103.7102 | 63.17082 | 42.89526 |
| 6.6675 | 119.2252 | 114.10431 | 103.7727 | 63.31473 | 42.93338 |
| 6.67 | 119.2463 | 114.13225 | 103.842 | 63.45933 | 42.9715 |
| 6.6725 | 119.2742 | 114.16018 | 103.9045 | 63.60462 | 43.00962 |
| 6.675 | 119.2952 | 114.19503 | 103.967 | 63.7506 | 43.04843 |
| 6.6775 | 119.3163 | 114.22296 | 104.0294 | 63.89727 | 43.08655 |
| 6.68 | 119.3373 | 114.25090 | 104.085 | 64.04464 | 43.12536 |
| 6.6825 | 119.3584 | 114.27883 | 104.1474 | 64.19269 | 43.16348 |
| 6.685 | 119.3794 | 114.31368 | 104.2099 | 64.34144 | 43.20229 |
| 6.6875 | 119.4004 | 114.34162 | 104.2724 | 64.49088 | 43.2411 |
| 6.69 | 119.4215 | 114.36955 | 104.3348 | 64.64102 | 43.27992 |
| 6.6925 | 119.4425 | 114.39749 | 104.3904 | 64.79184 | 43.31873 |
| 6.695 | 119.4635 | 114.42543 | 104.4529 | 64.94336 | 43.35754 |
| 6.6975 | 119.4846 | 114.46027 | 104.5084 | 65.09557 | 43.39635 |
| 6.7 | 119.5056 | 114.48821 | 104.5709 | 65.24847 | 43.43517 |
| 6.7025 | 119.5267 | 114.51615 | 104.6264 | 65.40206 | 43.47467 |
| 6.705 | 119.5477 | 114.54408 | 104.6889 | 65.55634 | 43.51348 |
| 6.7075 | 119.5687 | 114.57202 | 104.7445 | 65.71132 | 43.55299 |
| 6.71 | 119.5898 | 114.59996 | 104.8069 | 65.86698 | 43.5918 |
| 6.7125 | 119.6108 | 114.62789 | 104.8625 | 66.02265 | 43.6313 |
| 6.715 | 119.6319 | 114.65583 | 104.918 | 66.1797 | 43.67012 |
| 6.7175 | 119.6529 | 114.69068 | 104.9736 | 66.33745 | 43.70962 |
| 6.72 | 119.667 | 114.71861 | 105.0291 | 66.49519 | 43.74913 |
| 6.7225 | 119.6881 | 114.74655 | 105.0847 | 66.65363 | 43.78863 |
| 6.725 | 119.7091 | 114.77449 | 105.1472 | 66.81345 | 43.82814 |
| 6.7275 | 119.7301 | 114.80243 | 105.2027 | 66.97327 | 43.86764 |
| 6.73 | 119.7512 | 114.83036 | 105.2583 | 67.13378 | 43.90784 |
| 6.7325 | 119.7722 | 114.85830 | 105.3138 | 67.29429 | 43.94735 |
| 6.735 | 119.7932 | 114.88624 | 105.3625 | 67.45618 | 43.98685 |
| 6.7375 | 119.8143 | 114.91418 | 105.4181 | 67.61808 | 44.02705 |
| 6.74 | 119.8353 | 114.94211 | 105.4736 | 67.78067 | 44.06656 |
| 6.7426 | 119.8564 | 114.97005 | 105.5292 | 67.94395 | 44.10676 |
| 6.745 | 119.8774 | 114.99799 | 105.5847 | 68.10792 | 44.14695 |
| 6.7475 | 119.8984 | 115.02593 | 105.6334 | 68.27189 | 44.18715 |
| 6.75 | 119.9195 | 115.05387 | 105.6889 | 68.43656 | 44.22666 |
| 6.7525 | 119.9336 | 115.08180 | 105.7445 | 68.60191 | 44.26686 |
| 6.755 | 119.9546 | 115.10974 | 105.7931 | 68.76796 | 44.30775 |
| 6.7575 | 119.9757 | 115.13768 | 105.8487 | 68.93401 | 44.34795 |
| 6.76 | 119.9967 | 115.16562 | 105.8974 | 69.10075 | 44.38815 |
| 6.7625 | 120.0178 | 115.13665 | 105.9529 | 69.2668 | 44.42834 |
| 6.765 | 120.0388 | 115.21458 | 106.0016 | 69.43286 | 44.46924 |
| 6.7675 | 120.0598 | 115.24252 | 106.0571 | 69.60582 | 44.50944 |
| 6.77 | 120.074 | 115.27046 | 106.1058 | 69.77187 | 44.55033 |
| 6.7725 | 120.095 | 115.29840 | 106.1544 | 69.93793 | 44.59122 |
| 6.775 | 120.1161 | 115.32634 | 106.21 | 70.11089 | 44.63142 |
| 6.7775 | 120.1371 | 115.35428 | 106.2586 | 70.27695 | 44.67231 |
| 6.78 | 120.1581 | 115.38222 | 106.3073 | 70.44992 | 44.7132 |
| 6.7825 | 120.1792 | 115.40325 | 106.3559 | 70.61598 | 44.75409 |
| 6.785 | 120.1933 | 115.43118 | 106.4046 | 70.78895 | 44.79499 |
| 6.7875 | 120.2143 | 115.45912 | 106.4602 | 70.95501 | 44.83657 |
| 6.79 | 120.2354 | 115.48706 | 106.5088 | 71.12798 | 44.87746 |
| 6.7925 | 120.2564 | 115.51500 | 106.5575 | 71.30095 | 44.91835 |
| 6.795 | 120.2775 | 115.53603 | 106.6061 | 71.47392 | 44.95994 |
| 6.7975 | 120.2985 | 115.56397 | 106.6548 | 71.63999 | 45.00083 |
| 6.8 | 120.3128 | 115.59191 | 106.7034 | 71.81296 | 45.04242 |
| 6.8025 | 120.3337 | 115.61985 | 106.7521 | 71.98594 | 45.084 |
| 6.805 | 120.3547 | 115.64779 | 106.8007 | 72.15891 | 45.12559 |
| 6.8075 | 120.3757 | 115.66882 | 106.8494 | 72.33189 | 45.16717 |
| 6.81 | 120.3899 | 115.69676 | 106.8911 | 72.50487 | 45.20876 |
| 6.8125 | 120.4109 | 115.72470 | 106.9398 | 72.67785 | 45.25034 |
| 6.815 | 120.432 | 115.75264 | 106.9884 | 72.84392 | 45.29193 |

APPENDIX 1-continued

Standard Mass Calculation

| Pressure | Temps 15.1 | 17.2 | 20.1 C. | 25.1 C. | 35.1 C. |
|---|---|---|---|---|---|
| 6.8175 | 120.453 | 115.77367 | 107.0371 | 73.0169 | 45.33351 |
| 6.82 | 120.474 | 115.80161 | 107.0857 | 73.18988 | 45.37579 |
| 6.8225 | 120.4882 | 115.82955 | 107.1275 | 73.36286 | 45.41738 |
| 6.825 | 120.5092 | 115.85058 | 107.1761 | 73.53584 | 45.45965 |
| 6.8275 | 120.5302 | 115.87852 | 107.2248 | 73.70883 | 45.50193 |
| 6.83 | 120.5513 | 115.90646 | 107.2665 | 73.88181 | 45.54352 |
| 6.8325 | 120.5654 | 115.92749 | 107.3152 | 74.0548 | 45.5858 |
| 6.835 | 120.5865 | 115.96543 | 107.3669 | 74.22779 | 45.62807 |
| 6.8375 | 120.6075 | 115.98337 | 107.4056 | 74.40077 | 45.67035 |
| 6.84 | 120.6216 | 116.00440 | 107.4542 | 74.57376 | 45.71263 |
| 6.8425 | 120.6427 | 116.03234 | 107.496 | 74.74675 | 45.7556 |
| 6.845 | 120.6637 | 116.06028 | 107.5377 | 74.91283 | 45.79788 |
| 6.8475 | 120.6847 | 116.08131 | 107.5864 | 75.08582 | 45.84085 |
| 6.85 | 120.6989 | 116.10925 | 107.6281 | 75.25881 | 45.88313 |
| 6.8525 | 120.7199 | 116.13028 | 107.6768 | 75.4318 | 45.9261 |
| 6.855 | 120.741 | 116.15822 | 107.7185 | 75.6048 | 46.96838 |
| 6.8575 | 120.7551 | 116.18616 | 107.7603 | 75.77088 | 46.01135 |
| 6.88 | 120.7761 | 116.20719 | 107.8089 | 75.94388 | 46.05432 |
| 6.8625 | 120.7972 | 116.23514 | 107.8607 | 76.11687 | 46.0973 |
| 6.865 | 120.8182 | 116.25617 | 107.8924 | 76.28296 | 46.14027 |
| 6.8675 | 120.8323 | 116.28411 | 107.9411 | 76.45595 | 46.18393 |
| 6.87 | 120.8534 | 116.30514 | 107.9828 | 76.62204 | 46.2269 |
| 6.8725 | 120.8744 | 116.33308 | 108.0246 | 76.79504 | 46.26988 |
| 6.875 | 120.8886 | 116.36102 | 108.0663 | 76.96113 | 46.31364 |
| 6.8775 | 120.9096 | 116.38205 | 108.108 | 77.13413 | 46.35651 |
| 6.88 | 120.9306 | 116.40999 | 108.1498 | 77.30022 | 46.40018 |
| 6.8825 | 120.9448 | 116.43102 | 108.1915 | 77.46631 | 46.44384 |
| 6.885 | 120.9658 | 116.45897 | 108.2402 | 77.6324 | 46.4875 |
| 6.8875 | 120.9868 | 116.48000 | 108.282 | 77.8054 | 46.53117 |
| 6.89 | 121.001 | 116.50794 | 108.3237 | 77.9715 | 46.57483 |
| 6.8925 | 121.022 | 116.52897 | 108.3654 | 78.13759 | 46.6135 |
| 6.895 | 121.0361 | 116.55691 | 108.4072 | 78.30368 | 46.66286 |
| 6.8975 | 121.0572 | 116.57794 | 108.4489 | 78.46978 | 46.70652 |
| 6.9 | 121.0782 | 116.60589 | 108.4838 | 78.62896 | 46.75019 |
| 6.9025 | 121.0924 | 116.62692 | 108.5255 | 78.79506 | 46.79455 |
| 6.905 | 121.1134 | 116.64795 | 108.5673 | 78.96116 | 46.8389 |
| 6.9075 | 121.1344 | 116.67589 | 108.609 | 79.12034 | 46.88326 |
| 6.91 | 121.1486 | 116.69692 | 108.6508 | 79.28644 | 46.92762 |
| 6.9125 | 121.1696 | 116.72486 | 108.6925 | 79.44563 | 46.97198 |
| 6.915 | 121.1837 | 116.74589 | 108.7343 | 79.61173 | 47.01633 |
| 6.9175 | 121.2048 | 116.77384 | 108.7691 | 79.77092 | 47.06069 |
| 6.92 | 121.2258 | 116.79487 | 108.8108 | 79.93011 | 47.10505 |
| 6.9225 | 121.24 | 116.81590 | 108.8526 | 80.09621 | 47.1501 |
| 6.925 | 121.261 | 116.84384 | 108.8943 | 80.2554 | 47.19446 |
| 6.9275 | 121.2751 | 116.86488 | 108.9292 | 80.41459 | 47.23951 |
| 6.93 | 121.2962 | 116.89282 | 108.9709 | 80.56687 | 47.28456 |
| 8.9325 | 121.3172 | 116.91385 | 109.0127 | 80.72607 | 47.32892 |
| 6.935 | 121.3313 | 116.93488 | 109.0475 | 80.88526 | 47.37397 |
| 6.9375 | 121.3524 | 116.96283 | 109.0893 | 81.04445 | 47.41902 |
| 6.94 | 121.3665 | 116.98386 | 109.131 | 81.19674 | 47.46477 |
| 6.9425 | 121.3876 | 117.00489 | 1091659 | 81.34902 | 47.50982 |
| 6.945 | 121.4017 | 117.03283 | 109.2076 | 81.50822 | 47.55487 |
| 6.9475 | 121.4227 | 117.05386 | 109.2424 | 81.6605 | 47.60061 |
| 6.95 | 121.4369 | 117.07490 | 109.2842 | 81.81279 | 47.64567 |
| 6.9525 | 121.4579 | 117.10284 | 109.319 | 81.96508 | 47.69141 |
| 6.955 | 121.4789 | 117.12387 | 109.3608 | 82.11736 | 47.73715 |
| 6.9575 | 121.4931 | 117.14490 | 109.3956 | 82.26965 | 47.7829 |
| 6.96 | 121.5141 | 117.17285 | 109.4374 | 82.42194 | 47.82864 |
| 6.9625 | 121.5283 | 117.19388 | 109.4722 | 82.56732 | 47.87439 |
| 6.965 | 121.5493 | 117.21491 | 109.514 | 82.71961 | 47.92013 |
| 6.9675 | 121.5634 | 117.23595 | 109.5488 | 82.86498 | 47.96588 |
| 6.97 | 121.5845 | 117.26389 | 109.5905 | 83.01728 | 48.01231 |
| 6.9725 | 121.5986 | 117.28492 | 109.6254 | 83.16266 | 48.05806 |
| 6.975 | 121.6196 | 117.30595 | 109.6602 | 83.30804 | 48.1045 |
| 6.9775 | 121.6338 | 117.33390 | 109.702 | 83.45342 | 48.15093 |
| 6.98 | 121.6548 | 117.35493 | 109.7368 | 83.5988 | 48.19737 |
| 6.9826 | 121.6689 | 117.37596 | 109.7717 | 83.74418 | 48.24381 |
| 6.985 | 121.69 | 117.39700 | 109.8065 | 83.88956 | 48.29025 |
| 6.9875 | 121.7041 | 117.41803 | 109.8482 | 84.02803 | 48.33669 |
| 6.99 | 121.7252 | 117.44597 | 109.8831 | 84.17342 | 48.38312 |
| 6.9925 | 121.7393 | 117.46701 | 109.9179 | 84.31189 | 48.43025 |
| 6.995 | 121.7603 | 117.48804 | 109.9528 | 84.45036 | 48.47669 |
| 6.9975 | 121.7745 | 117.50907 | 109.9945 | 84.59575 | 48.52382 |
| 7 | 121.7955 | 117.53702 | 110.0294 | 84.73422 | 48.57095 |
| 7.0025 | 121.8096 | 117.55805 | 110.0642 | 84.8727 | 48.61739 |
| 7.005 | 121.8307 | 117.57908 | 110.099 | 85.01117 | 48.66452 |
| 7.0075 | 121.8448 | 117.60012 | 110.1339 | 85.14273 | 48.71165 |
| 7.01 | 121.8659 | 117.62115 | 110.1687 | 85.28121 | 48.75948 |
| 7.0125 | 121.88 | 117.64910 | 110.2105 | 85.41969 | 48.80661 |
| 7.015 | 121.901 | 117.67013 | 110.2453 | 85.55125 | 48.85374 |
| 7.0175 | 121.9152 | 117.69116 | 110.2802 | 85.68282 | 48.90156 |
| 7.02 | 121.9382 | 117.71220 | 110.315 | 85.8213 | 48.94939 |
| 7.0225 | 121.9503 | 117.73323 | 110.3498 | 85.95286 | 48.99652 |
| 7.025 | 121.9645 | 117.75426 | 110.3847 | 86.08443 | 49.04434 |
| 7.0275 | 121.9855 | 117.77530 | 110.4195 | 86.216 | 49.09217 |
| 7.03 | 121.9996 | 117.80324 | 110.4544 | 86.34065 | 49.13999 |
| 7.0325 | 122.0207 | 117.82428 | 110.4892 | 86.47222 | 49.18851 |
| 7.035 | 122.0348 | 117.84531 | 110.5241 | 86.60379 | 49.23633 |
| 7.0375 | 122.0559 | 117.86634 | 110.5589 | 86.72845 | 49.28416 |
| 7.04 | 122.07 | 117.88738 | 110.5937 | 86.86002 | 49.33267 |
| 7.0425 | 122.0841 | 117.90841 | 110.6286 | 86.98467 | 49.38119 |
| 7.045 | 122.1052 | 117.92944 | 110.6634 | 87.10933 | 49.42902 |
| 7.0475 | 122.1193 | 117.95048 | 110.6913 | 87.23399 | 49.47753 |
| 7.05 | 122.1403 | 117.97151 | 110.7262 | 87.35865 | 49.52605 |
| 7.0525 | 122.1545 | 117.99946 | 110.761 | 87.48331 | 49.57526 |
| 7.055 | 122.1755 | 118.02049 | 110.7959 | 87.60797 | 49.62378 |
| 7.0575 | 122.1896 | 118.04153 | 110.8307 | 87.72572 | 49.67229 |
| 7.06 | 122.2038 | 118.06256 | 110.8656 | 87.85038 | 49.7215 |
| 7.0625 | 122.2248 | 118.08360 | 110.8935 | 87.96813 | 49.77002 |
| 7.065 | 122.2389 | 118.10463 | 110.9283 | 88.09279 | 49.81923 |
| 7.0675 | 122.26 | 118.12566 | 110.9632 | 88.21054 | 49.86844 |
| 7.07 | 122.2741 | 118.14670 | 110.998 | 88.32829 | 49.91765 |
| 7.0725 | 122.2883 | 118.16773 | 111.0329 | 88.44604 | 49.96686 |
| 7.075 | 122.3093 | 118.18877 | 111.0608 | 88.5638 | 50.01608 |
| 7.0775 | 122.3234 | 118.20980 | 111.0956 | 88.68155 | 50.06598 |
| 7.08 | 122.3376 | 118.23084 | 111.1305 | 88.7993 | 50.11519 |
| 7.0825 | 122.3586 | 118.25187 | 111.1653 | 88.91014 | 50.16509 |
| 7.085 | 122.3727 | 118.27290 | 111.1933 | 89.02789 | 50.2143 |
| 7.0875 | 122.3938 | 118.29394 | 111.2281 | 89.13873 | 50.26421 |
| 7.09 | 122.4079 | 118.31497 | 111.263 | 89.25649 | 50.31411 |
| 7.0925 | 122.422 | 118.33601 | 111.2909 | 89.36733 | 50.36402 |
| 7.095 | 122.4431 | 118.35704 | 111.3257 | 89.47817 | 50.41392 |
| 7.0975 | 122.4572 | 118.37808 | 111.3537 | 89.58902 | 50.46452 |
| 7.1 | 122.4714 | 118.39911 | 111.3885 | 89.69986 | 50.51442 |
| 7.1025 | 122.4924 | 118.42015 | 111.4233 | 89.8107 | 50.56502 |
| 7.105 | 122.5065 | 118.44118 | 111.4513 | 89.92155 | 50.61492 |
| 7.1075 | 122.5207 | 118.46222 | 111.4861 | 90.02548 | 50.66552 |
| 7.11 | 122.5417 | 118.48325 | 111.5141 | 90.13632 | 50.71611 |
| 7.1125 | 122.5558 | 118.50429 | 111.5489 | 90.24717 | 50.76671 |
| 7.115 | 122.57 | 118.52532 | 111.5768 | 90.3511 | 50.81731 |
| 7.1175 | 122.591 | 118.54636 | 111.6117 | 90.45503 | 50.8686 |
| 7.12 | 122.6051 | 118.56739 | 111.6465 | 90.56588 | 50.9192 |
| 7.1225 | 122.6193 | 118.58843 | 111.6745 | 90.66981 | 50.97048 |
| 7.125 | 122.6403 | 118.60946 | 111.7093 | 90.77375 | 51.02108 |
| 7.1275 | 122.6544 | 118.63050 | 111.7372 | 90.87768 | 51.07237 |
| 7.13 | 122.6686 | 118.65153 | 111.7652 | 90.98162 | 51.12366 |
| 7.1325 | 122.6896 | 118.67257 | 111.8 | 91.07864 | 51.17495 |
| 7.135 | 122.7038 | 118.68669 | 111.8279 | 91.18258 | 51.22624 |
| 7.1375 | 122.7179 | 118.70773 | 111.8628 | 91.28651 | 51.27753 |
| 7.14 | 122.7389 | 118.72876 | 111.8907 | 91.38353 | 51.32952 |
| 7.1425 | 122.7531 | 118.74980 | 111.9256 | 91.48747 | 51.38081 |
| 7.145 | 122.7672 | 118.77083 | 111.9535 | 91.5845 | 51.43279 |
| 7.1475 | 122.7882 | 118.79187 | 111.9814 | 91.68152 | 51.48477 |
| 7.15 | 122.8024 | 118.81291 | 112.0163 | 91.78546 | 51.53676 |
| 7.1525 | 122.8165 | 118.83394 | 112.0442 | 91.88248 | 51.58874 |
| 7.155 | 122.8306 | 118.85498 | 112.0791 | 91.97951 | 51.64072 |
| 7.1575 | 122.8517 | 118.86910 | 112.107 | 92.07654 | 51.69271 |
| 7.16 | 122.8658 | 118.89013 | 112.1349 | 92.17356 | 51.74538 |
| 7.1625 | 122.8799 | 118.91117 | 112.1698 | 92.26367 | 51.79737 |
| 7.165 | 122.901 | 118.93221 | 112.1977 | 92.3671 | 51.85004 |
| 7.1675 | 122.9151 | 118.95324 | 112.2257 | 92.45773 | 51.90272 |
| 7.17 | 122.9293 | 118.97428 | 112.2536 | 92.54784 | 51.9554 |
| 7.1725 | 122.9434 | 118.99532 | 112.2884 | 92.64487 | 52.00807 |
| 7.175 | 122.9644 | 119.00944 | 112.3164 | 92.73499 | 52.06075 |
| 7.1775 | 122.9786 | 119.03047 | 112.3443 | 92.83202 | 52.11343 |
| 7.18 | 122.9927 | 119.05151 | 112.3791 | 92.92213 | 52.1668 |
| 7.1825 | 123.0068 | 119.07255 | 112.4071 | 93.01225 | 52.22017 |
| 7.185 | 123.0279 | 119.09358 | 112.435 | 93.10236 | 52.27285 |

APPENDIX 1-continued

Standard Mass Calculation

| Pressure | Temps 15.1 | 17.2 | 20.1 C. | 25.1 C. | 35.1 C. |
|---|---|---|---|---|---|
| 7.1875 | 123.042 | 119.11462 | 112.463 | 93.19248 | 52.32622 |
| 7.19 | 123.0561 | 119.12874 | 112.4909 | 93.2826 | 52.37959 |
| 7.1925 | 123.0703 | 119.14978 | 112.5257 | 93.37271 | 52.43296 |
| 7.195 | 123.0913 | 119.17082 | 112.5537 | 93.46283 | 52.48702 |
| 7.1975 | 123.1054 | 119.19185 | 112.5816 | 93.55295 | 52.54039 |
| 7.2 | 123.1196 | 119.21289 | 112.6095 | 93.63615 | 52.59376 |
| 7.2025 | 123.1337 | 119.22701 | 112.6375 | 93.72627 | 52.64782 |
| 7.205 | 123.1548 | 119.24805 | 112.6654 | 93.80948 | 52.70188 |
| 7.2075 | 123.1689 | 119.26908 | 112.7003 | 93.8996 | 52.75595 |
| 7.21 | 123.183 | 119.29012 | 112.7282 | 93.9828 | 52.81001 |
| 7.2125 | 123.1972 | 119.31116 | 112.7561 | 94.07292 | 52.86407 |
| 7.215 | 123.2182 | 119.32528 | 112.7841 | 94.15613 | 52.91814 |
| 7.2175 | 123.2323 | 119.34632 | 112.812 | 94.23934 | 52.97289 |
| 7.22 | 123.2465 | 119.36736 | 112.8399 | 94.32254 | 53.02696 |
| 7.2225 | 123.2606 | 119.38839 | 112.8679 | 94.40575 | 53.08171 |
| 7.225 | 123.2747 | 119.40251 | 112.8958 | 94.48896 | 53.13647 |
| 7.2275 | 123.2958 | 119.42355 | 112.9237 | 94.57217 | 53.19123 |
| 7.23 | 123.3099 | 119.44459 | 112.9517 | 94.65538 | 53.24598 |
| 7.2325 | 123.324 | 119.46563 | 112.9796 | 94.73859 | 53.30074 |
| 7.235 | 123.3382 | 119.47975 | 113.0076 | 94.8218 | 53.35619 |
| 7.2375 | 123.3523 | 119.50079 | 113.0355 | 94.89809 | 53.41095 |
| 7.24 | 123.3734 | 119.52182 | 113.0634 | 94.9813 | 53.4664 |
| 7.2425 | 123.3875 | 119.54286 | 113.0914 | 95.06451 | 53.52185 |
| 7.245 | 123.4016 | 119.55698 | 113.1193 | 95.14081 | 53.57729 |
| 7.2475 | 123.4157 | 119.57802 | 113.1472 | 95.2171 | 53.63274 |
| 7.25 | 123.4299 | 119.59906 | 113.1752 | 95.30031 | 53.68819 |
| 7.2525 | 123.4509 | 119.61318 | 113.2031 | 95.37661 | 53.74365 |
| 7.255 | 123.4651 | 119.63422 | 113.231 | 95.45291 | 53.79979 |
| 7.2575 | 123.4792 | 119.65526 | 113.259 | 95.53612 | 53.85593 |
| 7.26 | 123.4933 | 119.67630 | 113.2869 | 95.61242 | 53.91138 |
| 7.2625 | 123.5075 | 119.69042 | 113.3149 | 95.68872 | 53.96752 |
| 7.265 | 123.5216 | 119.71146 | 113.3428 | 95.76502 | 54.02367 |
| 7.2675 | 123.5426 | 119.73249 | 113.3707 | 95.84132 | 54.07981 |
| 7.27 | 123.5668 | 119.74662 | 113.3987 | 95.91761 | 54.13665 |
| 7.2725 | 123.5709 | 119.76766 | 113.4266 | 95.99391 | 54.19279 |
| 7.275 | 123.585 | 119.78869 | 113.4545 | 96.07021 | 54.24963 |
| 7.2775 | 123.5992 | 119.80282 | 113.4825 | 96.1396 | 54.30646 |
| 7.28 | 123.6133 | 119.82386 | 113.5035 | 96.2159 | 54.36261 |
| 7.2825 | 123.6343 | 119.84489 | 113.5314 | 96.2922 | 54.41944 |
| 7.285 | 123.6485 | 119.85902 | 113.5594 | 96.36159 | 54.47697 |
| 7.2875 | 123.6626 | 119.88005 | 113.5873 | 96.43789 | 54.53381 |
| 7.29 | 123.6767 | 119.90109 | 113.6153 | 96.50728 | 54.59064 |
| 7.2925 | 123.6909 | 119.91522 | 113.6432 | 96.58356 | 54.64817 |
| 7.295 | 123.705 | 119.93626 | 113.6642 | 96.65297 | 54.7057 |
| 7.2975 | 123.7261 | 119.95729 | 113.6922 | 96.72235 | 54.76254 |
| 7.3 | 123.7402 | 119.97142 | 113.7201 | 96.79866 | 54.82007 |
| 7.3025 | 123.7543 | 119.99246 | 113.748 | 96.86804 | 54.87829 |
| 7.305 | 123.7685 | 120.00658 | 113.776 | 96.93743 | 54.93582 |
| 7.3075 | 123.7826 | 120.02762 | 113.797 | 97.00682 | 54.99335 |
| 7.31 | 123.7967 | 120.04866 | 113.8249 | 97.07621 | 55.05158 |
| 7.3125 | 123.8109 | 120.06278 | 113.8529 | 97.1456 | 55.10911 |
| 7.315 | 123.825 | 120.08382 | 113.8808 | 97.21499 | 55.16733 |
| 7.3175 | 123.846 | 120.10486 | 113.9088 | 97.28438 | 55.22555 |
| 7.32 | 123.8602 | 120.11898 | 113.9298 | 97.35377 | 55.28378 |
| 7.3225 | 123.8743 | 120.14002 | 113.9577 | 97.42316 | 55.34269 |
| 7.325 | 123.8884 | 120.15414 | 113.9857 | 97.49255 | 55.40091 |
| 7.3275 | 123.9026 | 120.17518 | 114.0067 | 97.56194 | 55.45983 |
| 7.33 | 123.9167 | 120.19622 | 114.0346 | 97.62442 | 55.51805 |
| 7.3325 | 123.9308 | 120.21035 | 114.0626 | 97.69381 | 55.57697 |
| 7.335 | 123.945 | 120.23138 | 114.0905 | 97.7632 | 55.63589 |
| 7.3375 | 123.9591 | 120.24551 | 114.1115 | 97.82568 | 55.6948 |
| 7.34 | 123.9801 | 120.26665 | 114.1395 | 97.89507 | 55.75372 |
| 7.3425 | 123.9943 | 120.28067 | 114.1674 | 97.96755 | 55.81333 |
| 7.345 | 124.0084 | 120.30171 | 114.1884 | 98.02695 | 55.87225 |
| 7.3475 | 124.0225 | 120.32275 | 114.2164 | 98.08942 | 55.93186 |
| 7.35 | 124.0367 | 120.33687 | 114.2443 | 98.1519 | 55.99147 |
| 7.3525 | 124.0508 | 120.35791 | 114.2653 | 98.2213 | 56.05108 |
| 7.355 | 124.0649 | 120.37204 | 114.2933 | 98.28377 | 56.11069 |
| 7.3575 | 124.0791 | 120.39308 | 114.3143 | 98.34625 | 56.1703 |
| 7.36 | 124.0932 | 120.40720 | 114.3422 | 98.40873 | 56.22991 |
| 7.3625 | 124.1073 | 120.42824 | 114.3702 | 98.47813 | 56.29021 |
| 7.365 | 124.1215 | 120.44236 | 114.3912 | 98.54061 | 56.35051 |
| 7.3675 | 124.1356 | 120.46340 | 114.4191 | 98.60309 | 56.41012 |
| 7.37 | 124.1567 | 120.47753 | 114.4402 | 98.66557 | 56.47043 |
| 7.3725 | 124.1708 | 120.49857 | 114.4681 | 98.72805 | 56.53073 |
| 7.375 | 124.1849 | 120.51961 | 114.496 | 98.79053 | 56.59173 |
| 7.3775 | 124.1991 | 120.53373 | 114.5171 | 98.85301 | 56.65203 |
| 7.38 | 124.2132 | 120.55477 | 114.545 | 98.90858 | 56.71303 |
| 7.3825 | 124.2273 | 120.56890 | 114.566 | 98.97106 | 56.77333 |
| 7.385 | 124.2415 | 120.58994 | 114.594 | 99.03354 | 56.83433 |
| 7.3875 | 124.2556 | 120.60406 | 114.615 | 99.09602 | 56.89532 |
| 7.39 | 124.2697 | 120.62510 | 114.6429 | 99.15851 | 56.95632 |
| 7.3925 | 124.2839 | 120.63922 | 114.664 | 99.21407 | 57.01732 |
| 7.395 | 124.298 | 120.66026 | 114.6919 | 99.27656 | 57.07901 |
| 7.3975 | 124.3121 | 120.67439 | 114.7129 | 99.33212 | 57.14 |
| 7.4 | 124.3262 | 120.69543 | 114.7409 | 99.39461 | 57.20169 |
| 7.4025 | 124.3404 | 120.70955 | 114.7619 | 99.45709 | 57.26338 |
| 7.405 | 124.3545 | 120.73059 | 114.7898 | 99.51266 | 57.32507 |
| 7.4075 | 124.3686 | 120.74472 | 114.8109 | 99.57514 | 57.38676 |
| 7.41 | 124.3828 | 120.76576 | 114.8388 | 99.63071 | 57.44845 |
| 7.4125 | 124.3969 | 120.77988 | 114.8598 | 99.68628 | 57.51015 |
| 7.415 | 124.411 | 120.80092 | 114.8878 | 99.74877 | 57.57253 |
| 7.4175 | 124.4321 | 120.81505 | 114.9088 | 99.80434 | 57.63491 |
| 7.42 | 124.4462 | 120.82917 | 114.9368 | 99.85991 | 57.6966 |
| 7.4225 | 124.4604 | 120.85021 | 114.9578 | 99.92239 | 57.75899 |
| 7.425 | 124.4745 | 120.86434 | 114.9857 | 99.97796 | 57.82206 |
| 7.4275 | 124.4886 | 120.88538 | 115.0067 | 100.0335 | 57.88445 |
| 7.43 | 124.5028 | 120.89950 | 115.0347 | 100.0891 | 57.94683 |
| 7.4325 | 124.5169 | 120.92054 | 115.0557 | 100.1447 | 58.00991 |
| 7.435 | 124.531 | 120.93467 | 115.0767 | 100.2002 | 58.07229 |
| 7.4375 | 124.5452 | 120.95571 | 115.1047 | 100.2558 | 58.13537 |
| 7.44 | 124.5593 | 120.96983 | 115.1257 | 100.3114 | 58.19845 |
| 7.4425 | 124.5734 | 120.99087 | 115.1537 | 100.367 | 58.26153 |
| 7.445 | 124.5876 | 121.00500 | 115.1747 | 100.4225 | 58.3246 |
| 7.4475 | 124.6017 | 121.01912 | 115.1957 | 100.4781 | 58.38837 |
| 7.45 | 124.6158 | 121.04016 | 115.2237 | 100.5337 | 58.45145 |
| 7.4525 | 124.63 | 121.05429 | 115.2447 | 100.5892 | 58.51522 |
| 7.455 | 124.6441 | 121.07533 | 115.2657 | 100.6448 | 58.57899 |
| 7.4575 | 124.6582 | 121.08945 | 115.2936 | 100.7004 | 58.64276 |
| 7.46 | 124.6724 | 121.11050 | 115.3147 | 100.749 | 58.70653 |
| 7.4625 | 124.6865 | 121.12462 | 115.3357 | 100.8048 | 58.77031 |
| 7.465 | 124.7006 | 121.13875 | 115.3636 | 100.8602 | 58.83408 |
| 7.4675 | 124.7148 | 121.15979 | 115.3847 | 100.9158 | 58.89854 |
| 7.47 | 124.7289 | 121.17391 | 115.4057 | 100.9644 | 58.963 |
| 7.4725 | 124.743 | 121.19495 | 115.4336 | 101.02 | 59.02678 |
| 7.475 | 124.7572 | 121.20908 | 115.4547 | 101.0687 | 59.09124 |
| 7.4775 | 124.7713 | 121.22320 | 115.4757 | 101.1242 | 59.15571 |
| 7.48 | 124.7854 | 121.24424 | 115.5036 | 101.1729 | 59.22086 |
| 7.4825 | 124.7996 | 121.25837 | 115.5247 | 101.2285 | 59.28533 |
| 7.485 | 124.8137 | 121.27941 | 115.5457 | 101.2771 | 59.34979 |
| 7.4875 | 124.8278 | 121.29354 | 115.5736 | 101.3327 | 59.41495 |
| 7.49 | 124.842 | 121.30766 | 115.5947 | 101.3814 | 59.48011 |
| 7.4925 | 124.8492 | 121.32870 | 115.6157 | 101.4369 | 59.54527 |
| 7.495 | 124.8633 | 121.34283 | 115.6367 | 101.4856 | 59.61043 |
| 7.4975 | 124.8775 | 121.35695 | 115.6647 | 101.5343 | 59.67558 |
| 7.5 | 124.8916 | 121.37800 | 115.6857 | 101.5898 | 59.74074 |
| 7.5025 | 124.9057 | 121.39212 | 115.7067 | 101.6385 | 59.80659 |
| 7.505 | 124.9199 | 121.40625 | 115.7278 | 101.6872 | 59.87175 |
| 7.5075 | 124.934 | 121.42729 | 115.7557 | 101.7358 | 59.9376 |
| 7.51 | 124.9481 | 121.44141 | 115.7767 | 101.7914 | 60.00346 |
| 7.5125 | 124.9623 | 121.46246 | 115.7978 | 101.8401 | 60.06931 |
| 7.515 | 124.9764 | 121.47658 | 115.8188 | 101.8887 | 60.13516 |
| 7.5175 | 124.9905 | 121.49071 | 115.8467 | 101.9374 | 60.20101 |
| 7.52 | 125.0047 | 121.51175 | 115.8678 | 101.986 | 60.26756 |
| 7.5225 | 125.0188 | 121.52587 | 115.8888 | 102.0347 | 60.33341 |
| 7.525 | 125.0329 | 121.54000 | 115.9098 | 102.0834 | 60.39996 |
| 7.5275 | 125.0471 | 121.56104 | 115.9308 | 102.132 | 60.4665 |
| 7.53 | 126.0612 | 121.57517 | 115.9588 | 102.1807 | 60.53305 |
| 7.5325 | 125.0753 | 121.58929 | 115.9798 | 102.2293 | 60.59959 |
| 7.535 | 125.0895 | 121.61033 | 116.0008 | 102.278 | 60.66614 |
| 7.5375 | 125.1036 | 121.62446 | 116.0219 | 102.3267 | 60.73338 |
| 7.54 | 125.1177 | 121.63859 | 116.0429 | 102.3753 | 60.79993 |
| 7.5425 | 125.1249 | 121.65963 | 116.0639 | 102.424 | 60.86716 |
| 7.545 | 125.1391 | 121.67375 | 116.0919 | 102.4727 | 60.9344 |
| 7.5475 | 125.1532 | 121.68788 | 116.1129 | 102.5213 | 61.00095 |
| 7.55 | 125.1673 | 121.70892 | 116.1339 | 102.5631 | 61.06819 |
| 7.5525 | 125.1815 | 121.72305 | 116.155 | 102.6117 | 61.13612 |
| 7.555 | 125.1956 | 121.73717 | 116.176 | 102.6604 | 61.20336 |

APPENDIX 1-continued

Standard Mass Calculation

| Pressure | 15.1 | 17.2 | 20.1 C. | 25.1 C. | 35.1 C. |
|---|---|---|---|---|---|
| 7.5575 | 125.2097 | 121.75130 | 116.197 | 102.7091 | 61.2706 |
| 7.56 | 125.2239 | 121.77234 | 116.2181 | 102.7508 | 61.33854 |
| 7.5625 | 125.238 | 121.78647 | 116.2391 | 102.7995 | 61.40647 |
| 7.565 | 125.2522 | 121.80059 | 116.267 | 102.8481 | 61.47371 |
| 7.5675 | 125.2663 | 121.82164 | 116.2881 | 102.8899 | 61.54165 |
| 7.57 | 125.2804 | 121.83576 | 116.3091 | 102.9386 | 61.60958 |
| 7.5725 | 125.2876 | 121.84989 | 116.3301 | 102.9872 | 61.67821 |
| 7.575 | 125.3018 | 121.86401 | 116.3512 | 103.029 | 61.74614 |
| 7.5775 | 125.3159 | 121.88506 | 116.3722 | 103.0776 | 61.81407 |
| 7.58 | 125.33 | 121.89918 | 116.3932 | 103.1194 | 61.8827 |
| 7.5825 | 125.3442 | 121.91331 | 116.4142 | 103.1681 | 61.95133 |
| 7.585 | 125.3583 | 121.93435 | 116.4353 | 103.2098 | 62.01996 |
| 7.5875 | 125.3724 | 121.94848 | 116.4563 | 103.2585 | 62.08858 |
| 7.59 | 125.3866 | 121.96260 | 116.4773 | 103.3002 | 62.15721 |
| 7.5925 | 125.4007 | 121.97673 | 116.5053 | 103.3489 | 62.22584 |
| 7.595 | 125.4148 | 121.99777 | 116.5263 | 103.3906 | 62.29447 |
| 7.5975 | 125.4221 | 122.01190 | 116.5473 | 103.4324 | 62.36379 |
| 7.6 | 125.4362 | 122.02602 | 116.5684 | 103.4811 | 62.43242 |
| 7.6025 | 125.4503 | 122.04015 | 116.5894 | 103.5228 | 62.50174 |
| 7.605 | 125.4645 | 122.06119 | 116.6104 | 103.5646 | 62.57106 |
| 7.6075 | 125.4786 | 122.07532 | 116.6315 | 103.6132 | 62.64038 |
| 7.61 | 125.4927 | 122.08945 | 116.6525 | 103.655 | 62.7097 |
| 7.6125 | 125.5069 | 122.10357 | 116.6735 | 103.6967 | 62.77903 |
| 7.615 | 125.521 | 122.12462 | 116.6945 | 103.7385 | 62.84835 |
| 7.6175 | 125.5351 | 122.13874 | 116.7156 | 103.7871 | 62.91836 |
| 7.62 | 125.5424 | 122.15287 | 116.7366 | 103.8289 | 62.98769 |
| 7.6225 | 125.5565 | 122.16699 | 116.7576 | 103.8707 | 63.0577 |
| 7.625 | 125.5706 | 122.18804 | 116.7787 | 103.9124 | 63.12772 |
| 7.6275 | 125.5848 | 122.20216 | 116.7997 | 103.9542 | 63.19704 |
| 7.63 | 125.5989 | 122.21629 | 116.8207 | 103.9959 | 63.26706 |
| 7.6325 | 125.613 | 122.23042 | 116.8418 | 104.0446 | 63.33777 |
| 7.635 | 125.6272 | 122.25146 | 116.8628 | 104.0863 | 63.40778 |
| 7.6375 | 125.6344 | 122.26559 | 116.8838 | 104.1281 | 63.4778 |
| 7.64 | 125.6485 | 122.27971 | 116.9049 | 104.1698 | 63.54851 |
| 7.6425 | 125.6626 | 122.29384 | 116.9259 | 104.2116 | 63.61853 |
| 7.645 | 125.6768 | 122.30797 | 116.9469 | 104.2533 | 63.68924 |
| 7.6475 | 125.6909 | 122.32901 | 116.9679 | 104.2951 | 63.75995 |
| 7.65 | 125.705 | 122.34314 | 116.9821 | 104.3368 | 63.83066 |
| 7.6525 | 125.7192 | 122.35726 | 117.0031 | 104.3786 | 63.90137 |
| 7.655 | 125.7264. | 122.37139 | 117.0241 | 104.4204 | 63.97208 |
| 7.6575 | 125.7405 | 122.38551 | 117.0452 | 104.4621 | 64.04279 |
| 7.66 | 125.7547 | 122.40656 | 117.0662 | 104.4969 | 64.1135 |
| 7.6625 | 125.7688 | 122.42069 | 117.0872 | 104.5387 | 64.18491 |
| 7.665 | 125.7829 | 122.43481 | 117.1083 | 104.5805 | 64.25562 |
| 7.6675 | 125.7971 | 122.44894 | 117.1293 | 104.6222 | 64.32703 |
| 7.67 | 125.8043 | 122.46307 | 117.1503 | 104.664 | 64.39843 |
| 7.6725 | 125.8184 | 122.48411 | 117.1713 | 104.7057 | 64.46914 |
| 7.675 | 125.8326 | 122.49824 | 117.1924 | 104.7406 | 64.54055 |
| 7.6775 | 125.8467 | 122.51236 | 117.2134 | 104.7823 | 64.61195 |
| 7.68 | 125.8608 | 122.52649 | 117.2275 | 104.8241 | 64.68405 |
| 7.6825 | 125.875 | 122.54062 | 117.2486 | 104.8658 | 64.75546 |
| 7.685 | 125.8822 | 122.55474 | 117.2698 | 104.9007 | 64.82687 |
| 7.6875 | 125.8963 | 122.57579 | 117.2906 | 104.9424 | 64.89896 |
| 7.69 | 125.9104 | 122.58991 | 117.3117 | 104.9842 | 64.97037 |
| 7.6925 | 125.9246 | 122.60404 | 117.3327 | 105.0259 | 65.04247 |
| 7.695 | 125.9387 | 122.61817 | 117.3537 | 105.0608 | 65.11457 |
| 7.6975 | 125.9529 | 122.63229 | 117.3747 | 105.1025 | 65.18598 |
| 7.7 | 125.9601 | 122.64642 | 117.3889 | 105.1443 | 65.25808 |
| 7.7025 | 125.9742 | 122.66747 | 117.4099 | 105.1791 | 65.33018 |
| 7.705 | 125.9883 | 122.68159 | 117.4309 | 105.2209 | 65.40228 |
| 7.7075 | 126.0025 | 122.69572 | 117.452 | 105.2557 | 65.47507 |
| 7.71 | 126.0166 | 122.70985 | 117.473 | 105.2975 | 65.54718 |
| 7.7125 | 126.0238 | 122.72397 | 117.494 | 105.3323 | 65.61928 |
| 7.715 | 126.038 | 122.73810 | 117.5081 | 105.3741 | 65.69207 |
| 7.7175 | 126.0521 | 122.75223 | 117.5292 | 105.4089 | 65.76417 |
| 7.72 | 126.0662 | 122.77327 | 117.5502 | 105.4507 | 65.83697 |
| 7.7225 | 126.0804 | 122.78740 | 117.5712 | 105.4855 | 65.90976 |
| 7.725 | 126.0945 | 122.80153 | 117.5923 | 105.5273 | 65.98187 |
| 7.7275 | 126.1017 | 122.81565 | 117.6133 | 105.5621 | 66.05466 |
| 7.73 | 126.1158 | 122.82978 | 117.6274 | 105.6039 | 66.12746 |
| 7.7325 | 126.13 | 122.84391 | 117.6484 | 105.6387 | 66.20025 |
| 7.735 | 126.1441 | 122.85803 | 117.6695 | 105.6805 | 66.27305 |
| 7.7375 | 126.1513 | 122.87216 | 117.6905 | 105.7153 | 66.34654 |
| 7.74 | 126.1655 | 122.89321 | 117.7115 | 105.7501 | 66.41934 |
| 7.7425 | 126.1796 | 122.90733 | 117.7257 | 105.7919 | 66.49213 |
| 7.745 | 126.1937 | 122.92146 | 117.7467 | 105.8267 | 66.56562 |
| 7.7475 | 126.2079 | 122.93559 | 117.7677 | 105.8616 | 66.83842 |
| 7.75 | 126.2151 | 122.94971 | 117.7888 | 105.9033 | 66.71191 |
| 7.7525 | 126.2292 | 122.96384 | 117.8029 | 105.9382 | 66.7854 |
| 7.755 | 126.2434 | 122.97797 | 117.8239 | 105.973 | 66.8582 |
| 7.7575 | 126.2575 | 122.99210 | 117.8449 | 106.0148 | 66.93169 |
| 7.76 | 126.2716 | 123.00622 | 117.866 | 106.0496 | 67.00518 |
| 7.7625 | 126.2788 | 123.02727 | 117.887 | 106.0845 | 67.07868 |
| 7.765 | 126.293 | 123.04140 | 117.9011 | 106.1193 | 67.15217 |
| 7.7675 | 126.3071 | 123.05552 | 117.9222 | 106.1611 | 67.22566 |
| 7.77 | 126.3213 | 123.06965 | 117.9432 | 106.1959 | 67.29915 |
| 7.7725 | 126.3285 | 123.08378 | 117.9573 | 106.2308 | 67.37265 |
| 7.775 | 126.3426 | 123.09790 | 117.9783 | 106.2656 | 67.44683 |
| 7.7775 | 126.3567 | 123.11203 | 117.9994 | 106.3004 | 67.52033 |
| 7.78 | 126.3709 | 123.12616 | 118.0204 | 106.3422 | 67.59382 |
| 7.7825 | 126.385 | 123.14029 | 118.0345 | 106.377 | 67.66801 |
| 7.785 | 126.3922 | 123.15441 | 118.0556 | 106.4119 | 67.7415 |
| 7.7875 | 126.4064 | 123.16854 | 118.0766 | 106.4467 | 67.81569 |
| 7.79 | 126.4205 | 123.18267 | 118.0976 | 106.4816 | 67.88918 |
| 7.7925 | 126.4346 | 123.20371 | 118.1117 | 106.5164 | 67.96337 |
| 7.795 | 126.4418 | 123.21784 | 118.1328 | 106.5513 | 68.03756 |
| 7.7975 | 126.456 | 123.23197 | 118.1538 | 106.5861 | 68.11175 |
| 7.8 | 126.4701 | 123.24610 | 118.1679 | 106.6209 | 68.18524 |
| 7.8025 | 126.4843 | 123.26022 | 118.189 | 106.6558 | 68.25943 |
| 7.805 | 126.4915 | 123.27435 | 118.21 | 106.6906 | 68.33362 |
| 7.8075 | 126.5056 | 123.28848 | 118.2241 | 106.7255 | 68.40781 |
| 7.81 | 126.5197 | 123.30261 | 118.2451 | 106.7603 | 68.482 |
| 7.8125 | 126.5339 | 123.31673 | 118.2662 | 106.7952 | 68.55619 |
| 7.815 | 126.5411 | 123.33086 | 118.2803 | 106.83 | 63.63038 |
| 7.8175 | 126.5552 | 123.34499 | 118.3013 | 106.8649 | 68.70526 |
| 7.82 | 126.5694 | 123.35912 | 118.3224 | 106.8997 | 68.77945 |
| 7.8225 | 126.5835 | 123.37324 | 118.3365 | 106.9345 | 68.85364 |
| 7.825 | 126.5907 | 123.38737 | 118.3575 | 106.9694 | 68.92784 |
| 7.8275 | 126.6048 | 123.40150 | 118.3785 | 107.0042 | 69.00272 |
| 7.83 | 126.619 | 123.41563 | 118.3927 | 107.0391 | 69.07691 |
| 7.8325 | 126.6331 | 123.42976 | 118.4137 | 107.0739 | 69.15111 |
| 7.835 | 126.6403 | 123.44388 | 118.4347 | 107.1088 | 69.22876 |
| 7.8375 | 126.6545 | 123.45801 | 118.4488 | 107.1367 | 69.29811 |
| 7.84 | 126.6686 | 123.47214 | 118.4699 | 107.1715 | 69.37438 |
| 7.8425 | 126.6758 | 123.49319 | 118.4909 | 107.2064 | 69.45065 |
| 7.845 | 126.69 | 123.50731 | 118.505 | 107.2412 | 69.52692 |
| 7.8475 | 126.7041 | 123.52144 | 118.5261 | 107.2761 | 69.59627 |
| 7.85 | 126.7182 | 123.53557 | 118.5402 | 107.3109 | 69.67254 |
| 7.8525 | 126.7254 | 123.54970 | 118.5612 | 107.3389 | 69.74881 |
| 7.855 | 126.7396 | 123.56382 | 118.5822 | 107.3737 | 69.82508 |
| 7.8575 | 126.7537 | 123.57795 | 118.5964 | 107.4086 | 69.89443 |
| 7.86 | 126.7678 | 123.59208 | 118.6174 | 107.4434 | 69.9707 |
| 7.8625 | 126.7751 | 123.60621 | 118.6384 | 107.4713 | 70.04698 |
| 7.865 | 126.7892 | 123.62034 | 118.6526 | 107.5062 | 70.12325 |
| 7.8675 | 126.8033 | 123.63446 | 118.6736 | 107.541 | 70.1926 |
| 7.87 | 126.8106 | 123.64859 | 118.6877 | 107.5759 | 70.26888 |
| 7.8725 | 126.8247 | 123.66272 | 118.7087 | 107.6038 | 70.34515 |
| 7.875 | 126.8388 | 123.67685 | 118.7298 | 107.6386 | 70.42142 |
| 7.8775 | 126.853 | 123.69098 | 118.7439 | 107.6735 | 70.4977 |
| 7.88 | 126.8602 | 123.70510 | 118.7649 | 107.7014 | 70.56705 |
| 7.8825 | 126.8743 | 123.71923 | 118.779 | 107.7363 | 70.64333 |
| 7.885 | 126.8884 | 123.73336 | 118.8001 | 107.7711 | 70.7196 |
| 7.8875 | 126.8957 | 123.74749 | 118.8142 | 107.799 | 70.79588 |
| 7.89 | 126.9098 | 123.76162 | 118.8352 | 107.8339 | 70.87215 |
| 7.8925 | 126.9239 | 123.77574 | 118.8563 | 107.8618 | 70.94151 |
| 7.895 | 126.9311 | 123.78987 | 118.8704 | 107.8967 | 71.01779 |
| 7.8975 | 126.9453 | 123.80400 | 118.8914 | 107.9315 | 71.09406 |
| 7.9 | 126.9594 | 123.81813 | 118.9055 | 107.9594 | 71.17034 |
| 7.9025 | 126.9736 | 123.83226 | 118.9266 | 107.9943 | 71.2397 |
| 7.905 | 126.9808 | 123.84638 | 118.9407 | 108.0222 | 71.31598 |
| 7.9075 | 126.9949 | 123.86051 | 118.9617 | 108.0571 | 71.39226 |
| 7.91 | 127.009 | 123.87464 | 118.9758 | 108.085 | 71.46853 |
| 7.9125 | 127.0163 | 123.88877 | 118.9969 | 108.1198 | 71.54481 |
| 7.915 | 127.0304 | 123.90290 | 119.011 | 108.1547 | 71.61417 |
| 7.9175 | 127.0445 | 123.91011 | 119.032 | 108.1826 | 71.69045 |
| 7.92 | 127.0517 | 123.92423 | 119.0531 | 108.2175 | 71.76673 |
| 7.9225 | 127.0659 | 123.93836 | 119.0672 | 108.2454 | 71.84301 |
| 7.925 | 127.08 | 123.95249 | 119.0882 | 108.2733 | 71.91237 |

APPENDIX 1-continued

Standard Mass Calculation

| Pressure | 15.1 | 17.2 | 20.1 C. | 25.1 C. | 35.1 C. |
|---|---|---|---|---|---|
| 7.9275 | 127.0872 | 123.96662 | 119.1023 | 108.3082 | 71.98865 |
| 7.93 | 127.1014 | 123.98075 | 119.1234 | 108.3361 | 72.06493 |
| 7.9325 | 127.1155 | 123.99487 | 119.1375 | 108.371 | 72.14121 |
| 7.935 | 127.1227 | 124.00900 | 119.1585 | 108.3989 | 72.2175 |
| 7.9375 | 127.1369 | 124.02313 | 119.1726 | 108.4337 | 72.28686 |
| 7.94 | 127.151 | 124.03726 | 119.1937 | 108.4617 | 72.36314 |
| 7.9425 | 127.1582 | 124.05139 | 119.2078 | 108.4965 | 72.43942 |
| 7.945 | 127.1723 | 124.06552 | 119.2288 | 108.5245 | 72.51571 |
| 7.9475 | 127.1865 | 124.07964 | 119.2429 | 108.5524 | 72.58507 |
| 7.95 | 127.1937 | 124.09377 | 119.264 | 108.5872 | 72.66135 |
| 7.9525 | 127.2078 | 124.10790 | 119.2781 | 108.6152 | 72.73764 |
| 7.955 | 127.222 | 124.12203 | 119.2991 | 108.6431 | 72.81392 |
| 7.9575 | 127.2292 | 124.13616 | 119.3133 | 108.678 | 72.88329 |
| 7.96 | 127.2433 | 124.15029 | 119.3343 | 108.7059 | 72.95957 |
| 7.9625 | 127.2575 | 124.16441 | 119.3484 | 108.7338 | 73.03586 |
| 7.965 | 127.2647 | 124.17854 | 119.3625 | 108.7687 | 73.11214 |
| 7.9675 | 127.2788 | 124.18575 | 119.3836 | 108.7966 | 73.18151 |
| 7.97 | 127.2929 | 124.19988 | 119.3977 | 108.8245 | 73.25779 |
| 7.9725 | 127.3002 | 124.21401 | 119.4187 | 108.8594 | 73.33408 |
| 7.975 | 127.3143 | 124.22814 | 119.4328 | 108.8873 | 73.41037 |
| 7.9775 | 127.3284 | 124.24227 | 119.4539 | 108.9152 | 73.47973 |
| 7.98 | 127.3356 | 124.25639 | 119.468 | 108.9432 | 73.55602 |
| 7.9825 | 127.3498 | 124.27052 | 119.489 | 108.978 | 73.63231 |
| 7.985 | 127.3639 | 124.28465 | 119.5031 | 109.006 | 73.7086 |
| 7.9875 | 127.3711 | 124.29878 | 119.5242 | 109.0339 | 73.77797 |
| 7.99 | 127.3853 | 124.31291 | 119.5383 | 109.0618 | 73.85425 |
| 7.9925 | 127.3994 | 124.32704 | 119.5524 | 109.0967 | 73.93054 |
| 7.995 | 127.4068 | 124.34117 | 119.5735 | 109.1246 | 73.99991 |
| 7.9975 | 127.4208 | 124.35530 | 119.5876 | 109.1525 | 74.0762 |
| 8 | 127.4349 | 124.36250 | 119.8086 | 109.1805 | 74.15249 |
| 8.0025 | 127.4421 | 124.37663 | 119.6227 | 109.2084 | 74.22186 |
| 8.005 | 127.4562 | 124.39076 | 119.6438 | 109.2433 | 74.29815 |
| 8.0075 | 127.4704 | 124.40489 | 119.6579 | 109.2712 | 74.37444 |
| 8.01 | 127.4776 | 124.41902 | 119.672 | 109.2991 | 74.44382 |
| 8.0125 | 127.4917 | 124.43315 | 119.693 | 109.3271 | 74.52011 |
| 8.015 | 127.4989 | 124.44728 | 119.7072 | 109.355 | 74.5964 |
| 8.0175 | 127.5131 | 124.46140 | 119.7282 | 109.3829 | 74.66577 |
| 8.02 | 127.5272 | 124.47553 | 119.7423 | 109.4109 | 74.74206 |
| 8.0225 | 127.5344 | 124.48966 | 119.7564 | 109.4457 | 74.81836 |
| 8.025 | 127.5486 | 124.49687 | 119.7775 | 109.4737 | 74.88773 |
| 8.0275 | 127.5627 | 124.51100 | 119.7916 | 109.5016 | 74.96402 |
| 8.03 | 127.5699 | 124.52513 | 119.8126 | 109.5295 | 75.0334 |
| 8.0325 | 127.5841 | 124.53926 | 119.8267 | 109.5575 | 75.10969 |
| 8.035 | 127.5913 | 124.55339 | 119.8409 | 109.5854 | 75.18599 |
| 8.0375 | 127.6054 | 124.56752 | 119.8619 | 109.6133 | 75.25536 |
| 8.04 | 127.6195 | 124.58164 | 119.876 | 109.6413 | 75.33165 |
| 8.0425 | 127.6268 | 124.59577 | 119.897 | 109.6692 | 75.40103 |
| 8.045 | 127.6409 | 124.60990 | 119.9112 | 109.6971 | 75.47733 |
| 8.0475 | 127.655 | 124.61711 | 119.9253 | 109.7251 | 75.55362 |
| 8.05 | 127.6622 | 124.63124 | 119.9463 | 109.753 | 75.623 |
| 8.0525 | 127.6764 | 124.64537 | 119.9604 | 109.7809 | 75.69929 |
| 8.055 | 127.6836 | 124.65950 | 119.9746 | 109.8089 | 75.76867 |
| 8.0575 | 127.6977 | 124.67363 | 119.9956 | 109.8368 | 75.84497 |
| 8.08 | 127.7119 | 124.68776 | 120.0097 | 109.8647 | 75.91435 |
| 8.0625 | 127.7191 | 124.70188 | 120.0308 | 109.8927 | 75.99064 |
| 8.065 | 127.7332 | 124.70909 | 120.0449 | 109.9206 | 76.06002 |
| 8.0675 | 127.7404 | 124.72322 | 120.059 | 109.9485 | 76.13632 |
| 8.07 | 127.7546 | 124.73735 | 120..08 | 109.9765 | 76.2057 |
| 8.0725 | 127.7687 | 124.75148 | 120.0941 | 110.0044 | 76.282 |
| 8.075 | 127.7759 | 124.76561 | 120.1083 | 110.0323 | 76.35138 |
| 8.0775 | 127.7901 | 124.77974 | 120.1293 | 110.0603 | 76.42768 |
| 8.08 | 127.7973 | 124.79387 | 120.1434 | 110.0882 | 76.49706 |
| 8.0825 | 127.8114 | 124.80108 | 120.1575 | 110.1162 | 76.57336 |
| 8.085 | 127.8256 | 124.81521 | 120.1786 | 110.1441 | 76.64274 |
| 8.0875 | 127.8328 | 124.82953 | 120.1927 | 110.172 | 76.71212 |
| 8.09 | 127.8469 | 124.84346 | 120.2068 | 110.193 | 76.78842 |
| 8.0925 | 127.8541 | 124.85759 | 120.2279 | 110.221 | 76.8578 |
| 8.095 | 127.8683 | 124.87172 | 120.242 | 110.2489 | 76.9341 |
| 8.0975 | 127.8824 | 124.88585 | 120.2561 | 110.2769 | 77.00348 |
| 8.1 | 127.8896 | 124.89306 | 120.2771 | 110.3048 | 77.07287 |
| 8.1025 | 127.9037 | 124.90719 | 120.2912 | 110.3327 | 77.14917 |
| 8.105 | 127.911 | 124.92132 | 120.3054 | 110.3607 | 77.21855 |
| 8.1075 | 127.9251 | 124.93545 | 120.3195 | 110.3886 | 77.29486 |
| 8.11 | 127.9392 | 124.94958 | 120.3405 | 110.4096 | 77.36424 |
| 8.1125 | 127.9464 | 124.96371 | 120.3546 | 110.4375 | 77.43362 |
| 8.115 | 127.9606 | 124.97091 | 120.3688 | 110.4655 | 77.50993 |
| 8.1175 | 127.9678 | 124.98504 | 120.3898 | 110.4934 | 77.57931 |
| 8.12 | 127.9819 | 124.99917 | 120.4039 | 110.5214 | 77.64869 |
| 8.1225 | 127.9961 | 125.01330 | 120.418 | 110.5424 | 77.71808 |
| 8.125 | 128.0033 | 125.02743 | 120.4391 | 110.5703 | 77.79439 |
| 8.1275 | 128.0174 | 125.03464 | 120.4532 | 110.5983 | 77.86377 |
| 8.13 | 128.0246 | 125.04877 | 120.4673 | 110.6262 | 77.93316 |
| 8.1325 | 128.0388 | 125.06290 | 120.4814 | 110.6541 | 78.00946 |
| 8.135 | 128.046 | 125.07703 | 120.5025 | 110.6751 | 78.07885 |
| 8.1375 | 128.0601 | 125.09116 | 120.5166 | 110.7031 | 78.14824 |
| 8.14 | 128.0743 | 125.10529 | 120.5307 | 110.731 | 78.21762 |
| 8.1425 | 128.0816 | 125.11250 | 120.5518 | 110.759 | 78.28701 |
| 8.145 | 128.0956 | 125.12663 | 120.5659 | 110.78 | 78.36332 |
| 8.1475 | 128.1028 | 125.14076 | 120.58 | 110.8079 | 78.43271 |
| 8.15 | 128.117 | 125.15488 | 120.5941 | 110.8358 | 78.50209 |
| 8.1525 | 128.1242 | 125.16901 | 120.6151 | 110.8638 | 78.57148 |
| 8.155 | 128.1383 | 125.17622 | 120.6293 | 110.8848 | 78.64087 |
| 8.1575 | 128.1525 | 125.19035 | 120.6434 | 110.9127 | 78.71026 |
| 8.16 | 128.1597 | 125.20448 | 120.6575 | 110.9407 | 78.78657 |
| 8.1625 | 128.1738 | 125.21861 | 120.6785 | 110.9617 | 78.85596 |
| 8.165 | 128.181 | 125.23274 | 120.6927 | 110.9896 | 78.92535 |
| 8.1675 | 128.1952 | 125.23995 | 120.7068 | 111.0176 | 78.99474 |
| 8.17 | 128.2024 | 125.25408 | 120.7209 | 111.0386 | 79.06413 |
| 8.1725 | 128.2165 | 125.26821 | 120.7419 | 111.0665 | 79.13352 |
| 8.175 | 128.2237 | 125.28234 | 120.7561 | 111.0945 | 79.20291 |
| 8.1775 | 128.2379 | 125.29647 | 120.7702 | 111.1155 | 79.2723 |
| 8.18 | 128.252 | 125.30368 | 120.7843 | 111.1434 | 79.34169 |
| 8.1825 | 128.2592 | 125.31781 | 120.7984 | 111.1714 | 79.41108 |
| 8.185 | 128.2733 | 125.33194 | 120.8195 | 111.1924 | 79.48048 |
| 8.1875 | 128.2806 | 125.34607 | 120.8336 | 111.2203 | 79.54987 |
| 8.19 | 128.2947 | 125.36019 | 120.8477 | 111.2413 | 79.61926 |
| 8.1925 | 128.3019 | 125.36740 | 120.8618 | 111.2693 | 79.68865 |
| 8.195 | 128.3161 | 125.38153 | 120.8829 | 111.2972 | 79.75805 |
| 8.1975 | 128.3233 | 125.39566 | 120.897 | 111.3182 | 79.82744 |
| 8.2 | 128.3374 | 125.40979 | 120.9111 | 111.3462 | 79.89683 |
| 8.2025 | 128.3515 | 125.41700 | 120.9252 | 111.3672 | 79.96623 |
| 8.205 | 128.3588 | 125.43113 | 120.9393 | 111.3951 | 80.03562 |
| 8.2075 | 123.3729 | 125.44526 | 120.9604 | 111.4231 | 80.10502 |
| 8.21 | 128.3801 | 125.45939 | 120.9745 | 111.4441 | 80.16749 |
| 8.2125 | 128.3942 | 125.47352 | 120.9886 | 111.472 | 80.23689 |
| 8.215 | 128.4015 | 125.48073 | 121.0027 | 111.4931 | 80.30628 |
| 8.2175 | 128.4156 | 125.49486 | 121.0169 | 111.521 | 80.37568 |
| 8.22 | 128.4228 | 125.50899 | 121.0379 | 111.542 | 80.44507 |
| 8.2225 | 128.4369 | 125.52312 | 121.052 | 111.57 | 80.51447 |
| 8.225 | 128.4442 | 125.53033 | 121.0661 | 111.591 | 80.57695 |
| 8.2275 | 128.4583 | 125.54446 | 121.0803 | 111.6189 | 80.64634 |
| 8.23 | 128.4655 | 125.55859 | 121.0944 | 111.6399 | 80.71574 |
| 8.2325 | 128.4797 | 125.57272 | 121.1154 | 111.6679 | 80.78514 |
| 8.235 | 128.4938 | 125.57992 | 121.1295 | 111.6958 | 80.84761 |
| 8.2375 | 128.501 | 125.59405 | 121.1437 | 111.7168 | 80.91701 |
| 8.24 | 128.5151 | 125.60818 | 121.1578 | 111.7448 | 80.98641 |
| 8.2425 | 128.5224 | 125.62231 | 121.1719 | 111.7658 | 81.05581 |
| 8.245 | 128.5365 | 125.62952 | 121.186 | 111.7868 | 81.11829 |
| 8.2475 | 128.5437 | 125.64365 | 121.2071 | 111.8148 | 81.18768 |
| 8.25 | 128.5578 | 125.65778 | 121.2212 | 111.8358 | 81.25708 |
| 8.2525 | 128.5651 | 125.67191 | 121.2353 | 111.8637 | 81.31956 |
| 8.255 | 128.5792 | 125.67912 | 121.2494 | 111.8847 | 81.38896 |
| 8.2575 | 128.5864 | 125.69325 | 121.2635 | 111.9127 | 81.45144 |
| 8.26 | 128.6005 | 125.70738 | 121.2777 | 111.9337 | 81.52084 |
| 8.2625 | 128.6078 | 125.72151 | 121.2987 | 111.9616 | 81.59024 |
| 8.265 | 128.6219 | 125.72872 | 121.3128 | 111.9827 | 81.65272 |
| 8.2675 | 128.6291 | 125.74285 | 121.3269 | 112.0106 | 81.72212 |
| 8.27 | 128.6433 | 125.75698 | 121.3411 | 112.0316 | 81.7846 |
| 8.2725 | 128.6505 | 125.77111 | 121.3552 | 112.0526 | 81.85401 |
| 8.275 | 128.6646 | 125.77832 | 121.3693 | 112.0806 | 81.91649 |
| 8.2775 | 128.6718 | 125.79245 | 121.3903 | 112.1016 | 81.98589 |
| 8.28 | 128.686 | 125.80658 | 121.4045 | 112.1295 | 82.04837 |
| 8.2825 | 128.6932 | 125.81379 | 121.4186 | 112.1506 | 82.11771 |
| 8.285 | 128.7073 | 125.82792 | 121.4327 | 112.1716 | 82.18025 |
| 8.2875 | 128.7145 | 125.84205 | 121.4468 | 112.1995 | 82.24966 |
| 8.29 | 128.7287 | 125.85618 | 121.4609 | 112.2205 | 82.31214 |
| 8.2925 | 128.7359 | 125.86338 | 121.4751 | 112.2416 | 82.38154 |
| 8.295 | 128.75 | 125.87751 | 121.4892 | 112.2695 | 82.44403 |

APPENDIX 1-continued

Standard Mass Calculation

| Pressure | 15.1 | 17.2 | 20.1 C. | 25.1 C. | 35.1 C. |
|---|---|---|---|---|---|
| 8.2975 | 128.7572 | 125.89164 | 121.5102 | 112.2905 | 82.50651 |
| 8.3 | 128.7714 | 125.90578 | 121.5243 | 112.3185 | 82.57592 |
| 8.3025 | 128.7786 | 125.91298 | 121.5385 | 112.3395 | 82.6384 |
| 8.305 | 128.7927 | 125.92711 | 121.5526 | 112.3605 | 82.70088 |
| 8.3075 | 128.7999 | 125.94124 | 121.5667 | 112.3885 | 82.77029 |
| 8.31 | 128.8141 | 125.94845 | 121.5808 | 112.4095 | 82.83277 |
| 8.3125 | 128.8213 | 125.96265 | 121.5949 | 112.4305 | 82.89526 |
| 8.315 | 128.8354 | 125.97671 | 121.6091 | 112.4584 | 82.95774 |
| 8.3175 | 128.8426 | 125.98392 | 121.6232 | 112.4795 | 83.02715 |
| 8.32 | 128.8568 | 125.99805 | 121.6442 | 112.5005 | 83.08963 |
| 8.3225 | 128.864 | 126.01218 | 121.6583 | 112.5284 | 83.15212 |
| 8.325 | 128.8781 | 126.02631 | 121.6725 | 112.5494 | 83.21461 |
| 8.3275 | 128.8853 | 126.03352 | 121.6866 | 112.5705 | 83.28401 |
| 8.33 | 128.8995 | 126.04765 | 121.7007 | 112.5915 | 83.3465 |
| 8.3325 | 128.9067 | 126.06178 | 121.7148 | 112.6194 | 83.40899 |
| 8.335 | 128.9208 | 126.06899 | 121.7289 | 112.6405 | 83.47147 |
| 8.3375 | 128.928 | 126.08312 | 121.7431 | 112.6615 | 83.53396 |
| 8.34 | 128.9422 | 126.09725 | 121.7572 | 112.6894 | 83.59645 |
| 8.3425 | 128.9494 | 126.11138 | 121.7713 | 112.7104 | 83.65894 |
| 8.345 | 128.9635 | 126.11859 | 121.7923 | 112.7315 | 83.72834 |
| 8.3475 | 128.9707 | 126.13272 | 121.8065 | 112.7525 | 83.79083 |
| 8.35 | 128.9849 | 126.14685 | 121.8206 | 112.7804 | 83.85332 |
| 8.3525 | 128.9921 | 126.15406 | 121.8347 | 112.8015 | 83.91581 |
| 8.355 | 129.0062 | 126.16819 | 121.8488 | 112.8225 | 83.9783 |
| 8.3575 | 129.0134 | 126.18232 | 121.8629 | 112.8435 | 84.04079 |
| 8.36 | 129.0276 | 126.18953 | 121.8771 | 112.8645 | 84.10328 |
| 8.3625 | 129.0348 | 126.20366 | 121.8912 | 112.8925 | 84.16577 |
| 8.365 | 129.0489 | 126.21779 | 121.9053 | 112.9135 | 84.22826 |
| 8.3675 | 129.0561 | 126.22500 | 121.9194 | 112.9345 | 84.29075 |
| 8.37 | 129.0703 | 126.23913 | 121.9336 | 112.9555 | 84.35324 |
| 8.3725 | 129.0775 | 126.25326 | 121.9477 | 112.9835 | 84.40881 |
| 8.375 | 129.0916 | 126.26046 | 121.9618 | 113.0045 | 84.4713 |
| 8.3775 | 129.0988 | 126.27460 | 121.9759 | 113.0255 | 84.53379 |
| 8.38 | 129.1061 | 126.28873 | 121.99 | 113.0465 | 84.59628 |
| 8.3825 | 129.1202 | 126.29593 | 122.0111 | 113.0676 | 84.65877 |
| 8.385 | 129.1274 | 126.31006 | 122.0252 | 113.0886 | 84.72126 |
| 8.3876 | 129.1416 | 126.32419 | 122.0393 | 113.1165 | 84.78375 |
| 8.39 | 129.1488 | 126.33140 | 122.0534 | 113.1376 | 84.83932 |
| 8.3925 | 129.1629 | 126.34553 | 122.0676 | 113.1586 | 84.90182 |
| 8.395 | 129.1701 | 126.35966 | 122.0817 | 113.1796 | 84.96431 |
| 8.3975 | 129.1843 | 126.36687 | 122.0958 | 113.2006 | 85.0268 |
| 8.4 | 129.1915 | 126.38100 | 122.1099 | 113.2217 | 85.08237 |
| 8.4025 | 129.2056 | 126.39513 | 122.124 | 113.2496 | 85.14487 |
| 8.405 | 129.2128 | 126.40234 | 122.1382 | 113.2706 | 85.20736 |
| 8.4075 | 129.227 | 126.41647 | 122.1523 | 113.2916 | 85.26986 |
| 8.41 | 129.2342 | 126.43060 | 122.1664 | 113.3127 | 85.32543 |
| 8.4125 | 129.2414 | 126.43781 | 122.1805 | 113.3337 | 85.38792 |
| 8.415 | 129.2555 | 126.45194 | 122.1947 | 113.3547 | 85.45042 |
| 8.4175 | 129.2627 | 126.46607 | 122.2088 | 113.3757 | 85.50599 |
| 8.42 | 129.2769 | 126.47328 | 122.2229 | 113.3968 | 85.56849 |
| 8.4225 | 129.2841 | 126.48741 | 122.237 | 113.4247 | 85.62406 |
| 8.425 | 129.2982 | 126.50154 | 122.2511 | 113.4457 | 85.68656 |
| 8.4275 | 129.3054 | 126.50875 | 122.2653 | 113.4668 | 85.74213 |
| 8.43 | 129.3196 | 126.52288 | 122.2794 | 113.4878 | 85.80462 |
| 8.4325 | 129.3268 | 126.53701 | 122.2935 | 113.5088 | 85.86712 |
| 8.435 | 129.3409 | 126.54422 | 122.3076 | 113.5298 | 85.92269 |
| 8.4375 | 129.3481 | 126.55835 | 122.3217 | 113.5508 | 85.98519 |
| 8.44 | 129.3554 | 126.57248 | 122.3359 | 113.5719 | 86.04077 |
| 8.4425 | 129.3695 | 126.57969 | 122.35 | 113.5929 | 86.10326 |
| 8.445 | 129.3767 | 126.59382 | 122.3641 | 113.6139 | 86.15884 |
| 8.4475 | 129.3908 | 126.60103 | 122.3782 | 113.6349 | 86.21441 |
| 8.45 | 129.3981 | 126.61516 | 122.3923 | 113.656 | 86.27691 |
| 8.4525 | 129.4122 | 126.62929 | 122.4065 | 113.6839 | 86.33249 |
| 8.455 | 129.4194 | 126.63650 | 122.4206 | 113.7049 | 86.39499 |
| 8.4575 | 129.4336 | 126.65063 | 122.4347 | 113.726 | 86.45056 |
| 8.46 | 129.4408 | 126.66476 | 122.4488 | 113.747 | 86.50614 |
| 8.4625 | 129.448 | 126.67197 | 122.463 | 113.768 | 86.56864 |
| 8.465 | 129.4621 | 126.68610 | 122.4771 | 113.789 | 86.62422 |
| 8.4675 | 129.4693 | 126.70023 | 122.4912 | 113.8101 | 86.67979 |
| 8.47 | 129.4835 | 126.70744 | 122.5053 | 113.8311 | 86.74229 |
| 8.4725 | 129.4907 | 126.72157 | 122.5194 | 113.8521 | 86.79787 |
| 8.475 | 129.5048 | 126.72878 | 122.5336 | 113.8731 | 86.85345 |
| 8.4775 | 129.512 | 126.74291 | 122.5477 | 113.8942 | 86.90903 |
| 8.48 | 129.5192 | 126.75704 | 122.5618 | 113.9152 | 86.97153 |
| 8.4825 | 129.5334 | 126.76425 | 122.5759 | 113.9362 | 87.02711 |
| 8.485 | 129.5406 | 126.77838 | 122.59 | 113.9572 | 87.08268 |
| 8.4875 | 129.5547 | 126.79251 | 122.6042 | 113.9783 | 87.13826 |
| 8.49 | 129.562 | 126.79972 | 122.6183 | 113.9993 | 87.19384 |
| 8.4925 | 129.5761 | 126.81385 | 122.6324 | 114.0203 | 87.25634 |
| 8.495 | 129.5833 | 126.82105 | 122.6465 | 114.0413 | 87.31192 |
| 8.4975 | 129.5905 | 126.83519 | 122.6607 | 114.0624 | 87.3675 |
| 8.5 | 129.6047 | 126.84932 | 122.6748 | 114.0834 | 87.42308 |
| 8.5025 | 129.6119 | 126.85652 | 122.6889 | 114.1044 | 87.47866 |
| 8.505 | 129.626 | 126.87066 | 122.703 | 114.1254 | 87.53424 |
| 8.5075 | 129.6332 | 126.87786 | 122.7171 | 114.1465 | 87.58983 |
| 8.51 | 129.6474 | 126.89199 | 122.7313 | 114.1675 | 87.64541 |
| 8.5125 | 129.6546 | 126.90613 | 122.7454 | 114.1816 | 87.70099 |
| 8.515 | 129.6618 | 126.91333 | 122.7596 | 114.2026 | 87.75657 |
| 8.5175 | 129.6759 | 126.92746 | 122.7667 | 114.2236 | 87.81215 |
| 8.52 | 129.6831 | 126.94160 | 122.7808 | 114.2447 | 87.86773 |
| 8.5225 | 129.6973 | 126.94880 | 122.7949 | 114.2657 | 87.92331 |
| 8.525 | 129.7045 | 128.96293 | 122.8091 | 114.2867 | 87.9789 |
| 8.5275 | 129.7117 | 126.97014 | 122.8232 | 114.3077 | 88.03448 |
| 8.53 | 129.7258 | 126.98427 | 122.8373 | 114.3288 | 88.09006 |
| 8.5325 | 129.7331 | 126.99840 | 122.8514 | 114.3498 | 88.14564 |
| 8.535 | 129.7472 | 127.00561 | 122.8656 | 114.3708 | 88.20123 |
| 8.5375 | 129.7544 | 127.01974 | 122.8797 | 114.3918 | 88.25681 |
| 8.54 | 129.7616 | 127.02695 | 122.8938 | 114.4129 | 88.30547 |
| 8.5425 | 129.7758 | 127.04108 | 122.9079 | 114.4339 | 88.36105 |
| 8.545 | 129.783 | 127.04829 | 122.922 | 114.448 | 88.41664 |
| 8.5475 | 129.7971 | 127.06242 | 122.9362 | 114.469 | 88.47222 |
| 8.55 | 129.8043 | 127.07655 | 122.9503 | 114.4901 | 88.52781 |
| 8.5525 | 129.8185 | 127.08376 | 122.9644 | 114.5111 | 88.57647 |
| 8.555 | 129.8257 | 127.09789 | 122.9785 | 114.5321 | 88.63205 |
| 8.5575 | 129.8329 | 127.10510 | 122.9857 | 114.5531 | 88.68764 |
| 8.56 | 129.847 | 127.11923 | 122.9999 | 114.5742 | 88.74322 |
| 8.5625 | 129.8542 | 127.13336 | 123.014 | 114.5952 | 88.79188 |
| 8.565 | 129.8684 | 127.14057 | 123.0281 | 114.6093 | 88.84747 |
| 8.5675 | 129.8756 | 127.15470 | 123.0422 | 114.6303 | 88.90306 |
| 8.57 | 129.8828 | 127.16191 | 123.0563 | 114.6513 | 88.95172 |
| 8.5725 | 129.8969 | 127.17604 | 123.0705 | 114.6724 | 89.0073 |
| 8.575 | 129.9042 | 127.18325 | 123.0846 | 114.6934 | 89.06289 |
| 8.5775 | 129.9114 | 127.19738 | 123.0987 | 114.7144 | 89.11155 |
| 8.58 | 129.9255 | 127.21151 | 123.1128 | 114.7355 | 89.16714 |
| 8.5825 | 129.9327 | 127.21872 | 123.1269 | 114.7496 | 89.22273 |
| 8.585 | 129.9469 | 127.23285 | 123.1341 | 114.7706 | 89.27139 |
| 8.5875 | 129.9541 | 127.24006 | 123.1483 | 114.7916 | 89.32698 |
| 8.59 | 129.9613 | 127.25419 | 123.1624 | 114.8126 | 89.37564 |
| 8.5925 | 129.9754 | 127.26832 | 123.1765 | 114.8337 | 89.43123 |
| 8.595 | 129.9826 | 127.27553 | 123.1906 | 114.8478 | 89.4799 |
| 8.5975 | 129.9968 | 127.28966 | 123.2048 | 114.8688 | 89.53548 |
| 8.6 | 130.004 | 127.29687 | 123.2189 | 114.8898 | 89.58415 |
| 8.6025 | 130.0112 | 127.31100 | 123.233 | 114.9108 | 89.63974 |
| 8.605 | 130.0253 | 127.31821 | 123.2471 | 114.9319 | 89.6884 |
| 8.6075 | 130.0326 | 127.33234 | 123.2543 | 114.9529 | 89.74399 |
| 8.61 | 130.0467 | 127.33955 | 123.2684 | 114.967 | 89.79266 |
| 8.6125 | 130.0539 | 127.35368 | 123.2826 | 114.988 | 89.84825 |
| 8.615 | 130.0611 | 127.36781 | 123.2967 | 115.0091 | 89.89691 |
| 8.6175 | 130.0753 | 127.37502 | 123.3108 | 115.0301 | 89.94558 |
| 8.62 | 130.0825 | 127.38915 | 123.3249 | 115.0442 | 90.00117 |
| 8.6225 | 130.0897 | 127.39636 | 123.3391 | 115.0652 | 90.04984 |
| 8.625 | 130.1038 | 127.41049 | 123.3532 | 115.0862 | 90.0985 |
| 8.8275 | 130.111 | 127.41769 | 123.3673 | 115.1073 | 90.15409 |
| 8.63 | 130.1252 | 127.43183 | 123.3745 | 115.1283 | 90.20276 |
| 8.6325 | 130.1324 | 127.43903 | 123.3886 | 115.1424 | 90.25143 |
| 8.635 | 130.1396 | 127.45317 | 123.4027 | 115.1634 | 90.30702 |
| 8.6375 | 130.1537 | 127.46730 | 123.4169 | 115.1845 | 90.35569 |
| 8.64 | 130.1609 | 127.47450 | 123.431 | 115.2055 | 90.40436 |
| 8.6425 | 130.1682 | 127.48864 | 123.4451 | 115.2196 | 90.45302 |
| 8.645 | 130.1823 | 127.49584 | 123.4592 | 115.2406 | 90.50862 |
| 8.6475 | 130.1895 | 127.50997 | 123.4664 | 115.2617 | 90.55729 |
| 8.65 | 130.2036 | 127.51718 | 123.4806 | 115.2827 | 90.60595 |
| 8.6525 | 130.2109 | 127.53131 | 123.4947 | 115.2968 | 90.65462 |
| 8.655 | 130.2181 | 127.53852 | 123.5088 | 115.3178 | 90.70329 |
| 8.6575 | 130.2322 | 127.55265 | 123.5229 | 115.3388 | 90.75196 |
| 8.66 | 130.2394 | 127.55986 | 123.537 | 115.3529 | 90.80755 |
| 8.6625 | 130.2466 | 127.57399 | 123.5512 | 115.374 | 90.85622 |
| 8.665 | 130.2608 | 127.58812 | 123.5584 | 115.395 | 90.90489 |

APPENDIX 1-continued

Standard Mass Calculation

| Pressure | 15.1 | 17.2 | Temps 20.1 C. | 25.1 C. | 35.1 C. |
|---|---|---|---|---|---|
| 8.6675 | 130.268 | 127.59533 | 123.5725 | 115.416 | 90.95356 |
| 8.67 | 130.2752 | 127.60946 | 123.5866 | 115.4301 | 91.00223 |
| 8.6725 | 130.2893 | 127.61667 | 123.6007 | 115.4512 | 91.0509 |
| 8.675 | 130.2966 | 127.63080 | 123.6149 | 115.4722 | 91.09958 |
| 8.6775 | 130.3107 | 127.63801 | 123.629 | 115.4863 | 91.14825 |
| 8.68 | 130.3179 | 127.65214 | 123.6362 | 115.5073 | 91.19692 |
| 8.6825 | 130.3251 | 127.65935 | 123.6503 | 115.5284 | 91.24559 |
| 8.685 | 130.3393 | 127.67348 | 123.6644 | 115.5425 | 91.29426 |
| 8.6875 | 130.3465 | 127.68069 | 123.6785 | 115.5635 | 91.34293 |
| 8.69 | 130.3537 | 127.69482 | 123.6927 | 115.5845 | 91.3916 |
| 8.6925 | 130.3678 | 127.70203 | 123.7068 | 115.6055 | 91.44027 |
| 8.695 | 130.375 | 127.71616 | 123.7209 | 115.6196 | 91.48895 |
| 8.6975 | 130.3823 | 127.72337 | 123.7281 | 115.6407 | 91.53762 |
| 8.7 | 130.3964 | 127.73750 | 123.7422 | 115.6617 | 91.58629 |
| 8.7025 | 130.4036 | 127.75163 | 123.7564 | 115.6758 | 91.63496 |
| 8.705 | 130.4108 | 127.75884 | 123.7705 | 115.6968 | 91.68364 |
| 8.7075 | 130.425 | 127.77297 | 123.7846 | 115.7179 | 91.72538 |
| 8.71 | 130.4322 | 127.78018 | 123.7918 | 115.732 | 91.77406 |
| 8.7125 | 130.4463 | 127.79431 | 123.8059 | 115.753 | 91.82273 |
| 8.715 | 130.4535 | 127.80152 | 123.8201 | 115.7671 | 91.8714 |
| 8.7175 | 130.4607 | 127.81565 | 123.8342 | 115.7881 | 91.92008 |
| 8.72 | 130.4749 | 127.82286 | 123.8480 | 115.8092 | 91.96875 |
| 8.7225 | 130.4821 | 127.83699 | 123.8624 | 115.8233 | 92.0105 |
| 8.725 | 130.4893 | 127.84419 | 123.8696 | 115.8443 | 92.05918 |
| 8.7275 | 130.5034 | 127.85833 | 123.8837 | 115.8653 | 92.10785 |
| 8.73 | 130.5106 | 127.86553 | 123.8979 | 115.8794 | 92.15653 |
| 8.7325 | 130.5179 | 127.87967 | 123.912 | 115.9005 | 92.19828 |
| 8.735 | 130.532 | 127.88687 | 123.9261 | 115.9215 | 92.24695 |
| 8.7375 | 130.5392 | 127.90101 | 123.9333 | 115.9356 | 92.29563 |
| 8.74 | 130.5464 | 127.90821 | 123.9474 | 115.9566 | 92.33738 |
| 8.7425 | 130.5606 | 127.92234 | 123.9616 | 115.9707 | 92.38605 |
| 8.745 | 130.5678 | 127.92955 | 123.9757 | 115.9918 | 92.43473 |
| 8.7475 | 130.575 | 127.94368 | 123.9898 | 116.0128 | 92.47648 |
| 8.75 | 130.5891 | 127.95089 | 123.997 | 116.0269 | 92.52515 |
| 8.7525 | 130.5963 | 127.96502 | 124.0111 | 116.0479 | 92.57383 |
| 8.755 | 130.6036 | 127.97223 | 124.0252 | 116.062 | 92.61558 |
| 8.7575 | 130.61771 | 127.98636 | 124.0394 | 116.0831 | 92.66426 |
| 8.76 | 130.6249 | 127.99357 | 124.0535 | 116.1041 | 92.70601 |
| 8.7625 | 130.6321 | 128.00770 | 124.0607 | 116.1182 | 92.75469 |
| 8.765 | 130.6463 | 128.01491 | 124.0748 | 116.1392 | 92.80336 |
| 8.7675 | 130.6535 | 128.02904 | 124.0889 | 116.1533 | 92.84512 |
| 8.77 | 130.6607 | 128.03625 | 124.1031 | 116.1744 | 92.89379 |
| 8.7725 | 130.6748 | 128.05038 | 124.1103 | 116.1954 | 92.93555 |
| 8.775 | 130.682 | 128.05759 | 124.1244 | 116.2095 | 92.98423 |
| 8.7775 | 130.6892 | 128.07172 | 124.1385 | 116.2305 | 93.02598 |
| 8.78 | 130.7034 | 128.07893 | 124.1526 | 116.2446 | 93.07466 |
| 8.7825 | 130.7106 | 128.09306 | 124.1668 | 116.2657 | 93.11641 |
| 8.785 | 130.7178 | 128.10027 | 124.174 | 116.2798 | 93.16509 |
| 8.7875 | 130.7319 | 128.11440 | 124.1881 | 116.3008 | 93.20684 |
| 8.79 | 130.7392 | 128.12161 | 124.2022 | 118.3149 | 93.2486 |
| 8.7925 | 130.7464 | 128.13574 | 124.2163 | 118.3359 | 93.29728 |
| 8.795 | 130.7605 | 128.14294 | 124.2235 | 116.357 | 93.33903 |
| 8.7975 | 130.7677 | 128.15708 | 124.2376 | 116.3711 | 93.38771 |
| 8.8 | 130.7749 | 128.16428 | 124.2518 | 116.3921 | 93.42946 |
| 8.8025 | 130.7891 | 128.17842 | 124.2659 | 116.4062 | 93.47122 |
| 8.805 | 130.7963 | 128.18562 | 124.28 | 116.4273 | 93.5199 |
| 8.8075 | 130.8035 | 128.19283 | 124.2872 | 116.4414 | 93.56165 |
| 8.81 | 130.8176 | 128.20696 | 124.3013 | 116.4624 | 93.60341 |
| 8.8125 | 130.8248 | 128.21417 | 124.3155 | 116.4765 | 93.65209 |
| 8.815 | 130.8321 | 128.22830 | 124.3296 | 116.4975 | 93.69384 |
| 8.8175 | 130.8393 | 128.23551 | 124.3368 | 116.5116 | 93.7356 |
| 8.82 | 130.8534 | 128.24964 | 124.3509 | 116.5327 | 93.78428 |
| 8.8225 | 130.8606 | 128.25685 | 124.365 | 116.5468 | 93.82604 |
| 8.825 | 130.8678 | 128.27098 | 124.3792 | 116.5678 | 93.86779 |
| 8.8276 | 130.882 | 128.27819 | 124.3864 | 116.5819 | 93.90955 |
| 8.83 | 130.8892 | 123.29232 | 124.4005 | 116.6029 | 93.95823 |
| 8.8325 | 130.8964 | 128.29953 | 124.4146 | 116.617 | 93.99999 |
| 8.835 | 130.9105 | 128.31366 | 124.4287 | 116.6381 | 94.04174 |
| 8.8375 | 130.9178 | 128.32087 | 124.4359 | 116.6522 | 94.0835 |
| 8.84 | 130.925 | 128.33500 | 124.45 | 116.6732 | 94.12526 |
| 8.8425 | 130.9391 | 128.34221 | 124.4642 | 116.6873 | 94.17394 |
| 8.845 | 130.9463 | 128.35634 | 124.4783 | 116.7084 | 94.2157 |
| 8.8475 | 130.9535 | 128.36354 | 124.4855 | 116.7225 | 94.25746 |
| 8.85 | 130.9607 | 128.37075 | 124.4996 | 116.7435 | 94.29921 |
| 8.8525 | 130.9749 | 128.38488 | 124.5137 | 116.7576 | 94.34097 |
| 8.855 | 130.9821 | 128.39209 | 124.5279 | 116.7786 | 94.38273 |
| 8.8575 | 130.9893 | 128.40622 | 124.5351 | 116.7927 | 94.42449 |
| 8.86 | 131.0034 | 128.41343 | 124.5492 | 116.8138 | 94.46625 |
| 8.8625 | 131.0107 | 128.42756 | 124.5633 | 116.8279 | 94.508 |
| 8.865 | 131.0179 | 128.43477 | 124.5705 | 116.8489 | 94.55669 |
| 8.8675 | 131.032 | 128.44890 | 124.5848 | 116.863 | 94.59845 |
| 8.87 | 131.0392 | 128.45611 | 124.5988 | 116.884 | 94.64021 |
| 8.8725 | 131.0464 | 128.47024 | 124.6129 | 116.8982 | 94.68197 |
| 8.875 | 131.0536 | 128.47745 | 124.6201 | 116.9192 | 94.72372 |
| 8.8775 | 131.0678 | 128.48466 | 124.6342 | 116.9333 | 94.76548 |
| 8.88 | 131.075 | 128.49879 | 124.6483 | 116.9474 | 94.80724 |
| 8.8825 | 131.0822 | 128.50599 | 124.6624 | 116.9684 | 94.849 |
| 8.885 | 131.0963 | 128.52013 | 124.6696 | 116.9825 | 94.89076 |
| 8.8875 | 131.1036 | 128.52733 | 124.6838 | 117.0036 | 94.93252 |
| 8.89 | 131.1108 | 128.54147 | 124.6979 | 117.0177 | 94.96736 |
| 8.8925 | 131.1249 | 128.54867 | 124.7051 | 117.0387 | 95.00912 |
| 8.895 | 131.1321 | 128.56281 | 124.7192 | 117.0528 | 95.05088 |
| 8.8975 | 131.1393 | 128.57001 | 124.7333 | 117.0669 | 95.09264 |
| 8.9 | 131.1465 | 128.58415 | 124.7475 | 117.088 | 95.1344 |
| 8.9025 | 131.1607 | 128.59135 | 124.7647 | 117.1021 | 95.17616 |
| 8.905 | 131.1679 | 128.59856 | 124.7688 | 117.1231 | 95.21792 |
| 8.9075 | 131.1751 | 128.61269 | 124.7829 | 117.1372 | 95.25968 |
| 8.91 | 131.1892 | 128.61990 | 124.7901 | 117.1582 | 95.30144 |
| 8.9125 | 131.1965 | 128.63403 | 124.8042 | 117.1723 | 95.33628 |
| 8.915 | 131.2037 | 128.64124 | 124.8184 | 117.1865 | 95.37804 |
| 8.9175 | 131.2109 | 128.65537 | 124.8256 | 117.2075 | 95.4198 |
| 8.92 | 131.225 | 128.66258 | 124.8397 | 117.2216 | 95.46157 |
| 8.9225 | 131.2322 | 128.66978 | 124.8538 | 117.2426 | 95.50333 |
| 8.925 | 131.2395 | 128.68392 | 124.8679 | 117.2567 | 95.54509 |
| 8.9275 | 131.2536 | 128.69112 | 124.8751 | 117.2708 | 95.57993 |
| 8.93 | 131.2608 | 128.70526 | 124.8893 | 117.2919 | 95.62169 |
| 8.9325 | 131.268 | 128.71246 | 124.9034 | 117.306 | 95.66345 |
| 8.935 | 131.2752 | 128.72660 | 124.9106 | 117.327 | 95.70521 |
| 8.9375 | 131.2894 | 128.73380 | 124.9247 | 117.3411 | 95.74005 |
| 8.94 | 131.2966 | 128.74101 | 124.9388 | 117.3552 | 95.78181 |
| 8.9425 | 131.3038 | 128.75514 | 124.946 | 117.3763 | 95.82358 |
| 8.945 | 131.3179 | 128.76235 | 124.9601 | 117.3904 | 95.85842 |
| 8.9475 | 131.3251 | 128.77648 | 124.9743 | 117.4114 | 95.90018 |
| 8.95 | 131.3324 | 128.78369 | 124.9884 | 117.4255 | 95.94194 |
| 8.9525 | 131.3396 | 128.79782 | 124.9956 | 117.4396 | 95.97678 |
| 8.955 | 131.3537 | 128.80503 | 125.0097 | 117.4607 | 96.01854 |
| 8.9575 | 131.3609 | 128.81223 | 125.0238 | 117.4748 | 96.06031 |
| 8.96 | 131.3681 | 128.82637 | 125.031 | 117.4889 | 96.09515 |
| 8.9625 | 131.3753 | 128.83357 | 125.0452 | 117.5099 | 96.13691 |
| 8.965 | 131.3895 | 128.84771 | 125.0593 | 117.524 | 96.17868 |
| 8.9675 | 131.3967 | 128.85491 | 125.0665 | 117.5381 | 96.21352 |
| 8.97 | 131.4039 | 128.86905 | 125.0806 | 117.5692 | 96.25528 |
| 8.725 | 131.418 | 128.87625 | 125.0947 | 117.5733 | 96.29012 |
| 8.975 | 131.4253 | 128.88346 | 125.1019 | 117.5874 | 96.33188 |
| 8.9775 | 131.4325 | 128.89759 | 125.1161 | 117.6084 | 96.36672 |
| 8.98 | 131.4397 | 128.90480 | 125.1302 | 117.6225 | 96.40849 |
| 8.9825 | 131.4538 | 128.91893 | 125.1374 | 117.6435 | 96.45025 |
| 8.985 | 131.461 | 128.92614 | 125.1515 | 117.6577 | 96.48509 |
| 8.9875 | 131.4682 | 128.93334 | 125.1656 | 117.6718 | 96.52686 |
| 8.99 | 131.4755 | 128.94748 | 125.1728 | 117.6928 | 96.5617 |
| 8.9925 | 131.4896 | 123.95468 | 125.187 | 117.7069 | 96.60347 |
| 8.995 | 131.4968 | 128.96882 | 125.2011 | 117.721 | 96.63831 |
| 8.9975 | 131.504 | 128.97602 | 125.2083 | 117.742 | 96.68007 |
| 9 | 131.5112 | 128.98323 | 125.2224 | 117.7562 | 96.71491 |

APPENDIX 2

Reverse Pressure lookup

| | | Temp 17.2 C. | 20.1 C. | 25.1 C. | 35.1 C. |
|---|---|---|---|---|---|
| Mass | 30.0 | | 5.005 | 5.1975 | 5.575 |
| | 30.1 | | 5.0125 | 5.205 | 5.5875 |

APPENDIX 2-continued

Reverse Pressure lookup

| | Temp | | | |
|---|---|---|---|---|
| | 17.2 C. | 20.1 C. | 25.1 C. | 35.1 C. |
| 30.2 | | 5.0225 | 5.215 | 5.5975 |
| 30.3 | | 5.03 | 5.225 | 5.6075 |
| 30.4 | | 5.0375 | 5.2325 | 5.6175 |
| 30.5 | | 5.045 | 5.2425 | 5.6275 |
| 30.6 | | 5.055 | 5.25 | 5.64 |
| 30.7 | | 5.0625 | 5.26 | 5.65 |
| 30.8 | | 5.07 | 5.2675 | 5.66 |
| 30.9 | | 5.0775 | 5.2775 | 5.67 |
| 31.0 | | 5.085 | 5.285 | 5.68 |
| 31.1 | | 5.0925 | 5.295 | 5.69 |
| 31.2 | | 5.1 | 5.3025 | 5.7 |
| 31.3 | | 5.11 | 5.3125 | 5.71 |
| 31.4 | | 5.1175 | 5.32 | 5.72 |
| 31.5 | 5.005 | 5.125 | 5.3275 | 5.73 |
| 31.6 | 5.0125 | 5.1325 | 5.3375 | 5.7425 |
| 31.7 | 5.02 | 5.14 | 5.345 | 5.7525 |
| 31.8 | 5.025 | 5.1475 | 5.355 | 5.7625 |
| 31.9 | 5.0325 | 5.155 | 5.3625 | 5.77 |
| 32.0 | 5.04 | 5.1625 | 5.37 | 5.78 |
| 32.1 | 5.0475 | 5.17 | 5.38 | 5.79 |
| 32.2 | 5.055 | 5.1775 | 5.3875 | 5.8 |
| 32.3 | 5.06 | 5.135 | 5.395 | 5.81 |
| 32.4 | 5.0675 | 5.1925 | 5.4025 | 5.82 |
| 32.5 | 5.075 | 5.2 | 5.4125 | 5.83 |
| 32.6 | 5.08 | 5.205 | 5.42 | 5.84 |
| 32.7 | 5.0875 | 5.2125 | 5.4275 | 5.85 |
| 32.8 | 5.095 | 5.22 | 5.435 | 5.86 |
| 32.9 | 5.1 | 5.2275 | 5.4425 | 5.8675 |
| 33.0 | 5.1075 | 5.235 | 5.4525 | 5.8775 |
| 33.1 | 5.115 | 5.2425 | 5.46 | 5.8875 |
| 33.2 | 5.12 | 5.25 | 5.4675 | 5.8975 |
| 33.3 | 5.1275 | 5.255 | 5.475 | 5.9075 |
| 33.4 | 5.1325 | 5.2625 | 5.4825 | 5.915 |
| 33.5 | 5.14 | 5.27 | 5.49 | 5.925 |
| 33.6 | 5.1475 | 5.2775 | 5.4975 | 5.935 |
| 33.7 | 5.1525 | 5.2825 | 5.505 | 5.945 |
| 33.8 | 5.16 | 5.29 | 5.5125 | 5.9525 |
| 33.9 | 5.165 | 5.2975 | 5.52 | 5.9625 |
| 34.0 | 5.1725 | 5.3025 | 5.5275 | 5.9725 |
| 34.1 | 5.1775 | 5.31 | 5.535 | 5.98 |
| 34.2 | 5.185 | 5.3175 | 5.5425 | 5.99 |
| 34.3 | 5.19 | 5.3225 | 5.55 | 6 |
| 34.4 | 5.195 | 5.33 | 5.5575 | 6.0075 |
| 34.5 | 5.2025 | 5.3375 | 5.565 | 6.0175 |
| 34.6 | 5.2075 | 5.3425 | 5.5725 | 6.025 |
| 34.7 | 5.215 | 5.35 | 5.58 | 6.035 |
| 34.8 | 5.22 | 5.355 | 5.5875 | 6.045 |
| 34.9 | 5.225 | 5.3625 | 5.595 | 6.0525 |
| 35.0 | 5.2325 | 5.3675 | 5.6025 | 6.0625 |
| 35.1 | 5.2375 | 5.375 | 5.61 | 6.07 |
| 35.2 | 5.2425 | 5.38 | 5.6175 | 6.08 |
| 35.3 | 5.2475 | 5.3375 | 5.6225 | 6.0875 |
| 35.4 | 5.255 | 5.3925 | 5.63 | 6.0975 |
| 35.5 | 5.26 | 5.4 | 5.6375 | 6.105 |
| 35.6 | 5.265 | 5.405 | 5.645 | 6.115 |
| 35.7 | 5.2725 | 5.4125 | 5.6525 | 6.1225 |
| 35.8 | 5.2775 | 5.4175 | 5.6575 | 6.13 |
| 35.9 | 5.2825 | 5.425 | 5.665 | 6.14 |
| 36.0 | 5.2875 | 5.43 | 5.6725 | 6.1475 |
| 36.1 | 5.2925 | 5.435 | 5.68 | 6.1575 |
| 36.2 | 5.2975 | 5.4425 | 5.685 | 6.165 |
| 36.3 | 5.305 | 5.4475 | 5.6925 | 6.1725 |
| 36.4 | 5.31 | 5.4525 | 5.7 | 6.1825 |
| 36.5 | 5.315 | 5.46 | 5.705 | 6.19 |
| 36.6 | 5.32 | 5.465 | 5.7125 | 6.1975 |
| 36.7 | 5.325 | 5.47 | 5.72 | 6.2075 |
| 36.8 | 5.33 | 5.4775 | 5.725 | 6.215 |
| 36.9 | 5.335 | 5.4825 | 5.7125 | 6.2225 |
| 37.0 | 5.34 | 5.4875 | 5.74 | 6.2325 |
| 37.1 | 5.345 | 5.4925 | 5.7451 | 6.24 |
| 37.2 | 5.35 | 5.5 | 5.7525 | 6.2475 |
| 37.3 | 5.355 | 5.505 | 5.7575 | 6.255 |
| 37.4 | 5.36 | 5.51 | 5.765 | 6.265 |
| 37.5 | 5.365 | 5.515 | 5.77 | 6.2725 |

APPENDIX 2-continued

Reverse Pressure lookup

| | Temp | | | |
|---|---|---|---|---|
| | 17.2 C. | 20.1 C. | 25.1 C. | 35.1 C. |
| 37.6 | 5.37 | 5.52 | 5.7775 | 6.28 |
| 37.7 | 5.375 | 5.5275 | 5.7825 | 6.2875 |
| 37.8 | 5.38 | 5.5325 | 5.79 | 6.295 |
| 37.9 | 5.335 | 5.5375 | 5.795 | 6.305 |
| 38.0 | 5.39 | 5.5425 | 5.8025 | 6.3125 |
| 36.1 | 5.395 | 5.54.75 | 5.8075 | 6.32 |
| 38.2 | 5.4 | 5.5525 | 5.815 | 6.3275 |
| 38.3 | 5.405 | 5.5575 | 5.82 | 6.335 |
| 38.4 | 5.41 | 5.5625 | 5.8275 | 6.3425 |
| 38.5 | 5.4125 | 5.5675 | 5.8325 | 6.35 |
| 38.6 | 5.4175 | 5.5725 | 5.8375 | 6.3575 |
| 38.7 | 5.4225 | 5.58 | 5.845 | 6.3675 |
| 38.8 | 5.4275 | 5.585 | 5.85 | 6.375 |
| 38.9 | 5.4325 | 5.59 | 5.8575 | 6.3825 |
| 39.0 | 5.4375 | 5.595 | 5.8625 | 6.39 |
| 39.1 | 5.44 | 5.6 | 5.8675 | 6.3975 |
| 39.2 | 5.445 | 5.605 | 5.875 | 6.405 |
| 39.3 | 5.45 | 5.6075 | 5.88 | 6.4125 |
| 39.4 | 5.455 | 5.6125 | 5.385 | 6.42 |
| 39.5 | 5.4575 | 5.6175 | 5.8925 | 6.4275 |
| 39.6 | 5.4625 | 5.6225 | 5.8975 | 6.435 |
| 39.7 | 5.4675 | 5.6275 | 5.9025 | 6.4425 |
| 39.8 | 5.47 | 5.6325 | 5.9075 | 6.45 |
| 39.9 | 5.475 | 5.6375 | 5.915 | 6.4575 |
| 40.0 | 5.48 | 5.6425 | 5.92 | 6.4625 |
| 40.1 | 5.4825 | 5.6475 | 5.925 | 6.47 |
| 40.2 | 5.4875 | 5.6525 | 5.93 | 6.4775 |
| 40.3 | 5.4925 | 5.655 | 5.935 | 6.485 |
| 40.4 | 5.495 | 5.66 | 5.9425 | 6.4925 |
| 40.5 | 5.5 | 5.665 | 5.9475 | 6.5 |
| 40.6 | 5.505 | 5.67 | 5.9525 | 6.5075 |
| 40.7 | 5.5075 | 5.675 | 5.9575 | 6.515 |
| 40.8 | 5.5125 | 5.68 | 5.9625 | 6.52 |
| 40.9 | 5.515 | 5.6825 | 5.9675 | 6.5275 |
| 41.0 | 5.52 | 5.6875 | 5.975 | 6.535 |
| 41.1 | 5.5225 | 5.6925 | 5.98 | 6.5425 |
| 41.2 | 5.5275 | 5.6975 | 5.985 | 6.55 |
| 41.3 | 5.53 | 5.7 | 5.99 | 6.555 |
| 41.4 | 5.535 | 5.705 | 5.995 | 6.5625 |
| 41.5 | 5.5375 | 5.71 | 6 | 6.57 |
| 41.6 | 5.5425 | 5.7125 | 6.005 | 6.5775 |
| 41.7 | 5.545 | 5.7175 | 6.01 | 6.585 |
| 41.8 | 5.55 | 5.7225 | 6.015 | 6.59 |
| 41.9 | 5.5525 | 5.725 | 6.02 | 6.5975 |
| 42.0 | 5.5575 | 5.73 | 6.025 | 6.605 |
| 42.1 | 5.56 | 5.735 | 6.03 | 6.61 |
| 42.2 | 5.565 | 5.7375 | 6.035 | 6.6175 |
| 42.3 | 5.5675 | 5.7425 | 6.04 | 6.625 |
| 42.4 | 5.57 | 5.7475 | 6.045 | 6.63 |
| 42.5 | 5.575 | 5.75 | 6.05 | 6.6375 |
| 42.6 | 5.5775 | 5.755 | 6.055 | 6.645 |
| 42.7 | 5.5825 | 5.7575 | 6.06 | 6.65 |
| 42.8 | 5.585 | 5.7625 | 6.065 | 6.6575 |
| 42.9 | 5.5875 | 5.765 | 6.07 | 6.665 |
| 43.0 | 5.5925 | 5.77 | 6.075 | 6.67 |
| 43.1 | 5.595 | 5.775 | 6.08 | 6.8775 |
| 43.2 | 5.5975 | 5.7775 | 6.0825 | 6.6825 |
| 43.3 | 5.6 | 5.7825 | 6.0875 | 6.69 |
| 43.4 | 5.605 | 5.735 | 6.0925 | 6.6975 |
| 43.5 | 5.6075 | 5.79 | 6.0975 | 6.7025 |
| 43.6 | 5.61 | 5.7925 | 6.1025 | 6.71 |
| 43.7 | 5.615 | 5.7975 | 6.1075 | 6.715 |
| 43.8 | 5.6175 | 5.8 | 6.1125 | 6.7225 |
| 43.9 | 5.62 | 5.8025 | 6.115 | 6.7275 |
| 44.0 | 5.6225 | 5.8075 | 6.12 | 6.735 |
| 44.1 | 5.6275 | 5.81 | 6.125 | 6.74 |
| 44.2 | 5.63 | 5.815 | 6.13 | 6.7475 |
| 44.3 | 5.6325 | 5.8175 | 6.135 | 6.7525 |
| 44.4 | 5.635 | 5.8225 | 6.1375 | 6.713 |
| 44.5 | 5.6375 | 5.825 | 6.1425 | 6.765 |
| 44.6 | 5.64 | 5.8275 | 6.1475 | 6.7725 |
| 44.7 | 5.645 | 5.8325 | 6.1525 | 6.7775 |
| 44.8 | 5.6475 | 5.835 | 6.155 | 6.785 |
| 44.9 | 5.65 | 5.84 | 6.16 | 6.79 |

APPENDIX 2-continued

Reverse Pressure lookup

| | Temp | | | |
|---|---|---|---|---|
| | 17.2 C. | 20.1 C. | 25.1 C. | 35.1 C. |
| 45.0 | 5.6525 | 5.8425 | 6.165 | 6.795 |
| 45.1 | 5.655 | 5.845 | 6.1675 | 6.8925 |
| 45.2 | 5.6575 | 5.85 | 6.1725 | 6.8075 |
| 45.3 | 5.66 | 5.8525 | 6.1775 | 6.815 |
| 45.4 | 5.665 | 5.855 | 6.1825 | 6.132 |
| 45.5 | 5.6675 | 5.8575 | 6.185 | 6.825 |
| 45.6 | 5.67 | 5.8625 | 6.19 | 6.8325 |
| 45.7 | 5.6725 | 5.865 | 6.195 | 6.8375 |
| 45.8 | 5.675 | 5.8675 | 6.1975 | 6.845 |
| 45.9 | 5.6775 | 5.8725 | 6.2025 | 6.85 |
| 46.0 | 5.68 | 5.875 | 6.205 | 6.855 |
| 46.1 | 5.6825 | 5.8775 | 6.21 | 6.8625 |
| 46.2 | 5.685 | 5.88 | 6.215 | 6.8675 |
| 46.3 | 5.6875 | 5.885 | 6.2175 | 6.8725 |
| 46.4 | 5.69 | 5.8375 | 6.2225 | 6.8775 |
| 46.5 | 5.6925 | 5.89 | 6.225 | 6.885 |
| 46.6 | 5.695 | 5.8925 | 6.23 | 6.89 |
| 46.7 | 5.6975 | 5.895 | 6.235 | 6.895 |
| 46.8 | 5.7 | 5.9 | 6.2375 | 6.9025 |
| 46.9 | 5.7025 | 5.9025 | 6.2425 | 6.9075 |
| 47.0 | 5.705 | 5.905 | 6.245 | 6.9125 |
| 47.1 | 5.7075 | 5.9075 | 6.25 | 6.9175 |
| 47.2 | 5.71 | 5.91 | 6.2525 | 6.925 |
| 47.3 | 5.7125 | 5.9125 | 6.2575 | 6.93 |
| 47.4 | 5.715 | 5.9175 | 6.26 | 6.935 |
| 47.5 | 5.7175 | 5.92 | 6.265 | 6.94 |
| 47.6 | 5.7175 | 5.9225 | 6.2675 | 6.945 |
| 47.7 | 5.72 | 5.925 | 6.2725 | 6.9525 |
| 47.8 | 5.7225 | 5.9275 | 6.275 | 6.9575 |
| 47.9 | 5.725 | 5.93 | 6.28 | 6.9625 |
| 48.0 | 5.7275 | 5.9325 | 6.2825 | 6.9675 |
| 48.1 | 5.73 | 5.935 | 6.2875 | 6.9725 |
| 48.2 | 5.7325 | 5.9375 | 6.29 | 6.98 |
| 48.3 | 5.735 | 5.94 | 6.2925 | 6.985 |
| 48.4 | 5.735 | 5.9425 | 6.2975 | 6.99 |
| 48.5 | 5.7375 | 5.9475 | 6.3 | 6.995 |
| 48.6 | 5.74 | 5.95 | 6.305 | 7 |
| 48.7 | 5.7425 | 5.9525 | 6.3075 | 7.005 |
| 48.8 | 5.745 | 5.955 | 6.31 | 7.01 |
| 48.9 | 5.745 | 5.9575 | 6.315 | 7.015 |
| 49.0 | 5.7475 | 5.96 | 6.3175 | 7.0225 |
| 49.1 | 5.75 | 5.9625 | 6.3225 | 7.0275 |
| 49.2 | 5.7525 | 5.965 | 6.325 | 7.0325 |
| 49.3 | 5.755 | 5.9675 | 6.3275 | 7.0375 |
| 49.4 | 5.755 | 5.97 | 6.3325 | 7.0425 |
| 49.5 | 5.7575 | 5.9725 | 6.335 | 7.0475 |
| 49.6 | 5.76 | 5.975 | 6.3375 | 7.0525 |
| 49.7 | 5.7625 | 5.9775 | 6.3425 | 7.0575 |
| 49.8 | 5.7625 | 5.9775 | 6.345 | 7.0625 |
| 49.9 | 5.765 | 5.93 | 6.3475 | 7.0675 |
| 50.0 | 5.7675 | 5.9825 | 6.3525 | 7.0725 |
| 50.1 | 5.77 | 5.985 | 6.355 | 7.0775 |
| 50.2 | 5.77 | 5.9875 | 6.3575 | 7.0825 |
| 50.3 | 5.7725 | 5.99 | 6.36 | 7.0875 |
| 50.4 | 5.775 | 5.9925 | 6.3135 | 7.0925 |
| 50.5 | 5.775 | 5.995 | 6.3675 | 7.0975 |
| 50.6 | 5.7775 | 5.9975 | 6.37 | 7.1025 |
| 50.7 | 5.78 | 6 | 6.375 | 7.1075 |
| 50.8 | 5.78 | 6.0025 | 6.3775 | 7.1125 |
| 50.9 | 5.7825 | 6.005 | 6.38 | 7.1175 |
| 51.0 | 5.785 | 6.005 | 6.3825 | 7.1225 |
| 51.1 | 5.785 | 6.0075 | 6.3875 | 7.1275 |
| 51.2 | 5.7875 | 6.01 | 6.39 | 7.1325 |
| 51.3 | 5.79 | 6.0125 | 6.3925 | 7.1375 |
| 51.4 | 5.79 | 6.015 | 6.395 | 7.1425 |
| 51.5 | 5.7925 | 6.0175 | 6.3975 | 7.1475 |
| 51.6 | 5.7925 | 6.0175 | 6.4025 | 7.1525 |
| 51.7 | 5.795 | 6.02 | 6.405 | 7.1575 |
| 51.8 | 5.7975 | 6.0225 | 6.4075 | 7.1625 |
| 51.9 | 5.7975 | 6.025 | 6.41 | 7.165 |
| 52.0 | 5.8 | 6.0275 | 6.4125 | 7.17 |
| 52.1 | 5.8 | 6.03 | 6.415 | 7.175 |
| 52.2 | 5.8025 | 6.03 | 6.42 | 7.18 |
| 52.3 | 5.305 | 6.0325 | 6.4225 | 7.185 |
| 52.4 | 5.305 | 6.035 | 6.425 | 7.19 |
| 52.5 | 5.8075 | 6.0375 | 6.4275 | 7.195 |
| 52.6 | 5.8075 | 6.0375 | 6.43 | 7.2 |
| 52.7 | 5.81 | 6.04 | 6.4325 | 7.2025 |
| 52.8 | 5.81 | 6.0425 | 6.435 | 7.2075 |
| 52.9 | 5.8125 | 6.045 | 6.44 | 7.2125 |
| 53.0 | 5.8125 | 6.045 | 6.4425 | 7.2175 |
| 53.1 | 5.815 | 6.0475 | 6.445 | 7.2225 |
| 53.2 | 5.815 | 6.05 | 6.4475 | 7.2275 |
| 53.3 | 5.8175 | 6.0525 | 6.45 | 7.23 |
| 53.4 | 5.82 | 6.0525 | 6.4525 | 7.235 |
| 53.5 | 5.62 | 6.055 | 6.455 | 7.24 |
| 53.6 | 5.8225 | 6.0575 | 6.4575 | 7.245 |
| 53.7 | 5.8225 | 6.0575 | 6.46 | 7.25 |
| 53.8 | 5.825 | 6.06 | 6.4625 | 7.255 |
| 53.9 | 5.825 | 6.0625 | 6.465 | 7.2575 |
| 54.0 | 5.825 | 6.065 | 6.4675 | 7.2625 |
| 54.1 | 5.8275 | 6.065 | 6.4725 | 7.2675 |
| 54.2 | 5.8275 | 6.0675 | 6.475 | 7.2725 |
| 54.3 | 5.83 | 6.07 | 6.4775 | 7.275 |
| 54.4 | 5.63 | 6.07 | 6.48 | 7.23 |
| 54.5 | 5.8325 | 6.0725 | 6.4825 | 7.235 |
| 54.6 | 5.8325 | 6.075 | 6.485 | 7.29 |
| 54.7 | 5.835 | 6.075 | 6.4875 | 7.2925 |
| 54.8 | 5.835 | 6.0775 | 6.49 | 7.2975 |
| 54.9 | 5.8375 | 6.08 | 6.4925 | 7.3025 |
| 55.0 | 5.8375 | 6.08 | 6.495 | 7.3075 |
| 55.1 | 5.8375 | 6.0825 | 6.4975 | 7.31 |
| 55.2 | 5.84 | 6.0325 | 6.5 | 7.315 |
| 55.3 | 5.84 | 6.085 | 6.5025 | 7.32 |
| 55.4 | 5.8425 | 6.0375 | 6.505 | 7.3225 |
| 55.5 | 5.8425 | 6.0875 | 6.5075 | 7.3275 |
| 55.6 | 5.8425 | 6.09 | 6.51 | 7.3325 |
| 55.7 | 5.845 | 6.09 | 6.5125 | 7.3375 |
| 55.8 | 5.845 | 6.0925 | 6.515 | 7.34 |
| 55.9 | 5.8475 | 6.095 | 6.5175 | 7.345 |
| 56.0 | 5.8475 | 6.095 | 6.5175 | 7.35 |
| 56.1 | 5.8475 | 6.0975 | 6.52 | 7.3525 |
| 56.2 | 5.85 | 6.0975 | 6.5225 | 7.3575 |
| 56.3 | 5.85 | 6.1 | 6.525 | 7.3625 |
| 56.4 | 5.85 | 6.1025 | 6.5275 | 7.3135 |
| 56.5 | 5.8525 | 6.1025 | 6.53 | 7.37 |
| 56.6 | 5.8525 | 6.105 | 6.5325 | 7.375 |
| 56.7 | 5.8525 | 6.105 | 6.535 | 7.3775 |
| 56.8 | 5.855 | 6.1075 | 6.5375 | 7.3825 |
| 56.9 | 5.355 | 6.1075 | 6.54 | 7.3875 |
| 57.0 | 5.855 | 6.11 | 6.5425 | 7.39 |
| 57.1 | 5.8575 | 6.11 | 6.545 | 7.395 |
| 57.2 | 5.8575 | 6.1125 | 6.5475 | 7.3975 |
| 57.3 | 5.8575 | 6.115 | 6.5475 | 7.4025 |
| 57.4 | 5.86 | 6.115 | 6.55 | 7.4075 |
| 57.5 | 5.86 | 6.1175 | 6.5525 | 7.41 |
| 57.6 | 5.86 | 6.1175 | 6.555 | 7.415 |
| 57.7 | 5.8625 | 6.12 | 6.5575 | 7.42 |
| 57.8 | 5.8625 | 6.12 | 6.56 | 7.4225 |
| 57.9 | 5.8625 | 6.1225 | 6.5625 | 7.4275 |
| 58.0 | 5.865 | 6.1225 | 6.565 | 7.43 |
| 58.1 | 5.865 | 6.125 | 6.565 | 7.135 |
| 58.2 | 5.865 | 6.125 | 6.5675 | 7.44 |
| 58.3 | 5.865 | 6.1275 | 6.57 | 7.4425 |
| 58.4 | 5.8675 | 6.1275 | 6.5725 | 7.4475 |
| 58.5 | 5.8675 | 6.13 | 6.575 | 7.45 |
| 58.6 | 5.8675 | 6.13 | 6.5775 | 7.455 |
| 58.7 | 5.87 | 6.1325 | 6.5775 | 7.4575 |
| 58.8 | 5.37 | 6.1325 | 6.53 | 7.4625 |
| 58.9 | 5.137 | 6.135 | 6.5825 | 7.4675 |
| 59.0 | 5.87 | 6.135 | 6.585 | 7.47 |
| 59.1 | 5.8725 | 6.135 | 6.5875 | 7.175 |
| 59.2 | 5.8725 | 6.1375 | 6.59 | 7.4775 |
| 59.3 | 5.8725 | 6.1375 | 6.59 | 7.4825 |
| 59.4 | 5.3725 | 6.14 | 6.5925 | 7.435 |
| 59.5 | 5.875 | 6.14 | 6.595 | 7.49 |
| 59.6 | 5.875 | 6.1425 | 6.5975 | 7.4925 |
| 59.7 | 5.875 | 6.1425 | 6.6 | 7.4975 |

APPENDIX 2-continued

Reverse Pressure lookup

| | Temp | | | |
|---|---|---|---|---|
| | 17.2 C. | 20.1 C. | 25.1 C. | 35.1 C. |
| 59.8 | 5.875 | 6.145 | 6.6 | 7.5 |
| 59.9 | 5.8775 | 6.145 | 6.6025 | 7.505 |
| 60.0 | 5.8775 | 6.145 | 6.605 | 7.5075 |
| 50.1 | 5.8775 | 6.1475 | 6.6075 | 7.5125 |
| 60.2 | 5.8775 | 6.1475 | 8.61 | 7.515 |
| 60.3 | 5.8775 | 6.15 | 8.61 | 7.52 |
| 60.4 | 5.88 | 6.15 | 6.6125 | 7.525 |
| 60.5 | 5.88 | 6.1525 | 6.615 | 7.5275 |
| 60.6 | 5.88 | 6.1525 | 6.6175 | 7.5325 |
| 60.7 | 5.88 | 6.1525 | 6.6175 | 7.535 |
| 60.8 | 5.8825 | 6.155 | 6.62 | 7.54 |
| 60.9 | 5.8825 | 6.155 | 6.6225 | 7.5425 |
| 61.0 | 5.8825 | 6.1575 | 6.625 | 7.545 |
| 61.1 | 5.8825 | 5.1575 | 6.6275 | 7.55 |
| 61.2 | 5.8825 | 5.1575 | 6.6275 | 7.5525 |
| 61.3 | 5.385 | 6.16 | 8.63 | 7.5575 |
| 61.4 | 5.385 | 6.16 | 6.6325 | 7.56 |
| 61.5 | 5.885 | 6.1625 | 6.635 | 7.565 |
| 61.6 | 5.885 | 6.1625 | 6.635 | 7.5675 |
| 61.7 | 5.885 | 6.1625 | 6.6375 | 7.5725 |
| 61.8 | 5.885 | 6.165 | 6.64 | 7.575 |
| 61.9 | 5.8875 | 6.165 | 6.64 | 7.58 |
| 62.0 | 5.8875 | 6.165 | 6.6425 | 7.5325 |
| 52.1 | 5.8875 | 5.1675 | 6.645 | 7.5875 |
| 52.2 | 5.8875 | 5.1675 | 6.6475 | 7.59 |
| 52.3 | 5.8875 | 6.17 | 6.6475 | 7.595 |
| 62.4 | 5.8375 | 6.17 | 6.65 | 7.5975 |
| 62.5 | 5.89 | 6.17 | 6.6525 | 7.6 |
| 62.6 | 5.89 | 6.1725 | 6.6525 | 7.605 |
| 62.7 | 5.89 | 6.1725 | 6.655 | 7.6075 |
| 62.8 | 5.89 | 6.1725 | 8.6575 | 7.6125 |
| 62.9 | 5.89 | 6.175 | 6.66 | 7.615 |
| 63.0 | 5.89 | 6.175 | 6.66 | 7.62 |
| 63.1 | 5.8925 | 6.175 | 6.6625 | 7.6225 |
| 63.2 | 5.8925 | 5.1775 | 6.665 | 7.5275 |
| 63.3 | 5.8925 | 6.1775 | 6.665 | 7.63 |
| 63.4 | 5.8925 | 6.1775 | 6.6675 | 7.6325 |
| 63.5 | 5.8925 | 6.18 | 6.67 | 7.6375 |
| 63.6 | 5.8925 | 6.18 | 6.67 | 7.64 |
| 63.7 | 5.8925 | 6.18 | 6.6725 | 7.645 |
| 63.8 | 5.895 | 6.1825 | 6.575 | 7.6475 |
| 63.9 | 5.895 | 6.1825 | 6.6775 | 7.65 |
| 64.0 | 5.895 | 6.1825 | 6.6775 | 7.655 |
| 64.1 | 5.895 | 6.185 | 6.68 | 7.6575 |
| 54.2 | 5.895 | 6.185 | 6.6825 | 7.5625 |
| 54.3 | 5.895 | 6.185 | 6.6825 | 7.665 |
| 64.4 | 5.395 | 6.1875 | 6.685 | 7.67 |
| 64.5 | 5.895 | 6.1875 | 6.6875 | 7.6725 |
| 64.6 | 5.8975 | 6.1875 | 6.6875 | 7.675 |
| 64.7 | 5.8975 | 6.19 | 6.69 | 7.68 |
| 64.8 | 5.8975 | 6.19 | 6.6925 | 7.6825 |
| 64.9 | 5.8975 | 6.19 | 6.6925 | 7.6875 |
| 65.0 | 5.8975 | 6.1925 | 6.695 | 7.69 |
| 65.1 | 5.8975 | 6.1925 | 6.6975 | 7.6925 |
| 65.2 | 5.8975 | 6.1925 | 6.6975 | 7.6975 |
| 65.3 | 5.8975 | 6.195 | 6.7 | 7.7 |
| 65.4 | 5.3975 | 6.195 | 6.7 | 7.7025 |
| 65.5 | 5.9 | 6.195 | 6.7025 | 7.7075 |
| 65.6 | 5.9 | 6.195 | 6.705 | 7.71 |
| 65.7 | 5.9 | 6.1975 | 6.705 | 7.715 |
| 65.8 | 5.9 | 6.1975 | 6.7075 | 7.7175 |
| 65.9 | 5.9 | 6.1975 | 6.71 | 7.72 |
| 66.0 | 5.9 | 6.2 | 6.71 | 7.725 |
| 66.1 | 5.9 | 6.2 | 6.7125 | 7.7275 |
| 66.2 | 5.9 | 6.2 | 6.715 | 7.73 |
| 66.3 | 5.9 | 6.2 | 8.715 | 7.735 |
| 66.4 | 5.9 | 6.2025 | 6.7175 | 7.7375 |
| 66.5 | 5.9025 | 6.2025 | 6.72 | 7.7425 |
| 66.6 | 5.9025 | 6.2025 | 6.72 | 7.745 |
| 66.7 | 5.9025 | 6.205 | 6.7225 | 7.7475 |
| 65.8 | 5.9025 | 6.205 | 6.7225 | 7.7525 |
| 66.9 | 5.9025 | 6.205 | 6.725 | 7.755 |
| 67.0 | 5.9025 | 6.205 | 6.7275 | 7.7575 |
| 67.1 | 5.9025 | 6.2075 | 6.7275 | 7.7625 |
| 67.2 | 5.9025 | 6.2075 | 6.73 | 7.765 |
| 67.3 | 5.9025 | 6.2075 | 5.7325 | 7.77 |
| 67.4 | 5.9025 | 6.21 | 6.7325 | 7.7725 |
| 67.5 | 5.9025 | 6.21 | 6.735 | 7.775 |
| 67.6 | 5.9025 | 6.21 | 6.735 | 7.78 |
| 67.7 | 5.905 | 6.21 | 6.7375 | 7.7525 |
| 67.8 | 5.905 | 6.2125 | 6.74 | 7.785 |
| 37.9 | 5.905 | 6.2125 | 6.74 | 7.79 |
| 68.0 | 5.905 | 6.2125 | 6.7425 | 7.7925 |
| 68.1 | 5.905 | 6.2125 | 6.7425 | 7.795 |
| 68.2 | 5.905 | 6.215 | 6.745 | 7.5 |
| 68.3 | 5.905 | 6.215 | 6.7475 | 7.8025 |
| 68.4 | 5.905 | 6.215 | 6.7475 | 7.805 |
| 68.5 | 5.905 | 6.215 | 6.75 | 7.81 |
| 68.6 | 5.905 | 6.2175 | 6.75 | 7.8125 |
| 65.7 | 5.905 | 6.2175 | 6.7525 | 7.815 |
| 68.8 | 5.905 | 6.2175 | 6.755 | 7.82 |
| 68.9 | 5.905 | 6.22 | 6.755 | 7.3225 |
| 69.0 | 5.905 | 6.22 | 6.7575 | 7.825 |
| 69.1 | 5.9075 | 6.22 | 6.7575 | 7.83 |
| 69.2 | 5.9075 | 6.22 | 6.76 | 7.8325 |
| 69.3 | 5.9075 | 6.2225 | 5.7625 | 7.8375 |
| 69.4 | 5.9075 | 6.2225 | 6.7625 | 7.84 |
| 69.5 | 5.9075 | 6.2225 | 6.765 | 7.8425 |
| 69.6 | 5.9075 | 6.2225 | 6.765 | 7.8475 |
| 69.7 | 5.9075 | 6.225 | 6.7675 | 7.85 |
| 69.8 | 5.9075 | 6.225 | 6.77 | 7.8525 |
| 69.9 | 5.9075 | 6.225 | 6.77 | 7.8575 |
| 70.0 | 5.9075 | 6.225 | 6.7725 | 7.86 |
| 70.1 | 5.9075 | 6.2275 | 6.7725 | 7.8625 |
| 70.2 | 5.9075 | 6.2275 | 6.775 | 7.8675 |
| 70.3 | 5.9075 | 6.2275 | 6.7775 | 7.87 |
| 70.4 | 5.9975 | 6.2275 | 6.7775 | 7.8725 |
| 70.5 | 5.9075 | 6.2275 | 6.78 | 7.8775 |
| 70.6 | 5.9075 | 6.23 | 6.78 | 7.88 |
| 70.7 | 5.9075 | 6.23 | 6.7825 | 7.8825 |
| 70.8 | 5.9075 | 6.23 | 6.785 | 7.8375 |
| 70.9 | 5.91 | 6.23 | 6.785 | 7.89 |
| 71.0 | 5.91 | 6.2325 | 6.7875 | 7.8925 |
| 71.1 | 5.91 | 5.2325 | 6.7875 | 7.8975 |
| 71.2 | 5.91 | 6.2325 | 6.79 | 7.9 |
| 71.3 | 5.91 | 6.2325 | 6.79 | 7.9025 |
| 71.4 | 5.91 | 6.235 | 6.7925 | 7.9075 |
| 71.5 | 5.91 | 6.235 | 6.795 | 7.91 |
| 71.6 | 5.91 | 6.235 | 6.795 | 7.9125 |
| 71.7 | 5.91 | 6.235 | 6.7975 | 7.9175 |
| 71.8 | 5.91 | 6.2375 | 6.7975 | 7.92 |
| 71.9 | 5.91 | 6.2375 | 6.8 | 7.9225 |
| 72.0 | 5.91 | 6.2375 | 6.8025 | 7.9275 |
| 72.1 | 5.91 | 6.2375 | 6.8025 | 7.93 |
| 72.2 | 5.91 | 6.24 | 6.805 | 7.9325 |
| 72.3 | 5.91 | 6.24 | 6.805 | 7.9375 |
| 72.4 | 5.91 | 6.24 | 6.8075 | 7.941 |
| 72.5 | 5.91 | 6.24 | 6.8075 | 7.9425 |
| 72.6 | 5.91 | 5.24 | 6.81 | 7.9475 |
| 72.7 | 5.91 | 6.2425 | 6.8125 | 7.95 |
| 72.8 | 5.91 | 6.2425 | 8.3125 | 7.9525 |
| 72.9 | 5.91 | 6.2425 | 6.815 | 7.9575 |
| 73.0 | 5.9125 | 6.2425 | 6.815 | 7.96 |
| 73.1 | 5.9125 | 6.245 | 6.8175 | 7.9625 |
| 73.2 | 5.9125 | 6.245 | 6.82 | 7.9675 |
| 73.3 | 5.9125 | 6.245 | 6.32 | 7.97 |
| 73.4 | 5.9125 | 6.245 | 6.8225 | 7.9725 |
| 73.5 | 5.9125 | 6.2475 | 6.8225 | 7.9775 |
| 73.6 | 5.9125 | 6.2475 | 6.825 | 7.98 |
| 73.7 | 5.9125 | 6.2475 | 6.825 | 7.9825 |
| 73.8 | 5.9125 | 6.2475 | 6.3275 | 7.9375 |
| 73.9 | 5.9125 | 6.2475 | 6.83 | 7.99 |
| 74.0 | 5.9125 | 6.25 | 6.83 | 7.995 |
| 74.1 | 5.9125 | 6.25 | 6.8325 | 7.9975 |
| 74.2 | 5.9125 | 6.25 | 6.8325 | 8 |
| 74.3 | 5.9125 | 6.25 | 6.835 | 8.005 |
| 74.4 | 5.9125 | 6.2525 | 6.835 | 8.0075 |
| 74.5 | 5.9125 | 6.2525 | 6.8375 | 8.01 |

APPENDIX 2-continued

Reverse Pressure lookup

| | Temp | | | |
|---|---|---|---|---|
| | 17.2 C. | 20.1 C. | 25.1 C. | 35.1 C. |
| 74.6 | 5.9125 | 6.2525 | 6.84 | 8.015 |
| 74.7 | 5.9125 | 6.2525 | 6.84 | 8.0175 |
| 74.8 | 5.9125 | 6.255 | 6.8425 | 8.02 |
| 74.9 | 5.9125 | 6.255 | 6.8425 | 8.025 |
| 75.0 | 5.9125 | 6.255 | 6.845 | 8.0275 |
| 75.1 | 5.9125 | 6.255 | 6.8475 | 8.03 |
| 75.2 | 5.9125 | 6.255 | 6.8475 | 8.035 |
| 75.3 | 5.9125 | 6.2575 | 6.85 | 8.0375 |
| 75.4 | 5.9125 | 6.2575 | 6.85 | 8.04 |
| 75.5 | 5.915 | 6.2575 | 6.8525 | 8.045 |
| 75.6 | 5.915 | 6.2575 | 6.8525 | 8.0475 |
| 75.7 | 5.915 | 6.26 | 6.855 | 8.0525 |
| 75.8 | 5.915 | 6.26 | 6.8575 | 8.055 |
| 75.9 | 5.915 | 6.26 | 6.8575 | 8.0575 |
| 76.0 | 5.915 | 6.26 | 6.86 | 8.0625 |
| 76.1 | 5.915 | 6.2625 | 6.86 | 8.065 |
| 76.2 | 5.915 | 6.2625 | 6.8625 | 8.0675 |
| 76.3 | 5.915 | 6.2625 | 6.365 | 3.0725 |
| 76.4 | 5.915 | 6.2625 | 6.865 | 8.075 |
| 76.5 | 5.915 | 6.2625 | 6.8675 | 8.08 |
| 76.6 | 5.915 | 6.265 | 6.8675 | 8.0825 |
| 75.7 | 5.915 | 5.265 | 6.87 | 8.085 |
| 76.8 | 5.915 | 6.265 | 6.8725 | 8.09 |
| 76.9 | 5.915 | 6.265 | 6.8725 | 8.0925 |
| 77.0 | 5.915 | 6.2575 | 6.875t | 8.095 |
| 77.1 | 5.915 | 6.2675 | 6.8751 | 8.1 |
| 77.2 | 5.915 | 6.2675 | 6.8775 | 8.1025 |
| 77.3 | 5.915 | 6.2675 | 6.8775 | 8.1075 |
| 77.4 | 5.915 | 6.27 | 6.88 | 8.11 |
| 77.5 | 5.915 | 6.27 | 6.8825 | 8.1125 |
| 77.6 | 5.915 | 6.27 | 6.8825 | 8.1175 |
| 77.7 | 5.915 | 6.27 | 6.885 | 8.12 |
| 77.8 | 5.915 | 6.27 | 6.885 | 8.125 |
| 77.9 | 5.915 | 6.2725 | 6.8875 | 8.1275 |
| 78.0 | 5.9175 | 6.2725 | 6.89 | 8.13 |
| 76.1 | 5.9175 | 6.2725 | 6.89 | 8.135 |
| 78.2 | 5.9175 | 6.2725 | 6.8925 | 8.1375 |
| 78.3 | 5.9175 | 6.275 | 6.8925 | 8.1425 |
| 78.4 | 5.9175 | 6.275 | 6.895 | 8.145 |
| 78.5 | 5.9175 | 6.275 | 6.8975 | 8.1475 |
| 78.6 | 5.9175 | 6.275 | 6.8975 | 8.1525 |
| 78.7 | 5.9175 | 6.2775 | 6.9 | 8.155 |
| 78.8 | 5.9175 | 6.2775 | 6.9025 | 8.16 |
| 78.9 | 5.9175 | 6.2775 | 6.9025 | 8.1625 |
| 79.0 | 5.9175 | 6.2775 | 6.905 | 8.1675 |
| 79.1 | 5.9175 | 6.28 | 6.905 | 8.17 |
| 79.2 | 5.9175 | 6.28 | 6.9075 | 8.1725 |
| 79.3 | 5.9175 | 6.28 | 6.91 | 8.1775 |
| 79.4 | 5.9175 | 6.28 | 6.91 | 8.18 |
| 79.5 | 5.9175 | 6.2825 | 6.9125 | 8.185 |
| 79.6 | 5.9175 | 6.2825 | 6.9125 | 8.1875 |
| 79.7 | 5.9175 | 6.2825 | 6.915 | 8.1925 |
| 79.8 | 5.9175 | 6.2825 | 6.9175 | 8.195 |
| 79.9 | 5.9175 | 6.285 | 6.9175 | 8.2 |
| 80.0 | 5.9175 | 6.285 | 6.92 | 8.2025 |
| 80.1 | 5.9175 | 6.285 | 6.9225 | 8.205 |
| 80.2 | 5.9175 | 6.285 | 6.9225 | 8.21 |
| 80.3 | 5.92 | 6.2875 | 6.925 | 8.2125 |
| 80.4 | 5.92 | 6.2875 | 6.925 | 8.2175 |
| 60.5 | 5.92 | 6.2875 | 6.9275 | 8.22 |
| 80.6 | 5.92 | 6.2875 | 6.93 | 8.225 |
| 80.7 | 5.92 | 6.29 | 6.93 | 8.2275 |
| 80.8 | 5.92 | 6.29 | 6.9325 | 8.2325 |
| 80.9 | 5.92 | 6.29 | 6.935 | 8.235 |
| 81.0 | 5.92 | 6.29 | 6.935 | 8.24 |
| 81.1 | 5.92 | 6.2925 | 6.9375 | 8.2425 |
| 81.2 | 5.92 | 6.2925 | 6.94 | 8.2475 |
| 81.3 | 5.92 | 6.2925 | 6.94 | 8.25 |
| 81.4 | 5.92 | 6.2925 | 6.9425 | 8.255 |
| 81.5 | 5.92 | 6.295 | 6.9425 | 8.2575 |
| 81.6 | 5.92 | 6.295 | 6.945 | 8.2625 |
| 81.7 | 5.92 | 6.295 | 6.9475 | 8.265 |
| 81.8 | 5.92 | 6.295 | 6.9475 | 8.27 |
| 81.9 | 5.92 | 6.2975 | 6.95 | 8.2725 |
| 82.0 | 5.92 | 6.2975 | 6.9525 | 8.2775 |
| 82.1 | 5.92 | 6.2975 | 6.9525 | 8.28 |
| 82.2 | 5.9225 | 6.2975 | 6.955 | 8.285 |
| 82.3 | 5.9225 | 6.3 | 6.9575 | 8.2875 |
| 82.4 | 5.9225 | 3.3 | 6.9575 | 8.2925 |
| 82.5 | 5.9225 | 6.3 | 6.96 | 8.295 |
| 82.6 | 5.9225 | 6.3025 | 6.9625 | 8.3 |
| 82.7 | 5.9225 | 6.3025 | 6.9625 | 8.3025 |
| 82.8 | 5.9225 | 6.3025 | 6.965 | 8.3075 |
| 82.9 | 5.9225 | 6.3025 | 6.9675 | 8.3125 |
| 83.0 | 5.9225 | 6.305 | 6.9675 | 8.315 |
| 83.1 | 5.9225 | 6.305 | 6.97 | 8.32 |
| 83.2 | 5.9225 | 6.305 | 6.9725 | 8.3225 |
| 83.3 | 5.9225 | 6.305 | 6.9725 | 8.3275 |
| 83.4 | 5.9225 | 6.3075 | 6.975 | 8.33 |
| 83.5 | 5.9225 | 6.3075 | 6.9775 | 8.335 |
| 83.6 | 5.9225 | 6.3075 | 6.98 | 8.34 |
| 83.7 | 5.9225 | 6.31 | 6.98 | 8.3425 |
| 83.8 | 5.925 | 6.31 | 6.9825 | 8.3475 |
| 83.9 | 5.925 | 6.31 | 6.985 | 8.35 |
| 84.0 | 5.925 | 6.31 | 6.985 | 8.355 |
| 84.1 | 5.925 | 6.3125 | 6.9875 | 8.3575 |
| 84.2 | 5.925 | 6.3125 | 6.99 | 8.3625 |
| 84.3 | 5.925 | 6.3125 | 6.99 | 8.3675 |
| 84.4 | 5.925 | 6.315 | 6.9925 | 8.37 |
| 84.5 | 5.925 | 6.315 | 6.995 | 8.375 |
| 84.6 | 5.925 | 6.315 | 6.9975 | 8.38 |
| 34.7 | 5.925 | 6.3175 | 6.9975 | 8.3825 |
| 34.8 | 5.925 | 6.3175 | 7 | 8.3875 |
| 84.9 | 5.925 | 6.3175 | 7.0025 | 8.39 |
| 85.0 | 5.925 | 6.32 | 7.0025 | 8.395 |
| 85.1 | 5.9275 | 6.32 | 7.005 | 8.4 |
| 85.2 | 5.9275 | 6.32 | 7.0075 | 8.4025 |
| 85.3 | 5.9275 | 6.32 | 7.01 | 8.4075 |
| 85.4 | 5.9275 | 6.3225 | 7.01 | 8.4125 |
| 85.5 | 5.9275 | 6.3225 | 7.0125 | 8.415 |
| 85.6 | 5.9275 | 6.3225 | 7.015 | 8.42 |
| 85.7 | 5.9275 | 6.325 | 7.0175 | 8.425 |
| 35.8 | 5.9275 | 5.325 | 7.0175 | 8.4275 |
| 85.9 | 5.9275 | 6.325 | 7.02 | 8.4325 |
| 86.0 | 5.9275 | 6.3275 | 7.0225 | 8.4375 |
| 86.1 | 5.9275 | 6.3275 | 7.025 | 8.44 |
| 86.2 | 5.93 | 6.3275 | 7.025 | 8.445 |
| 86.3 | 5.93 | 6.33 | 7.0275 | 8.45 |
| 86.4 | 5.93 | 6.33 | 7.03 | 8.455 |
| 86.5 | 5.93 | 6.33 | 7.0325 | 8.4575 |
| 86.6 | 5.93 | 6.3325 | 7.0325 | 8.4625 |
| 86.7 | 5.93 | 6.3325 | 7.035 | 8.4675 |
| 36.8 | 5.93 | 6.3325 | 7.0375 | 8.4725 |
| 86.9 | 5.93 | 6.335 | 7.04 | 8.475 |
| 87.0 | 5.93 | 6.335 | 7.0425 | 8.48 |
| 87.1 | 5.9325 | 6.335 | 7.0425 | 8.485 |
| 87.2 | 5.9325 | 6.3375 | 7.045 | 8.49 |
| 87.3 | 5.9325 | 6.3375 | 7.0475 | 8.4925 |
| 87.4 | 5.9325 | 6.34 | 7.05 | 8.4975 |
| 87.5 | 5.9325 | 6.34 | 7.0525 | 8.5025 |
| 87.6 | 5.9325 | 6.34 | 7.0525 | 8.5075 |
| 87.7 | 5.9325 | 6.3425 | 7.055 | 8.51 |
| 37.8 | 5.9325 | 6.3425 | 7.0575 | 8.515 |
| 87.9 | 5.9325 | 6.3425 | 7.06 | 8.52 |
| 88.0 | 5.935 | 6.345 | 7.0625 | 8.525 |
| 88.1 | 5.935 | 6.345 | 7.065 | 8.53 |
| 88.2 | 5.935 | 6.345 | 7.065 | 8.5325 |
| 88.3 | 5.935 | 6.3475 | 7.0675 | 8.5375 |
| 88.4 | 5.935 | 6.3475 | 7.07 | 8.5425 |
| 88.5 | 5.935 | 6.35 | 7.0725 | 8.5475 |
| 88.6 | 5.935 | 6.35 | 7.075 | 8.5525 |
| 88.7 | 5.9375 | 6.35 | 7.0775 | 8.5575 |
| 38.8 | 5.9375 | 6.3525 | 7.03 | 8.5625 |
| 88.9 | 5.9375 | 6.3525 | 7.08 | 8.565 |
| 89.0 | 5.9375 | 6.355 | 7.0825 | 8.57 |
| 89.1 | 5.9375 | 6.355 | 7.085 | 8.575 |
| 89.2 | 5.9375 | 6.355 | 7.0875 | 8.58 |
| 89.3 | 5.9375 | 6.3575 | 7.09 | 8.535 |

APPENDIX 2-continued

Reverse Pressure lookup

| | Temp | | | |
|---|---|---|---|---|
| | 17.2 C. | 20.1 C. | 25.1 C. | 35.1 C. |
| 89.4 | 5.94 | 6.3575 | 7.0925 | 8.59 |
| 89.5 | 5.94 | 6.36 | 7.095 | 8.595 |
| 89.6 | 5.94 | 6.36 | 7.0975 | 8.6 |
| 89.7 | 5.94 | 6.3625 | 7.1 | 8.605 |
| 89.8 | 5.94 | 6.3625 | 7.1 | 8.61 |
| 89.9 | 5.94 | 6.3625 | 7.1025 | 8.615 |
| 90.0 | 5.9425 | 6.365 | 7.105 | 8.6175 |
| 90.1 | 5.9425 | 6.365 | 7.1075 | 8.625 |
| 90.2 | 5.9425 | 6.3675 | 7.11 | 8.6275 |
| 90.3 | 5.9425 | 6.3675 | 7.1125 | 8.6325 |
| 90.4 | 5.9425 | 6.37 | 7.115 | 8.6375 |
| 90.5 | 5.9425 | 6.37 | 7.1175 | 8.6425 |
| 90.6 | 5.945 | 6.37 | 7.12 | 8.6475 |
| 90.7 | 5.945 | 6.3725 | 7.1225 | 8.6525 |
| 90.8 | 5.945 | 6.3725 | 7.125 | 8.6575 |
| 90.9 | 5.945 | 6.375 | 7.1275 | 8.6625 |
| 91.0 | 5.945 | 6.375 | 7.13 | 8.6675 |
| 91.1 | 5.9475 | 6.3775 | 7.1325 | 8.675 |
| 91.2 | 5.9475 | 6.3775 | 7.135 | 8.68 |
| 91.3 | 5.9475 | 6.38 | 7.1375 | 8.685 |
| 91.4 | 5.9475 | 6.38 | 7.14 | 8.69 |
| 91.5 | 5.9475 | 6.3825 | 7.1425 | 8.695 |
| 91.6 | 5.95 | 6.3825 | 7.145 | 8.7 |
| 91.7 | 5.95 | 6.385 | 7.1475 | 8.705 |
| 91.8 | 5.95 | 6.385 | 7.15 | 8.71 |
| 91.9 | 5.95 | 6.3875 | 7.1525 | 8.715 |
| 92.0 | 5.9525 | 6.3875 | 7.155 | 8.72 |
| 92.1 | 5.9525 | 6.39 | 7.1575 | 8.725 |
| 92.2 | 5.9525 | 6.39 | 7.16 | 8.7325 |
| 92.3 | 5.9525 | 6.3925 | 7.1625 | 8.7375 |
| 92.4 | 5.9525 | 6.3925 | 7.1135 | 3.7425 |
| 92.5 | 5.955 | 6.395 | 7.1675 | 8.7475 |
| 92.6 | 5.955 | 6.3975 | 7.17 | 8.7525 |
| 92.7 | 5.955 | 6.3975 | 7.1725 | 8.7575 |
| 92.8 | 5.955 | 6.4 | 7.175 | 8.7625 |
| 92.9 | 5.9575 | 6.4 | 7.11/5 | 8.77 |
| 93.0 | 5.9575 | 6.4025 | 7.18 | 8.775 |
| 93.1 | 5.9575 | 6.4025 | 7.1825 | 8.78 |
| 93.2 | 5.96 | 6.405 | 7.1875 | 8.785 |
| 93.3 | 5.96 | 6.405 | 7.19 | 8.7925 |
| 93.4 | 5.96 | 6.4075 | 7.1925 | 8.7975 |
| 93.5 | 5.96 | 6.41 | 7.195 | 8.8025 |
| 93.6 | 5.9625 | 6.41 | 7.1975 | 8.8075 |
| 93.7 | 5.9625 | 6.4125 | 7.2 | 8.815 |
| 93.8 | 5.9625 | 6.4125 | 7.2025 | 8.82 |
| 93.9 | 5.965 | 6.415 | 7.2075 | 8.825 |
| 94.0 | 5.965 | 6.4175 | 7.21 | 8.8325 |
| 94.1 | 5.965 | 6.4175 | 7.2125 | 8.8375 |
| 94.2 | 5.9675 | 6.42 | 7.215 | 8.8425 |
| 94.3 | 5.9675 | 6.4225 | 7.2175 | 8.85 |
| 94.4 | 5.9675 | 6.4225 | 7.22 | 8.855 |
| 94.5 | 5.9675 | 6.425 | 7.225 | 8.86 |
| 94.6 | 5.97 | 6.425 | 7.2275 | 8.8675 |
| 94.7 | 5.97 | 6.4275 | 7.23 | 8.8725 |
| 94.8 | 5.9725 | 6.43 | 7.2325 | 8.8775 |
| 94.9 | 5.9725 | 6.43 | 7.2375 | 8.885 |
| 95.0 | 5.9725 | 6.4325 | 7.24 | 8.89 |
| 95.1 | 5.975 | 6.435 | 7.2425 | 8.8975 |
| 95.2 | 5.975 | 6.435 | 7.245 | 8.9025 |
| 95.3 | 5.975 | 6.4375 | 7.2475 | 8.9075 |
| 95.4 | 5.9775 | 6.44 | 7.2525 | 8.915 |
| 95.5 | 5.9775 | 6.4425 | 7.255 | 8.92 |
| 95.6 | 5.9775 | 6.4425 | 7.2575 | 8.9275 |
| 95.7 | 5.98 | 6.445 | 7.2625 | 8.9325 |
| 95.8 | 5.98 | 6.4475 | 7.265 | 8.94 |
| 95.9 | 5.9325 | 6.4475 | 7.2675 | 8.945 |
| 96.0 | 5.9825 | 6.45 | 7.2725 | 8.9525 |
| 96.1 | 5.9825 | 6.4525 | 7.275 | 8.96 |
| 96.2 | 5.985 | 6.455 | 7.2775 | 8.965 |
| 96.3 | 5.985 | 6.455 | 7.2325 | 8.9725 |
| 96.4 | 5.9875 | 6.4575 | 7.285 | 8.9775 |
| 96.5 | 5.9875 | 6.46 | 7.2375 | 8.9135 |
| 96.6 | 5.99 | 6.4625 | 7.2925 | 8.99 |
| 96.7 | 5.99 | 6.465 | 7.295 | 8.9975 |
| 96.8 | 5.9925 | 6.465 | 7.3 | 9 |

APPENDIX 3

Lookup mass as function of dP (inside)

| | | Delta T | | | |
|---|---|---|---|---|---|
| | | 5 C. Delta | 10 C. Delta | 15 C. Delta | 18 C. Delta |
| mass | 30.0 | 0.1925 | 0.3775 | 0.57 | |
| | 30.1 | 0.1925 | 0.3825 | 0.575 | |
| | 30.2 | 0.1925 | 0.3825 | 0.575 | |
| | 30.3 | 0.195 | 0.3825 | 0.5775 | |
| | 30.4 | 0.195 | 0.3850 | 0.58 | |
| | 30.5 | 0.1975 | 0.3850 | 0.5825 | |
| | 30.6 | 0.195 | 0.3900 | 0.585 | |
| | 30.7 | 0.1975 | 0.3900 | 0.5875 | |
| | 30.8 | 0.1975 | 0.3925 | 0.59 | |
| | 30.9 | 0.2 | 0.3925 | 0.5925 | |
| | 31.0 | 0.2 | 0.3950 | 0.595 | |
| | 31.1 | 0.2025 | 0.3950 | 0.5975 | |
| | 31.2 | 0.2025 | 0.3975 | 0.6 | |
| | 31.3 | 0.2025 | 0.3975 | 0.6 | |
| | 31.4 | 0.2025 | 0.4000 | 0.6025 | |
| | 31.5 | 0.2025 | 0.4025 | 0.605 | 0.725 |
| | 31.6 | 0.205 | 0.4050 | 0.61 | 0.73 |
| | 31.7 | 0.205 | 0.4075 | 0.6125 | 0.7325 |
| | 31.8 | 0.2075 | 0.4075 | 0.615 | 0.7375 |
| | 31.9 | 0.2075 | 0.4075 | 0.615 | 0.7375 |
| | 32.0 | 0.2075 | 0.4100 | 0.6175 | 0.74 |
| | 32.1 | 0.21 | 0.4100 | 0.62 | 0.7425 |
| | 32.2 | 0.21 | 0.4125 | 0.6225 | 0.745 |
| | 32.3 | 0.21 | 0.4150 | 0.625 | 0.75 |
| | 32.4 | 0.21 | 0.4175 | 0.6275 | 0.7525 |
| | 32.5 | 0.2125 | 0.4175 | 0.63 | 0.755 |
| | 32.6 | 0.215 | 0.4200 | 0.635 | 0.76 |
| | 32.7 | 0.215 | 0.4225 | 0.6375 | 0.7625 |
| | 32.8 | 0.215 | 0.4250 | 0.64 | 0.765 |
| | 32.9 | 0.215 | 0.4250 | 0.64 | 0.7675 |
| | 33.0 | 0.2175 | 0.4250 | 0.6425 | 0.77 |
| | 33.1 | 0.2175 | 0.4275 | 0.645 | 0.7725 |
| | 33.2 | 0.2175 | 0.4300 | 0.6475 | 0.7775 |
| | 33.3 | 0.22 | 0.4325 | 0.6525 | 0.78 |
| | 33.4 | 0.22 | 0.4325 | 0.6525 | 0.71325 |
| | 33.5 | 0.22 | 0.4350 | 0.655 | 0.785 |
| | 33.6 | 0.22 | 0.4375 | 0.6575 | 0.7875 |
| | 33.7 | 0.2225 | 0.4400 | 0.6625 | 0.7925 |
| | 33.8 | 0.2225 | 0.4400 | 0.6625 | 0.7925 |
| | 33.9 | 0.2225 | 0.4425 | 0.665 | 0.7975 |
| | 34.0 | 0.225 | 0.4450 | 0.67 | 0.8 |
| | 34.1 | 0.225 | 0.4450 | 0.67 | 0.8025 |
| | 34.2 | 0.225 | 0.4475 | 0.6725 | 0.805 |
| | 34.3 | 0.2275 | 0.4500 | 0.6775 | 0.81 |
| | 34.4 | 0.2275 | 0.4500 | 0.6775 | 0.8125 |
| | 34.5 | 0.2275 | 0.4525 | 0.68 | 0.815 |
| | 34.6 | 0.23 | 0.4525 | 0.6825 | 0.8175 |
| | 34.7 | 0.23 | 0.4550 | 0.685 | 0.82 |
| | 34.8 | 0.2325 | 0.4575 | 0.69 | 0.825 |
| | 34.9 | 0.2325 | 0.4575 | 0.69 | 0.8275 |
| | 35.0 | 0.235 | 0.4600 | 0.695 | 0.83 |
| | 35.1 | 0.235 | 04600 | 0.695 | 0.8325 |
| | 35.2 | 0.2375 | 0.4625 | 0.7 | 0.8375 |
| | 35.3 | 0.235 | 0.4650 | 0.7 | 0.84 |
| | 35.4 | 0.2375 | 0.4675 | 0.705 | 0.8425 |
| | 35.5 | 0.2375 | 0.4675 | 0.705 | 0.845 |
| | 35.6 | 0.24 | 0.4700 | 0.71 | 0.85 |
| | 35.7 | 0.24 | 0.4700 | 0.71 | 0.85 |
| | 35.8 | 0.24 | 0.4725 | 0.7125 | 0.8525 |
| | 35.9 | 0.24 | 0.4750 | 0.715 | 0.8575 |
| | 36.0 | 0.2425 | 0.4750 | 0.7175 | 0.86 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 36.1 | 0.245 | 04775 | 0.7225 | 0.865 |
| 36.2 | 0.2425 | 0.4800 | 0.7225 | 0.8675 |
| 36.3 | 0.245 | 0.4800 | 0.725 | 0.8675 |
| 36.4 | 0.2475 | 0.4825 | 0.73 | 0.8725 |
| 36.5 | 0.245 | 0.4850 | 0.73 | 0.875 |
| 36.6 | 0.2475 | 0.4850 | 0.7325 | 0.8775 |
| 36.7 | 0.25 | 0.4875 | 0.7375 | 0.8825 |
| 36.8 | 0.2475 | 0.4900 | 0.7375 | 0.885 |
| 36.9 | 0.25 | 0.4900 | 0.74 | 0.8875 |
| 37.0 | 0.2525 | 0.4925 | 0.745 | 0.8925 |
| 37.1 | 0.2525 | 04950 | 0.7475 | 0895 |
| 37.2 | 0.2525 | 0.4950 | 0.7475 | 0.8975 |
| 37.3 | 0.2525 | 0.4975 | 0.75 | 0.9 |
| 37.4 | 0.255 | 0.5000 | 0.755 | 0.905 |
| 37.5 | 0.255 | 0.5025 | 0.7575 | 0.9075 |
| 37.6 | 0.2575 | 0.5025 | 0.76 | 0.91 |
| 37.7 | 0.255 | 0.5050 | 0.76 | 0.9125 |
| 37.8 | 0.2575 | 0.5050 | 0.7625 | 0.915 |
| 37.9 | 0.2575 | 0.5100 | 0.7675 | 0.92 |
| 38.0 | 0.26 | 0.5100 | 0.77 | 0.9225 |
| 38.1 | 0.26 | 0.5125 | 0.7725 | 0.925 |
| 38.2 | 0.2625 | 05125 | 0.775 | 0.9275 |
| 38.3 | 0.2625 | 0.5150 | 0.7775 | 0.93 |
| 38.4 | 0.265 | 0.5150 | 0.78 | 0.9325 |
| 38.5 | 0.265 | 0.5175 | 0.7825 | 0.9375 |
| 38.6 | 0.265 | 0.5200 | 0.785 | 0.94 |
| 38.7 | 0.265 | 0.5225 | 0.7875 | 0.945 |
| 38.8 | 0.265 | 0.5250 | 0.79 | 0.9475 |
| 38.9 | 0.2675 | 0.5250 | 0.7925 | 0.95 |
| 39.0 | 0.2675 | 0.5275 | 0.795 | 0.9525 |
| 39.1 | 0.2675 | 0.5300 | 0.7975 | 0.9575 |
| 39.2 | 0.27 | 05300 | 0.8 | 0.96 |
| 39.3 | 0.2725 | 0.5325 | 0.805 | 0.9625 |
| 39.4 | 0.2725 | 0.5350 | 0.8075 | 0.965 |
| 39.5 | 0.275 | 0.5350 | 0.81 | 0.97 |
| 39.6 | 0.275 | 0.5375 | 0.8125 | 0.9725 |
| 39.7 | 0.275 | 0.5400 | 0.815 | 0.975 |
| 39.8 | 0.275 | 0.5425 | 0.8175 | 0.98 |
| 39.9 | 0.2775 | 0.5425 | 0.82 | 0.9825 |
| 40.0 | 0.2775 | 0.5425 | 0.82 | 0.9825 |
| 40.1 | 0.2775 | 0.5450 | 0.8225 | 0.9875 |
| 40.2 | 0.2775 | 0.5475 | 0.825 | 0.99 |
| 40.3 | 0.28 | 0.5509 | 0.83 | 0.9925 |
| 40.4 | 0.2825 | 0.5500 | 0.8325 | 0.9975 |
| 40.5 | 0.2825 | 0.5525 | 0.835 | 1 |
| 40.6 | 0.2825 | 0.5550 | 0.8375 | 1.0025 |
| 40.7 | 0.2325 | 0.5575 | 0.84 | 1.0075 |
| 40.8 | 0.2825 | 0.5575 | 0.84 | 1.0075 |
| 40.9 | 0.285 | 0.5600 | 0.845 | 1.0125 |
| 41.0 | 0.2875 | 0.5600 | 0.8475 | 1.015 |
| 41.1 | 0.2875 | 0.5625 | 0.85 | 1.02 |
| 41.2 | 0.2875 | 0.5650 | 0.8525 | 1.0225 |
| 41.3 | 0.29 | 0.5659 | 0.855 | 1.025 |
| 41.4 | 0.29 | 0.5675 | 0.8575 | 1.0275 |
| 41.5 | 0.29 | 0.5700 | 0.86 | 1.0325 |
| 41.6 | 0.2925 | 0.5725 | 0.865 | 1.035 |
| 41.7 | 0.2925 | 0.5750 | 0.8675 | 1.04 |
| 41.8 | 0.2925 | 0.5750 | 0.8675 | 1.134 |
| 41.9 | 0.295 | 0.5775 | 0.8725 | 1.045 |
| 42.0 | 0.295 | 0.5800 | 0.875 | 1.0475 |
| 42.1 | 0.295 | 0.5800 | 0.875 | 1.05 |
| 42.2 | 0.2975 | 0.5825 | 0.88 | 1.0525 |
| 42.3 | 0.2975 | 0.5850 | 0.8825 | 1.0575 |
| 42.4 | 0.2975 | 0.5850 | 0.8825 | 1.06 |
| 42.5 | 0.3 | 0.5875 | 0.8875 | 1.0625 |
| 42.6 | 0.3 | 0.5900 | 0.89 | 1.0675 |
| 42.7 | 0.3025 | 0.5900 | 0.8925 | 1.0675 |
| 42.8 | 0.3025 | 0.5925 | 0.395 | 1.0725 |
| 42.9 | 0.305 | 0.5950 | 0.9 | 1.0775 |
| 43.0 | 0.305 | 0.5950 | 0.9 | 1.0775 |
| 43.1 | 0.305 | 0.5975 | 0.9025 | 1.0825 |
| 43.2 | 0.305 | 0.6000 | 0.905 | 1.085 |
| 43.3 | 0.305 | 0.6025 | 0.9075 | 1.09 |
| 43.4 | 0.3075 | 0.6050 | 0.9125 | 1.11925 |
| 43.5 | 0.3075 | 0.6050 | 0.9125 | 1.095 |
| 43.6 | 0.31 | 0.6075 | 0.9175 | 1.1 |
| 43.7 | 0.31 | 0.6075 | 0.9175 | 1.1 |
| 43.8 | 0.3125 | 0.6100 | 0.9225 | 1.105 |
| 43.9 | 0.3125 | 0.6125 | 0.925 | 1.1075 |
| 44.0 | 03125 | 0.6150 | 0.9275 | 1.1125 |
| 44.1 | 0.315 | 0.6150 | 0.93 | 1.1125 |
| 44.2 | 0.315 | 0.6175 | 0.9325 | 1.1175 |
| 44.3 | 0.3175 | 0.6175 | 0.935 | 1.12 |
| 44.4 | 0.315 | 0.6225 | 0.9375 | 1.1213 |
| 44.5 | 0.3175 | 0.6225 | 0.94 | 1.1275 |
| 44.6 | 0.32 | 0.6250 | 0.945 | 1.1325 |
| 44.7 | 0.32 | 0.6250 | 0.945 | 1.1325 |
| 44.8 | 0.32 | 0.6300 | 0.95 | 1.1375 |
| 44.9 | 0.32 | 0.6300 | 0.95 | 1.14 |
| 45.0 | 0.3225 | 0.6300 | 0.9525 | 1.1425 |
| 45.1 | 0.3225 | 0.6350 | 0.9575 | 1.1475 |
| 45.2 | 0.3225 | 0.6350 | 0.9575 | 1.15 |
| 45.3 | 0.325 | 0.6375 | 0.9625 | 1.155 |
| 45.4 | 0.3275 | 0.6375 | 0.965 | 1.155 |
| 45.5 | 0.3275 | 0.6400 | 0.9675 | 1.1575 |
| 45.6 | 0.3275 | 0.6425 | 0.97 | 1.1625 |
| 45.7 | 0.33 | 0.6425 | 0.9725 | 1.165 |
| 45.8 | 0.33 | 0.6475 | 0.9775 | 1.17 |
| 45.9 | 0.33 | 0.6475 | 0.9775 | 1.1725 |
| 46.0 | 0.33 | 0.6509 | 0.93 | 1.175 |
| 46.1 | 0.3325 | 0.6525 | 0.985 | 1.18 |
| 46.2 | 0.335 | 0.6525 | 0.9875 | 1.1825 |
| 46.3 | 0.3325 | 0.6550 | 0.9875 | 1.185 |
| 46.4 | 0.335 | 0.6550 | 0.99 | 1.1375 |
| 46.5 | 0.335 | 0.6600 | 0.995 | 1.1925 |
| 46.6 | 0.3375 | 0.6600 | 0.9975 | 1.195 |
| 46.7 | 0.34 | 0.6600 | 1 | 1.1975 |
| 46.8 | 0.3375 | 0.6650 | 1.0025 | 1.2025 |
| 46.9 | 0.34 | 0.6650 | 1.005 | 1.205 |
| 47.0 | 0.34 | 0.6675 | 1.0075 | 1.2075 |
| 47.1 | 0.3425 | 0.6675 | 1.01 | 1.21 |
| 47.2 | 0.3425 | 0.6725 | 1.015 | 1.215 |
| 47.3 | 0.345 | 0.6725 | 1.0175 | 1.2175 |
| 47.4 | 0.3425 | 0.6750 | 1.0175 | 1.22 |
| 47.5 | 0.345 | 0.6750 | 1.02 | 1.2225 |
| 47.6 | 0.345 | 0.6775 | 1.0225 | 1.2275 |
| 47.7 | 0.3475 | 0.6800 | 1.0275 | 1.2325 |
| 47.8 | 0.3475 | 0.6825 | 1.03 | 1.235 |
| 47.9 | 0.35 | 0.6825 | 1.0325 | 1.2375 |
| 48.0 | 0.35 | 0.6850 | 1.035 | 1.24 |
| 48.1 | 0.3525 | 0.6850 | 1.0375 | 1.2425 |
| 48.2 | 0.3525 | 0.6900 | 1.0425 | 1.2475 |
| 48.3 | 0.3525 | 0.6925 | 1.045 | 1.25 |
| 43.4 | 0.355 | 0.6925 | 1.0475 | 1.255 |
| 48.5 | 0.3525 | 0.6950 | 1.0475 | 1.2575 |
| 48.6 | 0.355 | 0.6950 | 1.05 | 1.26 |
| 48.7 | 0.355 | 0.6975 | 1.0525 | 1.2625 |
| 48.8 | 0.355 | 0.7000 | 1.055 | 1.265 |
| 48.9 | 0.3575 | 0.7000 | 1.0575 | 1.27 |
| 49.0 | 0.3575 | 0.7050 | 1.0625 | 1.275 |
| 49.1 | 0.36 | 0.7050 | 1.065 | 1.2775 |
| 49.2 | 0.36 | 0.7075 | 1.0675 | 1.28 |
| 49.3 | 0.36 | 0.7100 | 1.07 | 1.2825 |
| 49.4 | 0.3625 | 0.7100 | 1.0725 | 1.2375 |
| 49.5 | 0.3625 | 0.7125 | 1.975 | 1.29 |
| 49.6 | 0.3625 | 0.7150 | 1.0775 | 1.2925 |
| 49.7 | 0.365 | 0.7150 | 1.08 | 1.295 |
| 49.8 | 0.3675 | 0.7175 | 1.085 | 1.3 |
| 49.9 | 0.3675 | 0.7200 | 1.0875 | 1.3025 |
| 50.0 | 0.37 | 0.7200 | 1.09 | 1.305 |
| 50.1 | 0.37 | 0.7225 | 1.0925 | 1.3075 |
| 50.2 | 0.37 | 0.7250 | 1.095 | 1.3125 |
| 50.3 | 0.37 | 0.7275 | 1.0975 | 1.315 |
| 50.4 | 0.3725 | 0.7275 | 1.1 | 1.3175 |
| 50.5 | 0.3725 | 0.7300 | 1.1025 | 1.3225 |
| 50.6 | 0.3725 | 0.7325 | 1.105 | 1.325 |
| 50.7 | 0.375 | 0.7325 | 1.1075 | 1.3275 |
| 50.8 | 0.375 | 0.7350 | 1.11 | 1.3325 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 50.9 | 0.375 | 0.7375 | 1.1125 | 1.335 |
| 51.0 | 0.3775 | 0.7400 | 1.1175 | 1.3375 |
| 51.1 | 0.38 | 0.7400 | 1.12 | 1.3425 |
| 51.2 | 0.38 | 0.7425 | 1.1225 | 1.345 |
| 51.3 | 0.38 | 0.7450 | 1.125 | 1.3475 |
| 51.4 | 0.38 | 0.7475 | 1.1275 | 1.3525 |
| 51.5 | 0.38 | 0.7500 | 1.13 | 1.355 |
| 51.6 | 0.335 | 0.7500 | 1.135 | 1.36 |
| 51.7 | 0.385 | 0.7525 | 1.1375 | 1.3625 |
| 51.8 | 0.385 | 0.7550 | 1.14 | 1.365 |
| 51.9 | 0.385 | 0.7550 | 1.14 | 1.3675 |
| 52.0 | 0.385 | 0.7575 | 1.1425 | 1.37 |
| 52.1 | 0.385 | 0.7600 | 1.145 | 1.375 |
| 52.2 | 0.39 | 0.7600 | 1.15 | 1.3775 |
| 52.3 | 0.39 | 0.7625 | 1.1525 | 1.38 |
| 52.4 | 0.39 | 0.7650 | 1.155 | 1.385 |
| 52.5 | 0.39 | 0.7675 | 1.1575 | 1.3875 |
| 52.6 | 0.3925 | 0.7700 | 1.1625 | 1.3925 |
| 52.7 | 0.3925 | 0.7700 | 1.1625 | 1.3925 |
| 52.8 | 0.3925 | 0.7725 | 1.165 | 1.3975 |
| 52.9 | 0.395 | 0.7725 | 1.1675 | 1.4 |
| 53.0 | 0.3975 | 0.7750 | 1.1725 | 1.405 |
| 53.1 | 0.3975 | 0.7775 | 1.175 | 1.4075 |
| 53.2 | 0.3975 | 0.7800 | 1.1775 | 1.4125 |
| 53.3 | 0.3975 | 0.7800 | 1.1775 | 1.4125 |
| 53.4 | 0.4 | 0.7825 | 1.1825 | 1.415 |
| 53.5 | 0.4 | 0.7850 | 1.185 | 1.42 |
| 53.6 | 0.4 | 0.7875 | 1.1875 | 1.4225 |
| 53.7 | 0.4025 | 0.7900 | 1.1925 | 1.4275 |
| 53.3 | 0.4025 | 0.7925 | 1.195 | 1.4325 |
| 53.9 | 0.4025 | 0.7925 | 1.195 | 1.4325 |
| 54.0 | 0.4025 | 0.7950 | 1.1975 | 1.4375 |
| 54.1 | 0.4075 | 0.7950 | 1.2025 | 1.44 |
| 54.2 | 0.4075 | 0.7975 | 1.205 | 1.445 |
| 54.3 | 0.4075 | 0.7975 | 1.205 | 1.445 |
| 54.4 | 0.41 | 0.8000 | 1.21 | 1.45 |
| 54.5 | 0.41 | 0.8025 | 1.2125 | 1.4525 |
| 54.6 | 0.41 | 0.8050 | 1.215 | 1.4575 |
| 54.7 | 0.4125 | 0.8050 | 1.2.175 | 1.4575 |
| 54.8 | 0.4125 | 0.8075 | 1.22 | 1.4625 |
| 54.9 | 0.4125 | 0.8100 | 1.2225 | 1.465 |
| 55.0 | 0.415 | 0.8125 | 1.2275 | 1.47 |
| 55.1 | 0.415 | 0.8125 | 1.2275 | 1.4725 |
| 55.2 | 0.4175 | 0.8150 | 1.2325 | 1.475 |
| 55.3 | 0.4175 | 0.8175 | 1.235 | 1.48 |
| 55.4 | 0.4175 | 0.8175 | 1.235 | 1.43 |
| 55.5 | 0.42 | 0.8200 | 1.24 | 1.485 |
| 55.6 | 0.42 | 0.8225 | 1.2425 | 1.49 |
| 55.7 | 0.4225 | 0.8250 | 1.2475 | 1.4925 |
| 55.8 | 0.4225 | 0.8250 | 1.2475 | 1.495 |
| 55.9 | 0.4225 | 0.3275 | 1.25 | 1.4975 |
| 56.0 | 0.4225 | 0.8325 | 1.255 | 1.5025 |
| 56.1 | 0.4225 | 0.8325 | 1.255 | 1.505 |
| 56.2 | 0.425 | 0.8350 | 1.26 | 1.5075 |
| 56.3 | 0.425 | 0.8375 | 1.2625 | 1.5125 |
| 56.4 | 0.425 | 0.8375 | 1.2625 | 1.515 |
| 56.5 | 0.4275 | 0.8400 | 1.2675 | 1.5175 |
| 56.6 | 0.4275 | 0.8425 | 1.27 | 1.5225 |
| 55.7 | 0.43 | 0.8425 | 1.2725 | 1.525 |
| 56.8 | 0.43 | 0.8450 | 1.275 | 1.5275 |
| 56.9 | 0.4325 | 0.3475 | 1.28 | 1.5325 |
| 57.0 | 0.4325 | 0.8475 | 1.28 | 1.535 |
| 57.1 | 0.435 | 0.8500 | 1.285 | 1.5375 |
| 57.2 | 0.435 | 0.8500 | 1.285 | 1.54 |
| 57.3 | 0.4325 | 0.8550 | 1.2875 | 1.545 |
| 57.4 | 0.435 | 0.8575 | 1.2.925 | 1.5475 |
| 57.5 | 0.435 | 0.8575 | 1.2925 | 1.55 |
| 57.6 | 0.4375 | 0.8600 | 1.2975 | 1.555 |
| 57.7 | 0.4375 | 0.8625 | 1.3 | 1.5575 |
| 57.8 | 0.44 | 0.3625 | 1.3025 | 1.56 |
| 57.9 | 0.44 | 0.3650 | 1.305 | 1.565 |
| 58.0 | 0.4425 | 0.8650 | 1.3075 | 1.565 |
| 58.1 | 0.44 | 0.8700 | 1.31 | 1.57 |
| 58.2 | 0.4425 | 0.8725 | 1.315 | 1.575 |
| 58.3 | 0.4425 | 0.8725 | 1.315 | 1.5775 |
| 58.4 | 0.445 | 0.8750 | 1.32 | 1.5(3 |
| 58.5 | 0.445 | 0.8750 | 1.32 | 1.5825 |
| 58.6 | 0.4475 | 0.8775 | 1.325 | 1.5875 |
| 58.7 | 0.445 | 0.8800 | 1.325 | 1.5875 |
| 58.8 | 0.4475 | 0.8825 | 1.33 | 1.5925 |
| 58.9 | 0.4475 | 0.3850 | 1.3325 | 1.5975 |
| 59.0 | 0.45 | 0.3850 | 1.335 | 1.6 |
| 59.1 | 0.4525 | 0.8875 | 1.34 | 1.6025 |
| 59.2 | 0.4525 | 0.8875 | 1.34 | 1.605 |
| 59.3 | 0.4525 | 0.8925 | 1.345 | 1.61 |
| 59.4 | 0.4525 | 0.8925 | 1.345 | 1.6125 |
| 59.5 | 0.455 | 0.8950 | 1.35 | 1.615 |
| 59.6 | 0.455 | 0.8950 | 1.35 | 1.6175 |
| 59.7 | 0.4575 | 0.8975 | 1.355 | 1.6225 |
| 59.8 | 0.455 | 0.9000 | 1.355 | 1.625 |
| 59.9 | 0.4575 | 0.9025 | 1.36 | 1.6275 |
| 60.0 | 0.46 | 0.9025 | 1.3625 | 1.63 |
| 60.1 | 0.46 | 0.9050 | 1.365 | 1.635 |
| 60.2 | 0.4625 | 0.9050 | 1.3675 | 1.5375 |
| 60.3 | 0.46 | 0.9100 | 1.37 | 1.6425 |
| 60.4 | 0.4625 | 0.9125 | 1.375 | 1.645 |
| 60.5 | 0.4625 | 0.9125 | 1.375 | 1.6475 |
| 60.6 | 0.485 | 0.9150 | 1.38 | 1.6525 |
| 60.7 | 0.465 | 0.9175 | 1.3825 | 1.655 |
| 60.8 | 0.465 | 0.9200 | 1.385 | 1.6575 |
| 60.9 | 0.4675 | 0.9200 | 1.3875 | 1.66 |
| 61.0 | 0.4675 | 0.9200 | 1.3875 | 1.5625 |
| 61.1 | 0.47 | 0.9225 | 1.3925 | 1.6675 |
| 61.2 | 0.47 | 0.9250 | 1.395 | 1.671 |
| 61.3 | 0.47 | 0.9275 | 1.3975 | 1.6725 |
| 61.4 | 0.4725 | 0.9275 | 1.4 | 1.675 |
| 61.5 | 0.4725 | 0.9300 | 1.4025 | 1.58 |
| 61.6 | 0.4725 | 0.9325 | 1.405 | 1.6325 |
| 61.7 | 0.475 | 0.9350 | 1.41 | 1.6875 |
| 61.8 | 0.475 | 0.9350 | 1.41 | 1.69 |
| 61.9 | 0.475 | 0.9400 | 1.415 | 1.5925 |
| 62.0 | 0.4775 | 0.9400 | 1.4175 | 1.695 |
| 62.1 | 0.4775 | 0.9425 | 1.42 | 1.7 |
| 62.2 | 0.48 | 0.9425 | 1.4225 | 1.7025 |
| 62.3 | 0.4775 | 0.9475 | 1.425 | 1.7075 |
| 62.4 | 0.48 | 0.9475 | 1.4275 | 1.71 |
| 62.5 | 0.4825 | 0.9475 | 1.43 | 1.71 |
| 62.6 | 0.48 | 0.9525 | 1.4325 | 1.715 |
| 62.7 | 0.4825 | 0.9525 | 1.435 | 1.7175 |
| 62.8 | 0.485 | 0.9550 | 1.44 | 1.7225 |
| 62.9 | 0.485 | 0.9550 | 1.44 | 1.725 |
| 63.0 | 0.435 | 0.9600 | 1.445 | 1.73 |
| 63.1 | 0.4875 | 0.9600 | 1.4475 | 1.73 |
| 63.2 | 0.4875 | 0.9625 | 1.45 | 1.735 |
| 63.3 | 1)4875 | 0.9650 | 1.4525 | 1.7375 |
| 63.4 | 0.49 | 0.9550 | 1.455 | 1.74 |
| 63.5 | 0.49 | 0.9675 | 1.4575 | 1.745 |
| 63.6 | 0.49 | 0.9790 | 1.46 | 1.7475 |
| 63.7 | 0.4925 | 0.9725 | 1.465 | 1.7525 |
| 63.8 | 0.4925 | 0.9725 | 1.465 | 1.7525 |
| 63.9 | 0.495 | 0.9725 | 1.4675 | 1.755 |
| 64.0 | 0.495 | 0.9775 | 1.4725 | 1.76 |
| 64.1 | 0.495 | 0.9775 | 1.4725 | 1.7825 |
| 64.2 | 0.4975 | 0.9800 | 1.4775 | 1.7875 |
| 64.3 | 0.4975 | 0.9825 | 1.48 | 1.77 |
| 64.4 | 0.4975 | 0.9850 | 1.4825 | 1.775 |
| 64.5 | 0.5 | 0.9850 | 1.485 | 1.7775 |
| 64.6 | 0.5 | 0.9375 | 1.4375 | 1.7775 |
| 64.7 | 0.5 | 0.9900 | 1.49 | 1.7325 |
| 64.8 | 0.5025 | 0.9900 | 1.4925 | 1.785 |
| 64.9 | 0.5025 | 0.9950 | 1.4975 | 1.79 |
| 65.0 | 0.5025 | 0.9950 | 1.4975 | 1.7925 |
| 65.1 | 0.505 | 0.9950 | 1.5 | 1.795 |
| 65.2 | 0.505 | 1.0000 | 1.505 | 1.8 |
| 65.3 | 0.505 | 1.0000 | 1.505 | 1.8025 |
| 65.4 | 0.505 | 1.0025 | 1.5075 | 1.805 |
| 65.5 | 0.5075 | 1.0050 | 1.5125 | 1.8075 |
| 65.6 | 0.51 | 1.0050 | 1.515 | 1.81 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 65.7 | 0.5075 | 1.0100 | 1.5175 | 1.815 |
| 85.3 | 0.51 | 1.0100 | 1.52 | 1.8175 |
| 65.9 | 0.5125 | 1.0100 | 1.5225 | 1.82 |
| 66.0 | 0.51 | 1.0150 | 1.525 | 1.825 |
| 65.1 | 0.5125 | 1.0150 | 1.5275 | 1.8275 |
| 65.2 | 0.515 | 1.0150 | 1.53 | 1.83 |
| 66.3 | 0.515 | 1.0200 | 1.535 | 1.335 |
| 66.4 | 0.515 | 1.0200 | 1.535 | 1.8375 |
| 66.5 | 0.5175 | 1.0225 | 1.54 | 1.84 |
| 66.6 | 0.5175 | 1.0250 | 1.5425 | 1.8425 |
| 68.7 | 0.5175 | 1.0250 | 1.5425 | 1.845 |
| 86.3 | 0.5175 | 1.0300 | 1.5475 | 1.35 |
| 66.9 | 0.52 | 1.0300 | 1.55 | 1.8525 |
| 67.0 | 0.5225 | 1.0300 | 1.5525 | 1.855 |
| 67.1 | 0.52 | 1.0350 | 1.555 | 1.86 |
| 67.2 | 0.5225 | 1.0350 | 1.5575 | 1.8625 |
| 67.3 | 0.525 | 1.0375 | 1.5625 | 1.8675 |
| 67.4 | 0.5225 | 1.0400 | 1.5625 | 1.87 |
| 67.5 | 0.525 | 1.0400 | 1.565 | 1.8725 |
| 67.6 | 0.525 | 1.0450 | 1.57 | 1.8775 |
| 67.7 | 0.5275 | 1.0450 | 1.5725 | 1.8775 |
| 67.3 | 0.5275 | 1.0450 | 1.5725 | 1.88 |
| 67.9 | 0.5275 | 1.0500 | 1.5775 | 1.885 |
| 68.0 | 0.53 | 1.0500 | 1.58 | 1.8875 |
| 68.1 | 0.53 | 1.0525 | 1.5825 | 1.89 |
| 68.2 | 0.53 | 1.0550 | 1.585 | 1.395 |
| 68.3 | 0.5325 | 1.0550 | 1.5375 | 1.8975 |
| 68.4 | 0.5325 | 1.0575 | 1.59 | 1.9 |
| 68.5 | 0.535 | 1.0600 | 1.595 | 1.905 |
| 68.6 | 0.5325 | 1.0625 | 1.595 | 1.9075 |
| 68.7 | 0.535 | 1.0825 | 1.5975 | 1.91 |
| 68.8 | 0.5375 | 1.0650 | 1.6025 | 1.915 |
| 68.9 | 0.535 | 1.0675 | 1.6025 | 1.9175 |
| 69.0 | 0.5375 | 1.0675 | 1.605 | 1.92 |
| 69.1 | 0.5375 | 1.0725 | 1.61 | 1.9225 |
| 69.2 | 0.54 | 1.0725 | 1.6125 | 1.925 |
| 69.3 | 0.54 | 1.0750 | 1.615 | 1.93 |
| 69.4 | 0.54 | 1.0775 | 1.6175 | 1.9325 |
| 69.5 | 0.5425 | 1.0775 | 1.62 | 1.935 |
| 69.6 | 0.5425 | 1.0825 | 1.625 | 1.94 |
| 69.7 | 0.5425 | 1.0825 | 1.625 | 1.9425 |
| 89.8 | 0.545 | 1.0825 | 1.6275 | 1.945 |
| 89.9 | 0.545 | 1.0875 | 1.6325 | 1.95 |
| 70.0 | 0.5475 | 1.0875 | 1.635 | 1.9525 |
| 70.1 | 0.545 | 1.0900 | 1.635 | 1.955 |
| 70.2 | 0.5475 | 1.0925 | 1.64 | 1.96 |
| 70.3 | 0.55 | 1.0925 | 1.6425 | 1.9625 |
| 70.4 | 0.55 | 1.0950 | 1.645 | 1.965 |
| 70.5 | 0.5525 | 1.0975 | 1.65 | 1.97 |
| 70.6 | 0.55 | 1.1000 | 1.65 | 1.9725 |
| 70.7 | 0.5525 | 1.1000 | 1.6525 | 1.975 |
| 70.8 | 0.555 | 1.1025 | 1.6575 | 1.98 |
| 70.9 | 0.555 | 1.1051 | 1.66 | 1.98 |
| 71.0 | 0.555 | 1.1950 | 1.66 | 1.9825 |
| 71.1 | 0.555 | 1.1100 | 1.665 | 1.9875 |
| 71.2 | 0.5575 | 1.1100 | 1.6675 | 1.99 |
| 71.3 | 0.5575 | 1.1125 | 1.67 | 1.9925 |
| 71.4 | 0.5575 | 1.1150 | 1.6725 | 1.9975 |
| 71.5 | 0.56 | 1.1159 | 1.675 | 2 |
| 71.6 | 0.56 | 1.1175 | 1.6775 | 2.9025 |
| 71.7 | 0.5625 | 1.1200 | 1.6825 | 2.0075 |
| 71.8 | 0.56 | 1.1225 | 1.6825 | 2.01 |
| 71.9 | 0.5625 | 1.1225 | 1.685 | 2.0125 |
| 72.0 | 0.565 | 1.1250 | 1.69 | 2.0175 |
| 72.1 | 0.565 | 1.1275 | 1.6925 | 2.92 |
| 72.2 | 0.565 | 1.1275 | 1.6925 | 2.0225 |
| 72.3 | 0.565 | 1.1325 | 1.6975 | 2.0275 |
| 72.4 | 0.5675 | 1.1325 | 1.7 | 2.03 |
| 72.5 | 0.5675 | 1.1359 | 1.7025 | 2.9325 |
| 72.6 | 0.57 | 1.1375 | 1.7075 | 2.9375 |
| 72.7 | 0.57 | 1.1375 | 1.7075 | 2.04 |
| 72.8 | 0.57 | 1.1400 | 1.71 | 2.0425 |
| 72.9 | 0.5725 | 1.1425 | 1.715 | 2.0475 |
| 73.0 | 0.5725 | 1.1450 | 1.7175 | 2.0475 |
| 73.1 | 0.5725 | 1.1450 | 1.7175 | 2.95 |
| 73.2 | 0.575 | 1.1475 | 1.7225 | 2.055 |
| 73.3 | 0.575 | 1.1500 | 1.725 | 2.0575 |
| 73.4 | 0.5775 | 1.1509 | 1.7275 | 2.06 |
| 73.5 | 0.575 | 1.1550 | 1.73 | 2.065 |
| 73.6 | 0.5775 | 1.1550 | 1.7325 | 2.0675 |
| 73.7 | 0.5775 | 1.1575 | 1.735 | 2.07 |
| 73.8 | 0.58 | 1.1600 | 1.74 | 2.085 |
| 73.9 | 0.5825 | 1.1600 | 1.7425 | 2.0775 |
| 74.0 | 0.58 | 1.1650 | 1.745 | 2.0825 |
| 74.1 | 0.5825 | 1.1650 | 1.7475 | 2.085 |
| 74.2 | 0.5825 | 1.1675 | 1.75 | 2.0875 |
| 74.3 | 0.585 | 1.1700 | 1.755 | 2.0925 |
| 74.4 | 0.5825 | 1.1725 | 1.755 | 2.095 |
| 74.5 | 0.585 | 1.1725 | 1.7575 | 2.9975 |
| 74.6 | 0.5875 | 1.1759 | 1.7625 | 2.1025 |
| 74.7 | 0.5875 | 1.1775 | 1.765 | 2.105 |
| 74.8 | 0.5875 | 1.1775 | 1.765 | 2.1075 |
| 74.9 | 0.5875 | 1.1825 | 1.77 | 2.1125 |
| 75.0 | 0.59 | 1.1825 | 1.7725 | 2.115 |
| 75.1 | 0.5925 | 1.1825 | 1.775 | 2.1175 |
| 75.2 | 0.5925 | 1.1875 | 1.78 | 2.1225 |
| 75.3 | 0.5925 | 1.1875 | 1.78 | 2.125 |
| 75.4 | 0.5925 | 1.1909 | 1.7825 | 2.1275 |
| 75.5 | 0.595 | 1.1925 | 1.7875 | 2.13 |
| 75.6 | 0.595 | 1.1959 | 1.79 | 2.1325 |
| 75.7 | 0.595 | 1.1975 | 1.7925 | 2.1375 |
| 75.8 | 0.5975 | 1.1975 | 1.795 | 2.14 |
| 75.9 | 0.5975 | 1.2900 | 1.7975 | 2.1425 |
| 76.0 | 0.6 | 1.2925 | 1.8925 | 2.1475 |
| 76.1 | 0.5975 | 1.2950 | 1.8925 | 2.15 |
| 76.2 | 0.6 | 1.2059 | 1.805 | 2.1525 |
| 76.3 | 0.6025 | 1.2075 | 1.81 | 2.1575 |
| 76.4 | 0.6025 | 1.2100 | 1.8125 | 2.16 |
| 76.5 | 0.605 | 1.2125 | 1.8175 | 2.165 |
| 76.6 | 0.6025 | 1.2150 | 1.8175 | 2.1675 |
| 76.7 | 0.605 | 1.2150 | 1.82 | 2.17 |
| 76.8 | 0.6975 | 1.2175 | 1.825 | 2.175 |
| 76.9 | 0.6075 | 1.2200 | 1.8275 | 2.1775 |
| 77.0 | 0.6075 | 1.2200 | 1.8275 | 2.18 |
| 77.1 | 0.6075 | 1.2250 | 1.8325 | 2.185 |
| 77.2 | 0.61 | 1.2259 | 1.835 | 2.1875 |
| 77.3 | 0.61 | 1.2309 | 1.84 | 2.1925 |
| 77.4 | 0.61 | 1.2309 | 1.84 | 2.195 |
| 77.5 | 0.6125 | 1.2300 | 1.8425 | 2.1975 |
| 77.6 | 0.6125 | 1.2350 | 1.8475 | 2.2025 |
| 77.7 | 0.615 | 1.2350 | 1.85 | 2.295 |
| 77.8 | 0.615 | 1.2400 | 1.855 | 2.21 |
| 77.9 | 0.615 | 1.2400 | 1.855 | 2.2125 |
| 78.0 | 0.6175 | 1.2400 | 1.8575 | 2.2125 |
| 78.1 | 0.6175 | 1.2459 | 1.8625 | 2.2175 |
| 78.2 | 0.62 | 1.2459 | 1.865 | 2.22 |
| 78.3 | 0.6175 | 1.2509 | 1.8675 | 2.225 |
| 78.4 | 0.62 | 1.2509 | 1.87 | 2.2275 |
| 78.5 | 0.6225 | 1.2500 | 1.8725 | 2.23 |
| 78.6 | 0.6225 | 1.2550 | 1.8775 | 2.235 |
| 78.7 | 0.6225 | 1.2550 | 1.8775 | 2.2375 |
| 78.8 | 0.625 | 1.2575 | 1.8825 | 2.2425 |
| 78.9 | 0.625 | 1.2600 | 1.885 | 2.245 |
| 79.0 | 0.6275 | 1.2625 | 1.89 | 2.25 |
| 79.1 | 0.625 | 1.2659 | 1.89 | 2.2525 |
| 79.2 | 0.6275 | 1.2659 | 1.8925 | 2.255 |
| 79.3 | 0.63 | 1.2675 | 1.8975 | 2.26 |
| 79.4 | 0.63 | 1.2709 | 1.9 | 2.2625 |
| 79.5 | 0.63 | 1.2725 | 1.9025 | 2.2675 |
| 79.6 | 0.63 | 1.2750 | 1.995 | 2.27 |
| 79.7 | 0.6325 | 1.2775 | 1.91 | 2.275 |
| 79.8 | 0.635 | 1.2775 | 1.9125 | 2.2775 |
| 79.9 | 0.6325 | 1.2825 | 1.915 | 2.2825 |
| 80.0 | 0.635 | 1.2825 | 1.9175 | 2.285 |
| 80.1 | 0.6375 | 1.2825 | 1.92 | 2.2875 |
| 80.2 | 0.6375 | 1.2875 | 1.925 | 2.2925 |
| 80.3 | 0.6375 | 1.2875 | 1.925 | 2.2925 |
| 80.4 | 0.6375 | 1.2925 | 1.93 | 2.2975 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 80.5 | 0.64 | 1.2925 | 1.9325 | 2.3 |
| 80.6 | 0.6425 | 1.2950 | 1.9375 | 2.395 |
| 80.7 | 0.64 | 1.2975 | 1.9375 | 2.3075 |
| 80.8 | 0.6425 | 1.3900 | 1.9425 | 2.3125 |
| 80.9 | 0.645 | 1.3900 | 1.945 | 2.315 |
| 81.0 | 0.645 | 1.3050 | 1.95 | 2.32 |
| 81.1 | 0.645 | 1.3059 | 1.95 | 2.3225 |
| 81.2 | 0.6475 | 1.3075 | 1.955 | 2.3275 |
| 81.3 | 0.6475 | 1.3100 | 1.9575 | 2.33 |
| 81.4 | 0.65 | 1.3125 | 1.9625 | 2.335 |
| 81.5 | 0.6475 | 1.3150 | 1.9625 | 2.3375 |
| 81.6 | 0.65 | 1.3175 | 1.9675 | 2.3425 |
| 81.7 | 0.6525 | 1.3175 | 1.97 | 2.345 |
| 81.8 | 0.6525 | 1.3225 | 1.975 | 2.35 |
| 81.9 | 0.6525 | 1.3225 | 1.975 | 2.3525 |
| 82.0 | 0.655 | 1.3250 | 1.98 | 2.3575 |
| 82.1 | 0.655 | 1.3275 | 1.9825 | 2.36 |
| 82.2 | 0.6575 | 1.3300 | 1.9875 | 2.3625 |
| 82.3 | 0.6575 | 1.3300 | 1.9875 | 2.365 |
| 82.4 | 0.6575 | 1.3350 | 1.9925 | 2.37 |
| 82.5 | 0.66 | 1.3350 | 1.995 | 2.3725 |
| 82.6 | 0.66 | 1.3375 | 1.9975 | 2.3775 |
| 82.7 | 0.66 | 1.3400 | 2 | 2.38 |
| 82.8 | 0.6825 | 1.3425 | 2.005 | 2.385 |
| 82.9 | 0.665 | 1.3450 | 2.01 | 2.39 |
| 83.0 | 0.6625 | 1.3475 | 2.01 | 2.3925 |
| 83.1 | 0.665 | 1.3500 | 2.015 | 2.3975 |
| 83.2 | 0.6675 | 1.3500 | 2.0175 | 2.4 |
| 33.3 | 0.6675 | 1.3550 | 2.0225 | 2.405 |
| 83.4 | 0.6675 | 1.3550 | 2.0225 | 2.4075 |
| 83.5 | 0.67 | 1.3575 | 2.0275 | 2.4125 |
| 83.6 | 0.6725 | 1.3600 | 2.0325 | 2.4175 |
| 83.7 | 0.67 | 1.3625 | 2.0325 | 2.42 |
| 83.8 | 0.6725 | 1.3650 | 2.0375 | 2.4225 |
| 83.9 | 0.675 | 1.3650 | 2.04 | 2.425 |
| 84.0 | 0.675 | 1.3700 | 2.045 | 2.43 |
| 84.1 | 0.675 | 1.3700 | 2.045 | 2.4325 |
| 84.2 | 0.6775 | 1.3725 | 2.05 | 2.4375 |
| 34.3 | 0.6775 | 1.3775 | 2.055 | 2.4425 |
| 84.4 | 0.6775 | 1.3775 | 2.055 | 2.445 |
| 84.5 | 0.68 | 1.3800 | 2.06 | 2.45 |
| 84.6 | 0.6825 | 1.3825 | 2.065 | 2.455 |
| 84.7 | 0.68 | 1.3850 | 2.065 | 2.4575 |
| 84.8 | 0.6825 | 1.3875 | 2.07 | 2.4625 |
| 84.9 | 0.685 | 1.3875 | 2.0725 | 2.465 |
| 85.0 | 0.6825 | 1.3925 | 2.075 | 2.47 |
| 85.1 | 0.685 | 1.3950 | 2.08 | 2.4725 |
| 85.2 | 0.6875 | 1.3950 | 2.0825 | 2.475 |
| 35.3 | 0.69 | 1.3975 | 2.0875 | 2.48 |
| 85.4 | 0.6875 | 1.4025 | 2.09 | 2.485 |
| 85.5 | 0.69 | 1.4025 | 2.0925 | 2.4875 |
| 85.6 | 0.6925 | 1.4050 | 2.0975 | 2.4925 |
| 85.7 | 0.6925 | 1.4075 | 2.1 | 2.4975 |
| 85.8 | 0.6925 | 1.4100 | 2.1025 | 2.5 |
| 85.9 | 0.695 | 1.4125 | 2.1075 | 2.505 |
| 86.0 | 0.695 | 1.4150 | 2.11 | 2.51 |
| 86.1 | 0.6975 | 1.4150 | 2.1125 | 2.5125 |
| 85.2 | 0.6975 | 1.4200 | 2.1175 | 2.515 |
| 36.3 | 0.6975 | 1.4225 | 2.12 | 2.52 |
| 86.4 | 0.7 | 1.4250 | 2.125 | 2.525 |
| 86.5 | 0.7025 | 1.4250 | 2.1275 | 2.5275 |
| 86.6 | 0.7 | 1.4300 | 3.13 | 2.5325 |
| 86.7 | 0.7025 | 1.4325 | 2.135 | 2.5375 |
| 86.8 | 0.705 | 1.4350 | 2.14 | 2.5425 |
| 86.9 | 0.705 | 1.4350 | 2.14 | 2.545 |
| 87.0 | 0.7075 | 1.4375 | 2.145 | 2.55 |
| 87.1 | 0.7075 | 1.4425 | 2.15 | 2.5525 |
| 87.2 | 0.7075 | 1.4450 | 2.1525 | 2.5575 |
| 87.3 | 0.71 | 1.4450 | 2.155 | 2.56 |
| 87.4 | 0.71 | 1.4475 | 2.1575 | 2.565 |
| 87.5 | 0.7125 | 1.4500 | 2.1625 | 2.57 |
| 87.6 | 0.7125 | 1.4550 | 2.1675 | 2.575 |
| 87.7 | 0.7125 | 1.4550 | 2.1675 | 2.5775 |
| 87.8 | 0.715 | 1.4575 | 2.1725 | 2.5825 |
| 87.9 | 0.7175 | 1.4600 | 2.1775 | 2.5875 |
| 88.0 | 0.7175 | 1.4625 | 2.18 | 2.59 |
| 88.1 | 0.72 | 1.4650 | 2.185 | 2.595 |
| 88.2 | 0.72 | 1.4675 | 2.1875 | 2.5975 |
| 88.3 | 0.72 | 1.4700 | 2.19 | 2.6025 |
| 88.4 | 0.7225 | 1.4725 | 2.195 | 2.6075 |
| 88.5 | 0.7225 | 1.4750 | 2.1975 | 2.6125 |
| 88.6 | 0.725 | 1.4775 | 2.2025 | 2.6175 |
| 88.7 | 0.7275 | 1.4800 | 2.2075 | 2.62 |
| 88.8 | 0.7275 | 1.4825 | 2.21 | 2.625 |
| 88.9 | 0.7275 | 1.4850 | 2.2125 | 2.6275 |
| 39.0 | 0.7275 | 1.4875 | 2.215 | 2.6325 |
| 89.1 | 0.73 | 1.4900 | 2.22 | 2.6375 |
| 89.2 | 0.7325 | 1.4925 | 2.225 | 2.6425 |
| 89.3 | 0.7325 | 1.4950 | 2.2275 | 2.6475 |
| 89.4 | 0.735 | 1.4975 | 2.2325 | 2.65 |
| 89.5 | 0.735 | 1.5000 | 2.235 | 2.655 |
| 89.6 | 0.7375 | 1.5025 | 2.24 | 2.66 |
| 89.7 | 0.7375 | 1.5050 | 2.2425 | 2.665 |
| 89.8 | 0.7375 | 1.5100 | 2.2475 | 2.67 |
| 89.9 | 0.74 | 1.5125 | 2.2525 | 2.675 |
| 90.0 | 0.74 | 1.5125 | 2.2525 | 2.675 |
| 90.1 | 0.7425 | 1.5175 | 2.26 | 2.6825 |
| 90.2 | 0.7425 | 1.5175 | 2.26 | 2.685 |
| 90.3 | 0.745 | 1.5200 | 2.265 | 2.69 |
| 90.4 | 0.745 | 1.5225 | 2.2675 | 2.695 |
| 90.5 | 0.7475 | 1.5250 | 2.2725 | 2.7 |
| 90.6 | 0.75 | 1.5275 | 2.2775 | 2.7025 |
| 90.7 | 0.75 | 1.5300 | 2.28 | 2.7075 |
| 90.8 | 0.7525 | 1.5325 | 2.285 | 2.7125 |
| 90.9 | 0.7525 | 1.5350 | 2.2875 | 2.7175 |
| 91.0 | 0.755 | 1.5375 | 2.2925 | 2.7225 |
| 91.1 | 0.755 | 1.5425 | 2.2975 | 2.7275 |
| 91.2 | 0.7575 | 1.5450 | 2.3025 | 2.7275 |
| 91.3 | 0.7575 | 1.5475 | 2.305 | 2.7275 |
| 91.4 | 0.76 | 1.5500 | 2.31 | 2.7425 |
| 91.5 | 0.76 | 1.5525 | 2.3125 | 2.7475 |
| 91.6 | 0.7625 | 1.5550 | 2.3175 | 2.75 |
| 91.7 | 0.7625 | 1.5575 | 2.32 | 2.755 |
| 91.8 | 0.765 | 1.5600 | 2.325 | 2.76 |
| 91.9 | 0.765 | 1.5625 | 2.3275 | 2.765 |
| 92.0 | 0.7675 | 1.5650 | 2.3325 | 2.7675 |
| 92.1 | 0.7675 | 1.5675 | 2.335 | 2.7725 |
| 92.2 | 0.77 | 1.5725 | 2.3425 | 2.73 |
| 92.3 | 0.77 | 1.5750 | 2.345 | 2.785 |
| 92.4 | 0.7725 | 1.5775 | 2.35 | 2.79 |
| 92.5 | 0.7725 | 1.5800 | 2.3525 | 2.7925 |
| 92.6 | 0.7725 | 1.5825 | 2.355 | 2.7975 |
| 92.7 | 0.775 | 1.5850 | 2.36 | 2.8025 |
| 92.8 | 0.775 | 1.5875 | 2.3625 | 2.8075 |
| 92.9 | 0.7775 | 1.5925 | 2.37 | 2.8125 |
| 93.0 | 0.7775 | 1.5950 | 2.3725 | 2.8175 |
| 93.1 | 0.78 | 1.5975 | 2.3775 | 2.8225 |
| 93.2 | 0.7825 | 1.5975 | 2.38 | 2.825 |
| 93.3 | 0.785 | 1.6025 | 2.3875 | 2.8325 |
| 93.4 | 0.785 | 1.6050 | 2.39 | 2.8375 |
| 93.5 | 0.785 | 1.6075 | 2.3925 | 2.8425 |
| 93.6 | 0.7875 | 1.6100 | 2.3975 | 2.845 |
| 93.7 | 0.7875 | 1.6150 | 2.4025 | 2.8525 |
| 93.8 | 0.79 | 1.6175 | 2.4075 | 2.8575 |
| 93.9 | 0.7925 | 1.6175 | 2.41 | 2.66 |
| 94.0 | 0.7925 | 1.6225 | 2.415 | 2.8675 |
| 94.1 | 0.795 | 1.6250 | 2.42 | 2.8725 |
| 94.2 | 0.795 | 1.6275 | 2.4225 | 2.875 |
| 94.3 | 0.795 | 1.6325 | 2.4275 | 2.8825 |
| 94.4 | 0.7975 | 1.6350 | 2.4325 | 2.6875 |
| 94.5 | 0.8 | 1.6350 | 2.435 | 2.8925 |
| 94.6 | 0.8025 | 1.6400 | 2.4425 | 2.8975 |
| 94.7 | 0.3025 | 1.6425 | 2.445 | 2.9025 |
| 94.8 | 0.8025 | 1.6450 | 2.4475 | 2.905 |
| 94.9 | 0.8075 | 1.6475 | 2.455 | 2.9125 |
| 95.0 | 0.8075 | 1.6500 | 2.4575 | 2.9175 |
| 95.1 | 0.8075 | 1.6550 | 2.4625 | 2.9225 |
| 95.2 | 0.31 | 1.6575 | 2.4675 | 2.9275 |

APPENDIX 3-continued

Lookup mass as function of dP (inside)

| | Delta T | | | |
|---|---|---|---|---|
| | 5 C. Delta | 10 C. Delta | 15 C. Delta | 18 C. Delta |
| 95.3 | 0.81 | 1.6600 | 2.47 | 2.9325 |
| 95.4 | 0.8125 | 1.6625 | 2.475 | 2.9375 |
| 95.5 | 0.8125 | 1.6650 | 2.4775 | 2.9425 |
| 95.6 | 0.815 | 1.6700 | 2.485 | 2.95 |
| 95.7 | 0.3175 | 1.6700 | 2.4875 | 2.9525 |
| 95.8 | 0.8175 | 1.6750 | 2.4925 | 2.96 |
| 95.9 | 0.82 | 1.6775 | 2.4975 | 2.9625 |
| 96.0 | 0.8225 | 1.6800 | 2.5025 | 2.97 |
| 96.1 | 0.8225 | 1.6850 | 2.5075 | 2.9775 |
| 96.2 | 0.8225 | 1.6875 | 2.51 | 2.93 |
| 96.3 | 0.8275 | 1.6900 | 2.5175 | 2.9875 |
| 96.4 | 0.8275 | 1.6925 | 2.52 | 2.99 |
| 96.5 | 0.8275 | 1.6975 | 2.525 | 2.91175 |
| 96.6 | 0.83 | 1.6975 | 2.5275 | 3 |
| 96.7 | 0.83 | 1.7025 | 2.5325 | 3.0075 |
| 96.8 | 0.835 | 1.7000 | 2.535 | 3.0075 |

What is claimed is:

1. A method that is stored in tangible form and accessible by a data processing system for determination of xenon propellant remaining in a tank for a defined life condition, the method comprising:
    Establishing, using a heater controller, a first stable temperature in a non-ideal gas zone for gas above a critical point in a high-pressure propellant tank;
    measuring a temperature and a pressure at the first stable temperature of the propellant tank;
    establishing a second higher stable temperature in the non-ideal gas zone for gas above the critical point in the high-pressure propellant tank;
    measuring a temperature and a pressure at a second stable temperature; and
    computing by a computer processor a mass based on density in accordance with measurements of temperature and pressure at the first stable temperature and the second stable temperature whereby a determined differential pressure for a given differential temperature can only occur at a specific mass of remaining propellant in the tank.

2. The method of claim 1 further comprising:
    establishing a first table for pressure, temperature and density of xenon in a non-ideal gas depletion zone.

3. The method of claim 2 further comprising:
    converting the first table to a second table for reverse pressure calculation.

4. The method of claim 3 further comprising:
    determining volume of the propellant tank based on pressure and temperature and converting the density to a mass of remaining propellant.

5. The method of claim 4 wherein measurements of the first stable temperature and the second stable temperature includes the step of subtracting the first stable temperature from the higher stable temperature and the pressure at the first stable temperature from pressure at the second stable temperature to establish the differential temperature and the differential pressure for determination of propellant mass remaining in the tank.

6. The method of claim 4 further comprising:
    overlapping values contained in the first table and second table and subtracting a temperature scale and a pressure scale to obtain a mass table that is a function of differential temperature and differential pressure in the non-ideal gas zone.

7. A xenon quantity gauging system comprising:
    a control computer having a memory;
    a heater controller operatively connected to the control computer to establish a desired temperature delta of a non-ideal gas above a critical point in a high pressure tank over a period;
    a temperature sensor in the tank providing temperature data to the control computer over the period;
    a pressure sensor in the tank providing pressure data to the control computer over the period; and
    a mass calculation engine resident in the control computer configured to convert a calculated density of xenon propellant in the tank wherein a determined differential pressure for a given differential temperature can only occur at a specific remaining mass of xenon propellant in the tank.

8. The system of claim 7, further comprising:
    a compare module in the control computer receiving the temperature data and the pressure data to determine the differential temperature and differential pressure.

9. The system of claim 7, further comprising:
    a first table of standardized pressure/temperature/density for xenon in a non-ideal gas zone above the critical point stored in the memory.

10. The system of claim 9, further comprising:
    a first conversion engine in the control computer converting the first table to a second table of a reverse pressure calculation for storage in the memory.

11. The system of claim 10, further comprising a mass conversion engine for calculation of the remaining mass based on tank volume at pressures and temperatures corresponding to the first table and second table.

12. The system of claim 10 further comprising:
    a second conversion engine in the control computer converting the second table and first table into a differential pressure and differential temperature table for mass, said control computer providing an output of xenon quantity remaining.

13. A xenon propellant tankage system comprising:
    a xenon thruster;
    a propellant storage tank providing xenon propellant to the thruster and incorporating a heater;
    a control computer having a memory;
    a heater controller operatively connected to the control computer and the heater to establish a desired temperature delta of a non-ideal gas above a critical point in the tank over a period;
    a temperature sensor in the tank providing temperature data to the control computer over the period;
    a pressure sensor in the tank providing pressure data to the control computer over the period; and
    a plurality of software modules resident in the control computer configured to convert a calculated density of xenon propellant in the tank based on the temperature and the pressure data wherein a determined differential pressure for a given differential temperature can only occur at a specific remaining mass of xenon propellant in the tank.

14. The system of claim 13, wherein the plurality of software modules includes
    a compare module in the control computer receiving the temperature data and the pressure data.

15. The system of claim 13, wherein the plurality of software modules includes:
    a first table of standardized pressure/temperature/density for xenon in a non-ideal gas zone above the critical point stored in the memory.

16. The system of claim 15, wherein the plurality of software modules includes:
   a first conversion engine in the control computer converting the first table to a second table of a reverse pressure calculation for storage in the memory.

17. The system of claim 16, wherein the plurality of software modules includes
   a mass conversion engine for calculation mass based on the density of the first table for substitution in the first table and second table.

18. The system of claim 17 wherein the plurality of software modules includes:
   a second conversion engine in the control computer converting the second table and first table into a differential pressure and differential temperature table for mass, said control computer providing an output of xenon mass quantity remaining.

19. The system of claim 13 wherein the plurality of software modules are stored in the memory.

20. The system of claim 13 wherein the plurality of software modules are stored on tangible media.

* * * * *